US009649389B2

(12) United States Patent
Groves et al.

(10) Patent No.: US 9,649,389 B2
(45) Date of Patent: May 16, 2017

(54) SUBSTITUTED SILAXANTHENIUM RED TO NEAR-INFRARED FLUOROCHROMES FOR IN VITRO AND IN VIVO IMAGING AND DETECTION

(71) Applicant: VisEn Medical, Inc., Waltham, MA (US)

(72) Inventors: Kevin Groves, Arlington, MA (US); Ryan Buff, Watertown, MA (US)

(73) Assignee: VisEn Medical, Inc., Waltham, MA (US)

( * ) Notice: Subject to any disclaimer, the term of this patent is extended or adjusted under 35 U.S.C. 154(b) by 56 days.

(21) Appl. No.: 14/215,979

(22) Filed: Mar. 17, 2014

(65) Prior Publication Data
US 2014/0314677 A1    Oct. 23, 2014

Related U.S. Application Data

(60) Provisional application No. 61/794,188, filed on Mar. 15, 2013.

(51) Int. Cl.
| | | |
|---|---|---|
| *A61B 5/00* | (2006.01) | |
| *A61B 8/00* | (2006.01) | |
| *A61B 10/00* | (2006.01) | |
| *A61K 47/48* | (2006.01) | |
| *C07F 7/08* | (2006.01) | |
| *C09B 11/28* | (2006.01) | |
| *C09B 69/00* | (2006.01) | |
| *G01N 33/569* | (2006.01) | |
| *A61K 49/00* | (2006.01) | |

(52) U.S. Cl.
CPC .. *A61K 47/48023* (2013.01); *A61K 47/48092* (2013.01); *A61K 47/48384* (2013.01); *A61K 49/0021* (2013.01); *A61K 49/0054* (2013.01); *C07F 7/0816* (2013.01); *C09B 11/28* (2013.01); *C09B 69/008* (2013.01); *G01N 33/56966* (2013.01); *A61K 49/0019* (2013.01)

(58) Field of Classification Search
None
See application file for complete search history.

(56) References Cited

U.S. PATENT DOCUMENTS

| | | |
|---|---|---|
| 4,219,335 A | 8/1980 | Ebersole |
| 5,164,297 A | 11/1992 | Josephson et al. |
| 5,445,970 A | 8/1995 | Rohr |
| 5,593,658 A | 1/1997 | Bogdanov et al. |
| 6,046,585 A | 4/2000 | Simmonds |
| 6,048,982 A | 4/2000 | Waggoner |
| 6,083,485 A | 7/2000 | Licha et al. |
| 6,083,486 A | 7/2000 | Weissleder et al. |
| 6,086,737 A | 7/2000 | Patonay et al. |
| 6,136,612 A | 10/2000 | Della Ciana et al. |
| 6,258,340 B1 | 7/2001 | Licha et al. |
| 6,275,031 B1 | 8/2001 | Simmonds |
| 6,448,008 B1 | 9/2002 | Caputo et al. |
| 6,534,041 B1 | 3/2003 | Licha et al. |
| 6,592,847 B1 | 7/2003 | Weissleder et al. |
| 6,615,063 B1 | 9/2003 | Ntziachristos et al. |
| 6,740,755 B2 | 5/2004 | Caputo et al. |
| 6,747,159 B2 | 6/2004 | Caputo et al. |
| 6,869,593 B2 | 3/2005 | Frangioni |
| 6,913,743 B2 | 7/2005 | Licha et al. |
| 6,926,885 B2 | 8/2005 | Licha et al. |
| 7,025,949 B2 | 4/2006 | Licha et al. |
| 7,374,746 B2 | 5/2008 | Frangioni |
| 7,947,256 B2 | 5/2011 | Rajopadhye et al. |
| 8,173,819 B2 | 5/2012 | Rajopadhye et al. |
| 8,221,721 B2 | 7/2012 | Narayanan |
| 8,420,055 B2 | 4/2013 | Gaw et al. |
| 8,455,651 B2 | 6/2013 | Rajopadhye et al. |
| 8,486,373 B2 | 7/2013 | Weissleder et al. |
| 8,685,370 B2 | 4/2014 | Rajopadhye et al. |
| 8,771,646 B2 | 7/2014 | Rajopadhye et al. |
| 8,815,214 B2 | 8/2014 | Rajopadhye et al. |
| 8,864,821 B2 | 10/2014 | Jaffer et al. |
| 9,365,721 B2 | 6/2016 | Narayanan |
| 9,371,362 B2 | 6/2016 | Ho |
| 2002/0064794 A1 | 5/2002 | Leung et al. |
| 2003/0124194 A1 | 7/2003 | Gaw et al. |
| 2003/0219383 A1 | 11/2003 | Weissleder et al. |
| 2005/0106106 A1 | 5/2005 | Licha et al. |
| 2005/0169843 A1 | 8/2005 | Weissleder et al. |

(Continued)

FOREIGN PATENT DOCUMENTS

| | | |
|---|---|---|
| CN | 1810812 A | 8/2006 |
| CN | 100361999 C | 1/2008 |

(Continued)

OTHER PUBLICATIONS

Abe S et al., 'Correlation of in vivo Autofluorescence Endoscopy Images with Histopathologic Findings in Stomach Cancer,' Endoscopy, Apr. 2000 (Apr. 2000), 32(4):281-6.
Alexander W, 'Lasers Investigated as Diagnostic Tools for Breast Cancer,' J Clin Laser Med Surg, Dec. 1991 (Dec. 1991), 9(6):416-8.
Alfano RR et al., 'Advances in Optical Imaging of Biomedical Media,' Ann NY Acad Sci, May 30, 1997 (May 30, 1997), 820:248-70.
Boas DA et al., 'Scattering of Diffuse Photon Density Waves by Spherical Inhomogeneities Within Turbid Media: Analytic Solution and Applications,' Proc Natl Acad Sci USA, May 24, 1994 (May 24, 1994), 91(11):4887-91.

(Continued)

*Primary Examiner* — Michael G Hartley
*Assistant Examiner* — Melissa Perreira
(74) *Attorney, Agent, or Firm* — Goodwin Procter LLP

(57) ABSTRACT

The invention provides a family of fluorescent compounds. The compounds are substituted silaxanthenium compounds that can be chemically linked to one or more biomolecules, such as a protein, nucleic acid, and therapeutic small molecule. The compounds can be used for imaging in a variety of medical, biological and diagnostic applications. The dyes are particularly useful for in vitro, in vivo and ex vivo imaging applications.

25 Claims, 12 Drawing Sheets

(56) References Cited

U.S. PATENT DOCUMENTS

| | | | |
|---|---|---|---|
| 2005/0169844 | A1 | 8/2005 | Licha et al. |
| 2005/0171434 | A1 | 8/2005 | Madden et al. |
| 2005/0245734 | A1 | 11/2005 | Caputo et al. |
| 2006/0002857 | A1 | 1/2006 | Frangioni |
| 2006/0239916 | A1 | 10/2006 | Licha et al. |
| 2008/0226562 | A1 | 9/2008 | Groves et al. |
| 2009/0123383 | A1 | 5/2009 | Frangioni |
| 2009/0130024 | A1 | 5/2009 | Narayanan et al. |
| 2010/0074847 | A1 | 3/2010 | Madden et al. |
| 2010/0166659 | A1 | 7/2010 | Licha et al. |
| 2010/0172841 | A1 | 7/2010 | Peterson et al. |
| 2010/0189657 | A1 | 7/2010 | Weissleder et al. |
| 2011/0152501 | A1 | 6/2011 | Weissleder et al. |
| 2011/0171136 | A1 | 7/2011 | Poss et al. |
| 2011/0256065 | A1 | 10/2011 | Frangioni |
| 2012/0321563 | A1 | 12/2012 | Groves et al. |
| 2014/0348746 | A1 | 11/2014 | Narayanan |
| 2015/0018517 | A1 | 1/2015 | Rajopadhye et al. |
| 2015/0133773 | A1 | 5/2015 | Jaffer et al. |

FOREIGN PATENT DOCUMENTS

| | | |
|---|---|---|
| WO | WO-00/64988 A1 | 11/2000 |
| WO | WO-03/079015 A1 | 9/2003 |
| WO | WO-03/102558 A1 | 12/2003 |
| WO | WO-2010/126077 A1 | 11/2010 |
| WO | WO-2012/083064 A1 | 6/2012 |
| WO | WO-2012/111818 A1 | 8/2012 |
| WO | WO-2012/118715 A2 | 9/2012 |
| WO | WO-2013/029650 A1 | 3/2013 |
| WO | WO-2014/144793 A1 | 9/2014 |

OTHER PUBLICATIONS

Chance B, 'Near-Infrared Images Using Continuous, Phase-Modulated, and Pulsed Light with Quantiation of Blood and Blood Oxygenation,' Ann NY Acad Sci, Feb. 9, 1998 (Feb. 9, 1998), 838:29-45.

Chemla YR et al., 'Ultrasensitive Magnet Biosensor for Homogeneous Immunoassay,' Proc Natl Acad Sci USA, Dec. 19, 2000 (Dec. 19, 2000), 97(26):14268-72.

Cheng X and Boas D, 'Diffuse Optical Reflection Tomography Using Continuous Wave Illumination,' Opt Express, Aug. 3, 1998 (Aug. 3, 1998), 3(3):118-23.

Citrin D and Camphausen K, 'Optical Imaging of Mice in Oncologic Research,' Expert Rev Anticancer Ther, Oct. 2004 (Oct. 2004), 4(5):857-64.

Dellian M et al., 'Vascular Permeability in a Human Tumor Xenograft: Molecular Charge Dependence,' Br J Cancer, May 2000 (May 2000), 82(9):1513-8.

Fu M et al., 'A Design Concept of Long-Wavelength Fluorescent Analogs of Rhodamine Dyes: Replacement of Oxygen with Silicon Atom,' Chem Commun (Camb), Feb. 14, 2008 (Feb. 14, 2008)(ePub), (15):1780-2.

Fukumura D et al., 'Tumor Induction of VEGF Promoter Activity in Stromal Cells,' Sep. 18, 1998 (Sep. 18, 1998), 94(6):715-25.

Gahlen J et al., 'Spectrometry Supports Fluorescence Staging Laparoscopy After Intraperitoneal Aminolaevulinic Acid Lavage for Gastrointestinal Tumors,' J Photochem Photobiol B, Sep.-Oct. 1999 (Sep.-Oct. 1999), 52(1-3):131-5.

Garfinkle BD and Henley MW, 'Chapter 40: Sterilization,' Remington: The Science and Practice of Pharmacy, 20th Ed, 2000 (2000), D Limmer (Ed), Lippincott Williams & Wilkins, Baltimore, MD (Publ), pp. 753-779 ISBN: 0-683-306472.

González S et al., 'Characterization of Psoriasis in vivo Reflectance Confocal Microscopy,' J Med, 1999 (1999), 30(5-6):337-56.

Graves EE et al., 'Fluorescence Molecular Imaging of Small Animal Tumor Models,' Curr Mol Med, Jun. 2004 (Jun. 2004), 4(4):419-30.

Hecht G and Block LH, 'Chapters 43 and 44,' Remington: The Science and Practice of Pharmacy, 20th Ed, 2000 (2000), D Limmer (Ed), Lippincott Williams & Wilkins, Baltimore, MD (Publ), pp. 821-857 ISBN: 0-683-306472.

Hirsch FR et al., 'Early Detection of Lung Cancer: Clinical Perspectives of Recent Advances in Biology and Radiology,' Clin Cancer Res, Jan. 2001 (Jan. 2001), 7(1):5-22.

International Searching Authority, International Preliminary Report on Patentability (Form PCT/ISA/237) for International Patent Application No. PCT/US2014/029350, (Eberhard M), completed on Jun. 13, 2014 (Jun. 13, 2014) and issued on Sep. 15, 2015 (Sep. 15, 2015), pp. 1-10.

International Searching Authority, International Search Report (Form PCT/ISA/210) for International Patent Application No. PCT/US2014/029350, (Eberhard M), completed on Jun. 13, 2014 (Jun. 13, 2014) and mailed on Jun. 26, 2014 (Jun. 26, 2014), pp. 1-7.

Izuishi K et al., 'Detection of Bile Duct Cancer by Autofluorescence Cholangioscopy: A Pilot Study,' Hepatogastroenterology, Mar.-Apr. 1999 (Mar.-Apr. 1999), 46(26):804-7.

Kim E et al., 'Red Si-Rhodamine Drug Conjugates Enable Imaging in GFP Cells,' Chem Commun (Camb), May 4, 2014 (May 4, 2014), 50(34):4504-7.

Koide Y et al., 'Development of an Si-Rhodamine-Based Far-Red to Near-Infrared Fluorescence Probe Selective for Hypochlorous Acid and its Applications for Biological Imaging,' J Am Chem Soc, Mar. 28, 2011 (Mar. 28, 2011)(ePub), 133(15):5680-2.

Koide Y et al., 'Development of NIR Fluorescent Dyes Based on Si-Rhodamine for in vivo Imaging,' J Am Chem Soc, Mar. 7, 2012 (Mar. 7, 2012)(ePub), 134(11):5029-31.

Koide Y et al., 'Evolution of Group 14 Rhodamines as Platforms for Near-Infrared Fluorescence Probes Utilizing Photoinduced Electron Transfer,' ACS Chem Biol, Mar. 17, 2011 (Mar. 17, 2011)(ePub), 6(6):600-8.

Koo V et al., 'Non-Invasive in vivo Imaging in Small Animal Research,' Cell Oncol, 2006 (2006), 28(4):127-39.

Korlach J et al., 'Characterization of Lipid Bilayer Phases by Confocal Microscopy and Fluorescence Correlation Spectroscopy,' Proc Natl Acad Sci USA, Jul. 20, 1999 (Jul. 20, 1999), 96(15):8461-6.

Kriegmair M et al., '5-Aminolevulinic Acid-Induced Fluorescence Endoscopy for the Detection of Lower Urinary Tract Tumors,' Urol Int, 1999 (1999), 63(1):27-31.

Kushida Y et al., 'Red Fluorescent Scaffold for Highly Sensitive Protease Activity Probes,' Bioorg Med Chem Lett, May 2, 2012 (May 2, 2012)(ePub), 22(12):3908-11.

Leamon CP and Low PS, 'Folate-Mediated Targeting: From Diagnostics to Drug and Gene Delivery,' Drug Discov Today, Jan. 1, 2001 (Jan. 1, 2001), 6(1):44-51.

Major AL et al., 'In vivo Fluorescence Detection of Ovarian Cancer in the NuTu-19 Epithelial Ovarian Cancer Animal Model Using 5-Aminolevulinic Acid (ALA),' Gynecol Oncol, Jul. 1997 (Jul. 1997), 66(1):122-32.

Monsky WL et al., 'Augmentation of Transvascular Transport of Macromolecules and Nanoparticles in Tumors Using Endothelial Growth Factor,' Cancer Res, Aug. 15, 1999 (Aug. 15, 1999), 59(16):4129-35.

Mycek MA et al., 'Colonic Polyp Differentiation Using Time-Resolved Autofluorescence Spectroscopy,' Gastrointest Endosc, Oct. 1998 (Oct. 1998), 48(4):390-4.

Myochin T et al., 'Design Strategy for a Near-Infrared Fluorescence Probe for Matrix Metalloproteinase Utilizing Highly Cell Permeable Boron Dipyrromethene,' J Am Chem Soc, Aug. 7, 2012 (Aug. 7, 2012)(ePub), 134(33):13730-7.

Nairn JG, 'Chapter 39, Solutions, Emulsions, Suspensions, and Extracts,' Remington: The Science and Practice of Pharmacy, 20th Ed, 2000 (2000), D Limmer (Ed), Lippincott Williams & Wilkins, Baltimore, MD (Publ), pp. 721-752 ISBN: 0-683-306472.

Ntziachristos V et al., 'Concurrent MRI and Diffuse Optical Tomography of Breast After Indocyanine Green Enhancement,' Proc Natl Acad Sci USA, Mar. 14, 2000 (Mar. 14, 2000), 97(6):2767-72.

Ntziachristos V et al., 'Fluorescence Imaging with Near-Infrared Light: New Technological Advances that Enable in vivo Molecular Imaging,' Eur Radiol, Jul. 19, 2002 (Jul. 19, 2002)(ePub), 13(1):195-208.

Ntziachristos V et al., 'Fluorescence Molecular Tomography Resolves Protease Activity in vivo,' Nat Med, Jun. 24, 2002 (Jun. 24, 2002)(ePub), 8(7):757-60.

(56) References Cited

OTHER PUBLICATIONS

Ntziachristos V, 'Fluorescence Molecular Imaging,' Annu Rev Biomed Eng, 2006 (2006), 8:1-33.
Perez JM et al., 'Magnetic Relaxation Switches Capable of Sensing Molecular Interactions,' Nat Biotechnol, Jul. 22, 2002 (Jul. 22, 2002)(ePub), 20(8):816-20.
Piao W et al., 'Development of Azo-Based Fluorescent Probes to Detect Different Levels of Hypoxia,' Angew Chem Int Ed Engl, Oct. 14, 2013 (Oct. 14, 2013)(ePub), 52(49):13028-32.
Rajadhyaksha M et al., 'In vivo Confocal Scanning Laser Microscopy of Human Skin: Melanin Provides Strong Contrast,' J Invest Dermatol, Jun. 1995 (Jun. 1995), 104(6):946-52.
Rao J et al., 'Fluorescence Imaging in vivo: Recent Advances,' Curr Opin Biotechnol, Jan. 17, 2007 (Jan. 17, 2007)(ePub), 18(1):17-25.
Riedl CR et al., 'Fluorescence Detection of Bladder Tumors with 5-amino-levulinic Acid,' J Endourol, Dec. 1999 (Dec. 1999), 13(10):755-9.
Siegel A et al., 'Design and Evaluation of a Continuous-Wave Diffuse Optical Tomography System,' Opt Express, Apr. 12, 1999 (Apr. 12, 1999), 4(8):287-98.
Stepp H et al., 'Fluorescence Endoscopy of Gastrointestinal Diseases: Basic Principles, Techniques, and Clinical Experience,' Endoscopy, May 1998 (May 1998), 30(4):379-86.
Tearney GJ et al., 'Images in Cardiovascular Medicine, Catheter-Based Optical Imaging of a Human Coronary Artery,' Circulation, Dec. 1, 1996 (Dec. 1, 1996), 94(11):3013.
Tearney GJ et al., 'In vivo Endoscopic Optical Biopsy with Optical Coherence Tomography,' Science, Jun. 27, 1997 (Jun. 27, 1997), 276(5321):2037-9.
Various, 'Chapters 37 and 38,' Remington: The Science and Practice of Pharmacy, 20th Ed, 2000 (2000), D Limmer (Ed), Lippincott Williams & Wilkins, Baltimore, MD (Publ), pp. 681-720 ISBN: 0-683-306472.
Various, 'Chapters 41 and 42,' Remington: The Science and Practice of Pharmacy, 20th Ed, 2000 (2000), D Limmer (Ed), Lippincott Williams & Wilkins, Baltimore, MD (Publ), pp. 780-820 ISBN: 0-683-306472.
Various, 'Chapters 45 and 46,' Remington: The Science and Practice of Pharmacy, 20th Ed, 2000 (2000), D Limmer (Ed), Lippincott Williams & Wilkins, Baltimore, MD (Publ), pp. 858-902 ISBN: 0-683-306472.
Various, 'Chapters 47, 50 and 52,' Remington: The Science and Practice of Pharmacy, 20th Ed, 2000 (2000), D Limmer (Ed), Lippincott Williams & Wilkins, Baltimore, MD (Publ), pp. 903-929, 963-979, 986-994 ISBN: 0-683-306472.
Wang T et al., 'Spirolactonized Si-Rhodamine: A Novel NIR Fluorophore Utilized as a Platform to Construct Si-Rhodamine-Based Probes,' Chem Commun (Camb), Jul. 26, 2012 (Jul. 26, 2012)(ePub), 48(70):8781-3.
Ward HA, 'New Laser Techniques for Diagnosis and Treatment of Deep-Seated Brain Lesions,' J Laser Appl, Oct. 1998 (Oct. 1998), 10(5):224-8.
Weissleder R, 'A Clearer Vision for in vivo Imaging,' Nat Biotechnol, Apr. 2001 (Apr. 2001), 19(4):316-7.
Westbrook C, Handbook of MRI Technique, 2nd Ed, 2002 (2002), Blackwell Science, Ltd, Oxford, UK (Publ), pp. 3-44 ISBN: 0-632-05264-3.

SUBSTITUTED SILAXANTHENIUM RED TO NEAR-INFRARED FLUOROCHROMES FOR IN VITRO AND IN VIVO IMAGING AND DETECTION

CROSS REFERENCE TO RELATED APPLICATIONS

This application claims the benefit of U.S. Provisional Application No. 61/794,188, filed on Mar. 15, 2013, which is incorporated herein by reference in its entirety.

FIELD OF THE INVENTION

The invention provides compositions and methods of using fluorescent dyes (fluorochromes). The compositions generally contain a silaxanthenium fluorochrome which can be used in various medical, diagnostic and biological applications. The fluorochromes enable fluorescent detection in in vitro, ex vivo and in vivo imaging applications.

BACKGROUND

Optical imaging and detection methods offer a number of advantages over other imaging and detection methods. Imaging of tissues, organs or whole subjects typically uses light in the red and near-infrared (NIR) ranges (600-1200 nm) to maximize tissue penetration and minimize absorption from natural biological absorbers such as hemoglobin and water and autofluorescence from biological molecules. Optical imaging may provide high sensitivity, does not require exposure of test subjects or laboratory personnel to ionizing radiation, can allow for simultaneous use of multiple, distinguishable probes (which may be important in molecular imaging), and offers high temporal and spatial resolution, which is important in functional imaging, detection, diagnostic applications, microscopy, cytometry, tissue imaging, and in vitro and in vivo imaging.

In fluorescence imaging or detection, filtered light or a laser with a defined bandwidth is used as a source of excitation light. The excitation light travels through body tissue or other analytical sample such as a microscope slide, a cell, or a multi-well plate, and when the excitation light encounters a reporter molecule (for example, a contrast agent, sensitizer, fluorochrome or imaging probe), the light is absorbed. The reporter molecule then emits light, or transfers excitation signal or energy to another molecule that can emit light, that has detectably different properties from the excitation light. The resulting emitted light then can be used to construct an image or quantify the amount of reporter in the sample. Most optical imaging techniques have relied on the use of organic and inorganic fluorescent dyes (fluorochromes) as the reporter molecule.

Fluorescent dyes or fluorochromes are generally known and used for fluorescence labeling and detection of various biological and non-biological materials by procedures such as fluorescence microscopy, fluorescence immunoassay, and flow cytometry. A typical method for labeling such materials with fluorescent dyes is to create a fluorescent complex by means of bonding between suitable groups on the dye molecule and compatible groups on the material to be labeled. In this way, materials such as cells, tissues, amino acids, proteins, antibodies, drugs, hormones, nucleotides, nucleic acids, lipids and polysaccharides and the like may be chemically labeled and detected or quantified, or may be used as fluorescent probes which can bind specifically to target materials and be detected by fluorescence detection methods. Brightly fluorescent dyes permit detection or localization of the attached materials with great sensitivity.

Optical imaging with fluorescent dyes has emerged as a powerful imaging modality with significant advantages over other modalities both in vitro and in vivo. Dyes that fluoresce in the far red to near-infrared (NIR) region (630-900 nm) are essential for in vivo imaging due to the superior penetration of light through tissue at these wavelengths relative to longer and shorter wavelength light, which is absorbed by water and hemoglobin. NIR dyes also absorb and emit far outside of the typical range of tissue autofluorescence, making them extremely well suited for in vitro imaging of tissues and cells.

For many years, indocyanine dyes have been the dominant class of dyes used for NIR fluorescent imaging in vivo, with indocyanine green (molecular weight 775 Da) being one of the best known NIR dyes approved for diagnostic use in humans. In addition, numerous derivatized versions of indocyanines bearing various linking functionality such as carboxylic acids have been developed for use in bioconjugation and imaging applications. However, the current molecular constructs that are fluorescent in the NIR region, including the indocyanine family, tend to be large in size (>750 Da) and have poor solubility in water necessitating the incorporation of solubilizing groups such as multiple sulfonate groups. The resulting dyes then show very low cell membrane permeability, limiting their use for the targeting of intracellular structures.

There is an increasing need to develop novel, far red to NIR fluorescent fluorophores that are smaller and highly permeable to cell membranes so as to expand the reach of NIR imaging to intracellular targets, both in vitro and in vivo. The ideal fluorophores for such purposes would be small in size (<750 Da), have good water solubility, have absorbance and emission profiles in the far red to NIR range with high extinction coefficients and quantum yields, be highly permeable to the membranes of living cells and have tunable optical properties through variation of key substituents.

Notwithstanding, there is an ongoing need for new dyes that can be used in various medical, diagnostic and biological applications. There is a need for dyes that work well in in vitro, ex vivo and in vivo applications.

SUMMARY OF THE INVENTION

The present invention describes fluorescent compounds (fluorochromes) based on a silaxanthenium core that are sufficiently red-shifted through use of selected substituents to fall into the far-red and NIR spectrum which can be used for imaging and detection applications, both in vitro and in vivo. In an embodiment, the invention provides a family of fluorescent 9-substituted 3,6-diamino 10-silaxanthenium fluorochromes with red to near infrared absorption and emission wavelengths. In certain embodiments, the fluorochromes of the present invention have a low molecular weight (less than about 750 Da), exhibit significant cell permeability and have optical properties that can be modified by variation of selected substituents or substituent location/orientation with respect to the silaxanthenium core.

In one embodiment, the invention provides a compound represented by Formula I:

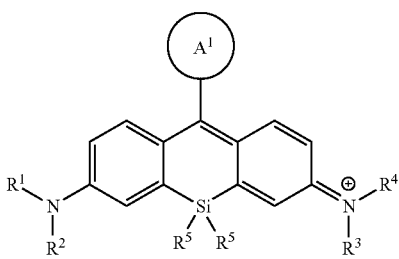

(I)

or a salt thereof, wherein the variables are as defined in the detailed description.

In another embodiment, the invention provides fluorescent silaxanthenium fluorochromes represented by the following formula:

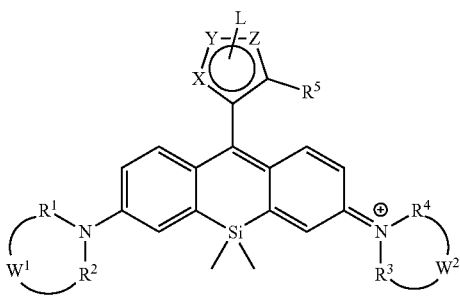

and salts thereof, wherein $R^1$, $R^2$, $R^3$, $R^4$, $R^5$, L, $W^1$, $W^2$, X, Y, and Z are described in more detail below. In one embodiment, $W^1$ or $W^2$ comprise an aliphatic or aromatic carbocyclic or heterocyclic moiety. In another embodiment, X, Y, or Z comprise a heteroatom, for example N, O, S, or Si. In another embodiment, the substituents represented by $R^1$, $R^2$, $R^3$, $R^4$, $R^5$, L, $W^1$, $W^2$, X, Y, or Z improve the optical properties of the 9-Silaxanthenium core by, for example, inducing a shift in the optical absorbance or emission wavelengths or increasing the quantum yield or photostability. In other embodiments, the invention provides compounds that are permeable to cell membranes.

In certain embodiments, the compound has a molecular weight less than 750 Daltons. In other embodiments, the compound has a molecular weight from about 400 to 750 Daltons. In other embodiments, the compound has a molecular weight less than 500 Daltons.

In certain embodiments, the compound has an absorption and emission wavelength in the range from about 500 nm to 1100 nm. In other embodiments, the compound has an absorption and emission wavelength in the range from about 600 nm to 850 nm. In other embodiments the compound is fluorescent in the far-red to near-infrared region.

In certain embodiments, the compound is a fluorescent biomolecule represented by:

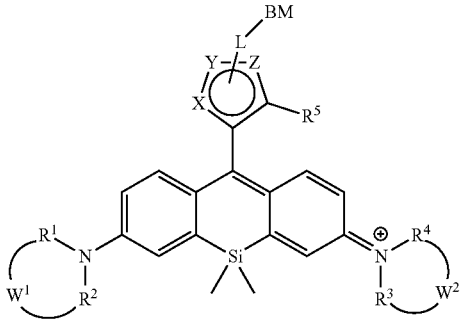

or a salt thereof, wherein; X, Y and Z are, independently, O, S, N, Si, C or (C=C). L is a linking group optionally bearing a functional group or reactive group, such as a carboxylate, carboxyalkyl, maleimide, succinimidyl ester, carboxamide, propargyl, azidoalkyl, isothiocyanate, of —NH$_2$—OH, —SH, —SO$_3$H, carboxyl, —COCl, —(CO)O(CO)R$^7$— CONHNH$_2$, acetoxymethyl esters, substituted and unsubstituted N-hydroxysuccinimidyl esters, substituted and unsubstituted N-hydroxysulfosuccinimido esters, nitro- or fluoro or phenol esters, azide, —NCS, —CHO, azide, —COCH$_2$I, phosphoramidite, phthalamido, or maleimide, wherein $R^7$ is selected from the group consisting of H, alkyl and aryl;

BM is a biomolecule, wherein the fluorescent biomolecule comprises at least one BM.

$R^1$, $R^2$, $R^3$ and $R^4$ are, independently, H, methyl, ethyl, alkyl, or cyclic alkyl, aryl, substituted aryl, heteroaryl, or heterocyclic (e.g. morpholine) alkynyl, carboxyalkyl, aminoalkyl, haloalkyl, azidoalkyl, amide, amino acid, or peptide;

$R^5$ is absent or is H, $C_{1-20}$ alkyl, carboxyl, carboxyalkyl, sulfonate, sulfonamide, halogen, hydroxy, amine, amide, nitro, cyano, O-alkyl, S-alkyl, silyl, O-silyl methyl, ethyl, isopropyl, carboxyalkyl, haloalkyl, alkylsulfhydryl, trifluoromethyl, hydrazide; and $W^1$ and $W^2$ are, independently, absent or cyclic groups containing aliphatic carbon, nitrogen, oxygen, sulfur, or silicon forming a 4 to 9 membered ring with $R^2$ and $R^3$ or $R^4$ and $R^5$, optionally with further substituents. In another embodiment, the compound comprises a biomolecule (BM) wherein BM is a cell, a protein or a nucleic acid.

In certain embodiments, the invention provides an in vitro imaging method, the method comprising: (a) contacting a sample with an agent of the present invention; (b) allowing the agent to bind to a biological target; (c) optionally removing unbound agent; and (d) detecting signal emitted from the agent thereby to determine whether the agent has been activated by or bound to the biological target. In other embodiments the sample is a biological sample. In other embodiments, the optical signal emitted by the fluorochrome, is detected, for example, with a fluorescence microscope, flow cytometer, or other suitable detection device.

In certain embodiments, the invention provides an ex vivo imaging method, the method comprising: (a) contacting a sample with an agent of the present invention; (b) allowing the agent to bind to a biological target; (c) optionally removing unbound agent; and (d) detecting signal emitted from the agent thereby to determine whether the agent has been activated by or bound to the biological target. In other embodiments the sample is a biological sample.

In certain embodiments, the invention provides a method of in vivo imaging, the method comprising: (a) administering to a subject an agent of the present invention; (b) allowing the agent to distribute within the subject; and (c) detecting a signal emitted by the agent.

In another embodiment, the invention provides an in vivo optical imaging method wherein the method comprises (a) administering to a subject, for example an animal or a human, a fluorochrome of the present invention or a conjugate thereof; (b) allowing the fluorochrome or conjugate thereof to distribute within the subject or to contact, interact with or bind to a biological target; (c) exposing the subject to light of a wavelength absorbable by the fluorochrome; and (d) detecting the optical signal emitted by the fluorochrome, for example, with an endoscope, catheter, tomographic imaging system, epifluorescence or reflectance imaging system, hand-held optical imaging system, intraoperative systems or microscope.

In certain embodiments, the imaging methods of the present invention allow for signal emitted by a compound to be used to construct an image. In other embodiments, the image is a tomographic image. In other embodiments, steps (a)-(c) are repeated at predetermined time intervals thereby to permit evaluation of the emitted signals over time. In other embodiments, the illuminating and detecting steps are performed using an endoscope, catheter, tomographic system, hand-held optical imaging system, or an intraoperative microscope.

In certain embodiments, wherein in step (a), when two or more imaging or detection agents whose signal properties are distinguishable from one another are administered to a subject or applied to a sample, such as a biological or chemical sample, at least one of the imaging or detection agents is a compound of the present invention. In other embodiments, the compounds of the present invention are used with one or more imaging or detection agents, described herein or known in the art, in a multiplexed assay for imaging or detecting multiple targets in a single sample or subject.

In certain embodiments, the invention provides methods for the detection or quantification of an analyte in a sample, such as a biological sample. In other embodiments, the detection method is a homogeneous assay. In other embodiments, the method is a heterogeneous assay. In other embodiments, the method is a time resolved fluorescent or luminescent assay. In another embodiment, the method is a signal amplification assay, such as a tyramide signal amplification assay.

In certain embodiments, the materials and methods of the invention are used as a component in a high throughput screening assay. In other embodiments, the materials and methods of the invention are used as a component in a high content screening assay.

In certain embodiments, the disclosed methods can be used to detect, monitor or diagnose diseases or biological conditions, for example bone disease, cancer, cardiovascular disease, dermatological disease, environmental disease, immunologic disease, infectious disease, inflammation, inherited disease, metabolic disease, neurodegenerative disease, ophthalmic disease, and respiratory disease. Such diseases or biological conditions can be detected, monitored or diagnosed in biological samples such as cells, tissues, biopsies, or living subjects such as an animal or human.

In certain embodiments, cells are labeled with a fluorochrome compound described herein and the resulting labeled cells administered to the subject. The signal emitted by the fluorochrome compound can be used to monitor transport and localization of the cells or to evaluate the efficacy of a cell therapy.

DETAILED DESCRIPTION OF THE INVENTION

Figure 1A:
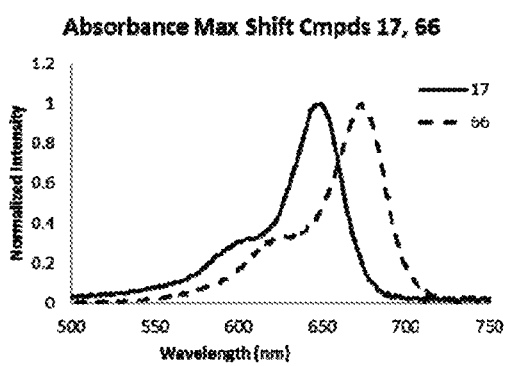
FIG. 1A and FIG. 1B illustrate a 23 nm red shift observed upon moving the sulfur atom of a 9-thienyl SX compound from the Z position of Formula I (compound 17) to the X position and adding a bromine substituent (compound 66).

The present invention provides a family of silaxanthenium fluorochrome compounds (dyes) that absorb and/or emit light having a wavelength in the range from about 500 nm to about 1100 nm, more preferably in the range from about 600 nm to about 900 nm. In certain embodiments, the dyes absorb and/or emit light having a wavelength in the range from about 600 nm to about 850 nm, from about 650 nm to about 900 nm, or from about 650 nm to about 850 nm. The fluorochrome compounds or certain conjugates or derivatives thereof are permeable to cell membranes, can be conjugated to other molecules or biomolecules and are particularly useful in a variety of in vitro and in vivo imaging applications.

Generally, the fluorochromes of the invention can be represented by the formula $W^1$—$(SX)_{Ar}$—$W^2$, and salts thereof, wherein SX represents a 3,6-diamino-10-silaxanthenium core, Ar represents a substituted aryl or heteroaryl group at the 9-position of the SX core, and $W^1$ and $W^2$ each independently are absent or represent the same or different carbocyclic or heterocyclic groups around the 3- and 6-amino substituents of the SX core, respectively. One significant feature is how the substituents Ar, $W^1$ and $W^2$ affect the optical properties of the SX core. Certain terms employed in the specification, examples and appended claims are collected together in the following section.

I. DEFINITIONS

The definitions listed herein should be read in light of the remainder of the disclosure and understood as by a person of skill in the art. Unless defined otherwise, all technical and scientific terms used herein have the same meaning as commonly understood by a person of ordinary skill in the art to which this invention belongs.

"Chemically linked" means connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions. This also includes cross-linking or caging.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" also includes halosubstituted alkyls.

Moreover, the term "alkyl" includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like. In certain embodiments, the alkyl is unsubstituted. In certain embodiments, the alkyl is a straight or branched chain alkyl group that is unsubstituted.

The term "haloalkyl" refers to an alkyl group as defined above except that one or more hydrogen atoms have been replaced with a halogen.

The term "alkylene" refers to a diradical of a straight or branched chain alkyl group that is unsubstituted.

The terms "aralkyl" and "alkylaryl" are art-recognized and refer to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond, respectively.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, sulfamoyl, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms "heterocyclyl," "heterocyclic group" or "heterocyclic moiety" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl," "polycyclic group" or "polycyclo moiety" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth in "*Advanced Inorganic Chemistry*" by Cotton and Wilkinson.

The terms "amine" and "amino" are art-recognized and refer to both unsubstituted and substituted amines, e.g., a moiety that may be represented by the general formulas:

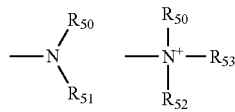

wherein $R_{50}$, $R_{51}$, $R_{52}$ and $R_{53}$ each independently represent a hydrogen, an alkyl, an alkenyl, $-(CH_2)_m-R_{61}$, or $R_{50}$ and $R_{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R_{50}$ or $R_{51}$ may be a carbonyl, e.g., $R_{50}$, $R_{51}$ and the nitrogen together do not form an imide. In other embodiments, $R_{50}$ and $R_{51}$ (and optionally $R_{52}$) each independently represent a hydrogen, an alkyl, an alkenyl, or $-(CH_2)_m-R_{61}$. Thus, the term "alkylamine" includes an amine group, as defined above, having a substituted or unsubstituted alkyl attached thereto, i.e., at least one of $R_{50}$ and $R_{51}$ is an alkyl group.

The term "acylamino" is art-recognized and refers to a moiety that may be represented by the general formula:

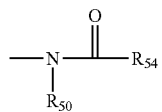

wherein $R_{50}$ is as defined above, and $R_{54}$ represents a hydrogen, an alkyl, an alkenyl or $-(CH_2)_m-R_{61}$, where m and $R_{61}$ are as defined above.

The term "amido" is art recognized as an amino-substituted carbonyl and includes a moiety that may be represented by the general formula:

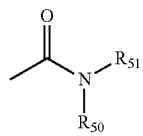

wherein $R_{50}$ and $R_{51}$ are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—$R_{61}$, wherein m and $R_{61}$ are defined above. Representative alkylthio groups include methylthio, ethylthio, and the like.

The term "carbonyl" is art recognized and includes such moieties as may be represented by the general formulas:

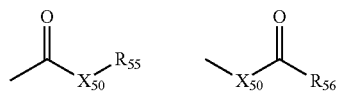

wherein $X_{50}$ is a bond or represents an oxygen or a sulfur, and $R_{55}$ and $R_{56}$ represents a hydrogen, an alkyl, an alkenyl, $-(CH_2)_m-R_{61}$ or a pharmaceutically acceptable salt, $R_{56}$ represents a hydrogen, an alkyl, an alkenyl or $-(CH_2)_m-R_{61}$, where m and $R_b$ are defined above. Where $X_{50}$ is an oxygen and $R_{55}$ or $R_{56}$ is not hydrogen, the formula represents an "ester." Where $X_{50}$ is an oxygen, and $R_{55}$ is as defined above, the moiety is referred to herein as a carboxyl group, and particularly when $R_{56}$ is a hydrogen, the formula represents a "carboxylic acid." Where $X_{50}$ is an oxygen, and $R_{56}$ is hydrogen, the formula represents a "formate." In general, where the oxygen atom of the above formula is replaced by sulfur, the formula represents a "thiolcarbonyl" group. Where $X_{50}$ is a sulfur and $R_{55}$ or $R_{56}$ is not hydrogen, the formula represents a "thiolester." Where $X_{50}$ is a sulfur and $R_{55}$ is hydrogen, the formula represents a "thiolcarboxylic acid." Where $X_{50}$ is a sulfur and $R_{56}$ is hydrogen, the formula represents a "thiolformate." On the other hand, where $X_{50}$ is a bond, and $R_{55}$ is not hydrogen, the above formula represents a "ketone" group. Where $X_{50}$ is a bond, and $R_{55}$ is hydrogen, the above formula represents an "aldehyde" group.

The terms "alkoxyl" or "alkoxy" are art-recognized and refer to an alkyl group, as defined above, having an oxygen attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—$R_{61}$, where m and $R_{61}$ are described above.

The term "sulfonate" is art recognized and refers to a moiety that may be represented by the general formula:

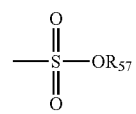

in which $R_{57}$ is an electron pair, hydrogen, alkyl, cycloalkyl, or aryl.

The term "sulfate" is art recognized and includes a moiety that may be represented by the general formula:

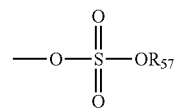

in which $R_{57}$ is as defined above.

The term "sulfonamido" is art recognized and includes a moiety that may be represented by the general formula:

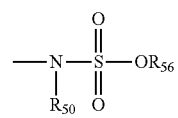

in which $R_{50}$ and $R_{56}$ are as defined above.

The term "sulfamoyl" is art-recognized and refers to a moiety that may be represented by the general formula:

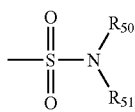

in which $R_{50}$ and $R_{51}$ are as defined above.

The term "sulfonyl" is art-recognized and refers to a moiety that may be represented by the general formula:

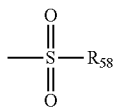

in which $R_{58}$ is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which $R_{58}$ is defined above.

The term "phosphoryl" is art-recognized and may in general be represented by the formula:

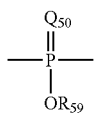

wherein $Q_{50}$ represents S or O, and $R_{59}$ represents hydrogen, a lower alkyl or an aryl. When used to substitute, e.g., an alkyl, the phosphoryl group of the phosphorylalkyl may be represented by the general formulas:

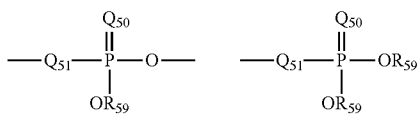

wherein $Q_{50}$ and $R_{59}$, each independently, are defined above, and $Q_{51}$ represents O, S or N. When $Q_{50}$ is S, the phosphoryl moiety is a "phosphorothioate".

The term "phosphoramidite" is art-recognized and may be represented in the general formulas:

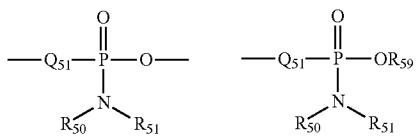

wherein $Q_{51}$, $R_{50}$, $R_{51}$ and $R_{59}$ are as defined above.

The term "phosphonamidite" is art-recognized and may be represented in the general formulas:

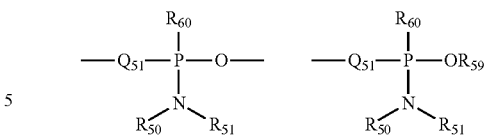

wherein $Q_{51}$, $R_{50}$, $R_{51}$ and $R_{59}$ are as defined above, and $R_{60}$ represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. Exemplary substituents include, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, sulfamoyl, ketone, aldehyde, ester, heterocyclyl, aromatic or heteroaromatic moieties, —CF$_3$, —CN, and the like. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. Substituents themselves can also be further substituted with one or more of the substituents delineated above. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "physiologically acceptable carrier" refers to a carrier in which one or more of the compounds of the invention are dispersed, dissolved, suspended, admixed and physiologically tolerable, i.e., can be administered to, in, or on the subject's body without undue discomfort, or irritation, or toxicity.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

II. SILAXANTHENIUM COMPOUNDS OF THE INVENTION

One aspect of the invention provides a compound represented by Formula I:

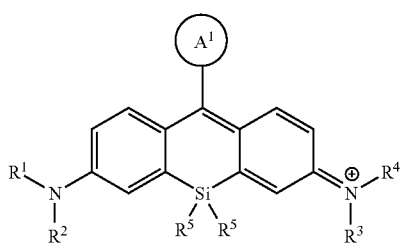

(I)

or a salt thereof, wherein:

$A^1$ is phenyl or a 5-6 membered heteroaryl, each of which is optionally substituted with 1, 2, or 3 substituents independently selected from the group consisting of alkyl, haloalkyl, halogen, hydroxyl, alkoxy, —$CO_2H$, —$CO_2^-$, —$CO_2$-(optionally substituted heterocycloalkyl), —C(O)N($R^6$)($R^7$), —N($R^6$)C(O)($R^7$), alkylene-(optionally substituted heterocyclyl), nitro, alkylene-O-alkylene-$CO_2H$, alkylene-O-alkylene-$CO_2^-$, —$SO_2$—N($R^6$)-alkylene-$CO_2H$, —$SO_2$—N($R^6$)-alkylene-$CO_2^-$, —N($R^6$)—$SO_2$-alkylene-$CO_2H$, —N($R^6$)—$SO_2$-alkylene-$CO_2^-$, —$SO_2$—N($R^6$)-(optionally substituted heterocycloalkyl), —$SO_2$—N($R^6$)$_2$, —$SO_2$—N($R^6$)-alkylene-(optionally substituted heterocyclyl), $X^1$, and alkylene-$X^1$;

$X^1$ represents independently for each occurrence a maleimide, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitro-phenol ester, a fluoro-phenol ester, azide, —NCS, —CHO, —$COCH_2I$, a phosphoramidite, a phthalamido, or a maleimide;

$R^1$ and $R^2$ each represent independently hydrogen, alkyl, cycloalkyl, heterocycloalkyl, or —C(O)N($R^6$)(optionally substituted alkyl); or $R^1$ and $R^2$ are taken together with the nitrogen atom to which they are attached to form a monocyclic or bicyclic ring;

$R^3$ and $R^4$ each represent independently hydrogen, alkyl, cycloalkyl, heterocycloalkyl, or —C(O)N($R^6$)(optionally substituted alkyl); or $R^3$ and $R^4$ are taken together with the nitrogen atom to which they are attached to form a monocyclic or bicyclic ring;

$R^5$ represents independently for each occurrence $C_{1-6}$ alkyl;

$R^6$ represents independently for each occurrence hydrogen or alkyl;

$R^7$ represents independently for each occurrence hydrogen, alkyl, alkylene-$CO_2H$, alkylene-C(O)N($R^6$)$_2$, alkylene-(optionally substituted heterocyclyl), optionally substituted heterocyclyl, alkylene-(optionally substituted heteroaryl), or hydroxyl alkylene-(optionally substituted heterocyclyl); and $R^8$ represents independently for each occurrence hydrogen, alkyl, or aryl.

In some embodiments, the variables delineated in formula (I) can be defined as follows:

$A^1$ is phenyl or a 5-6 membered heteroaryl, each of which is optionally substituted with 1, 2, or 3 substituents independently selected from the group consisting of alkyl, haloalkyl, halogen, hydroxyl, alkoxy, —$CO_2H$, —$CO_2^-$, —$CO_2$-(optionally substituted heterocycloalkyl), —C(O)N($R^6$)($R^7$), —N($R^6$)C(O)($R^7$), alkylene-(optionally substituted heterocyclyl), nitro, alkylene-O-alkylene-$CO_2H$, alkylene-O-alkylene-$CO_2^-$, —$SO_2$—N($R^6$)-alkylene-$CO_2H$, —$SO_2$—N($R^6$)-alkylene-$CO_2^-$, —N($R^6$)—$SO_2$-alkylene-$CO_2H$, —N($R^6$)—$SO_2$-alkylene-$CO_2^-$, —$SO_2$—N($R^6$)-(optionally substituted heterocycloalkyl), —$SO_2$—N($R^6$)$_2$, —$SO_2$—N($R^6$)-alkylene-(optionally substituted heterocyclyl), $X^1$, and alkylene-$X^1$;

$X^1$ represents independently for each occurrence an ester, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitrophenyl ester, a fluorophenyl ester, alkyne, azide, hydrazide, alkoxylamine, —NCS, —CHO, —$COCH_2I$, a phosphoramidite, a phthalamido, or a maleimide;

$R^1$ and $R^2$ each represent independently hydrogen, alkyl, cycloalkyl, heterocycloalkyl, or —C(O)N($R^6$)(optionally substituted alkyl); or $R^1$ and $R^2$ are taken together with the nitrogen atom to which they are attached to form a monocyclic or bicyclic ring;

$R^3$ and $R^4$ each represent independently hydrogen, alkyl, cycloalkyl, heterocycloalkyl, or —C(O)N($R^6$)(optionally substituted alkyl); or $R^3$ and $R^4$ are taken together with the nitrogen atom to which they are attached to form a monocyclic or bicyclic ring;

$R^5$ represents independently for each occurrence $C_{1-6}$ alkyl, optionally bearing a functional group, an ester, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitrophenyl ester, a fluorophenyl ester, alkyne, azide, hydrazide, alkoxylamine, —NCS, —CHO, —$COCH_2I$, a phosphoramidite, a phthalamido, or a maleimide;

$R^6$ represents independently for each occurrence hydrogen or alkyl;

$R^7$ represents independently for each occurrence hydrogen, alkyl, alkylene-$CO_2H$, alkylene-C(O)N($R^6$)$_2$, alkylene-(optionally substituted heterocyclyl), optionally substituted heterocyclyl, alkylene-(optionally substituted heteroaryl), or hydroxyl alkylene-(optionally substituted heterocyclyl); and $R^8$ represents independently for each occurrence hydrogen, alkyl, or aryl.

In certain embodiments, the compound further comprises a counterion having a charge of −1. Exemplary counterions having a charge of −1 include, for example, halide (e.g., Cl⁻, Br⁻, or I⁻) and $RCO_2^-$, where R is alkyl, aryl, aralkyl, and the like.

In certain embodiments, $A^1$ is a 5-6 membered heteroaryl optionally substituted with 1, 2, or 3 substituents independently selected from the group consisting of alkyl, haloalkyl, halogen, hydroxyl, alkoxy, —$CO_2H$, —$CO_2^-$, —$CO_2$-(optionally substituted heterocycloalkyl), —C(O)N($R^6$)($R^7$), —N($R^6$)C(O)($R^7$), alkylene-(optionally substituted heterocyclyl), nitro, alkylene-O-alkylene-$CO_2H$, alkylene-O-alkylene-$CO_2^-$, —$SO_2$—N($R^6$)-alkylene-$CO_2H$, —$SO_2$—N($R^6$)-alkylene-$CO_2^-$, —N($R^6$)—$SO_2$-alkylene-$CO_2H$, —N($R^6$)—$SO_2$-alkylene-$CO_2^-$, —$SO_2$—N($R^6$)-(optionally substituted heterocycloalkyl), —$SO_2$—N($R^6$)$_2$, and —$SO_2$—N($R^6$)-alkylene-(optionally substituted heterocyclyl). In certain embodiments, $A^1$ is thiophenyl, furanyl, or pyridinyl, each of which is optionally substituted with 1, 2, or 3 substituents independently selected from the group consisting of alkyl, haloalkyl, halogen, hydroxyl, alkoxy, —$CO_2H$, —$CO_2^-$, —$CO_2$-(optionally substituted heterocycloalkyl), —$C(O)N(R^6)(R^7)$, —$N(R^6)C(O)(R^7)$, alkylene-(optionally substituted heterocyclyl), nitro, alkylene-O-alkylene-$CO_2H$, alkylene-O-alkylene-$CO_2^-$, —$SO_2$—$N(R^6)$-alkylene-$CO_2H$, —$SO_2$—$N(R^6)$-alkylene-$CO_2^-$, —$N(R^6)$—$SO_2$-alkylene-$CO_2H$, —$N(R^6)$—$SO_2$-alkylene-$CO_2^-$, —$SO_2$—$N(R^6)$-(optionally substituted heterocycloalkyl), —$SO_2$—$N(R^6)_2$, and —$SO_2$—$N(R^6)$-alkylene-(optionally substituted heterocyclyl). In certain embodiments, $A^1$ is phenyl optionally substituted with 1, 2, or 3 substituents independently selected from the group consisting of alkyl, haloalkyl, halogen, hydroxyl, alkoxy, —$CO_2H$, —$CO_2^-$, —$CO_2$-(optionally substituted heterocycloalkyl), —$C(O)N(R^6)(R^7)$, —$N(R^6)C(O)(R^7)$, alkylene-(optionally substituted heterocyclyl), nitro, alkylene-O-alkylene-$CO_2H$, alkylene-O-alkylene-$CO_2^-$, —$SO_2$—$N(R^6)$-alkylene-$CO_2H$, —$SO_2$—$N(R^6)$-alkylene-$CO_2^-$, —$N(R^6)$—$SO_2$-alkylene-$CO_2H$, —$N(R^6)$—$SO_2$-alkylene-$CO_2^-$, —$SO_2$—$N(R^6)$-(optionally substituted heterocycloalkyl), —$SO_2$—$N(R^6)_2$, and —$SO_2$—$N(R^6)$-alkylene-(optionally substituted heterocyclyl).

In certain embodiments, $R^1$ and $R^2$ each represent independently hydrogen or alkyl; or $R^1$ and $R^2$ are taken together with the nitrogen atom to which they are attached to form a 4-6 membered, saturated heterocyclic ring.

In certain embodiments, $R^3$ and $R^4$ each represent independently hydrogen or alkyl; or $R^3$ and $R^4$ are taken together with the nitrogen atom to which they are attached to form a 4-6 membered, saturated heterocyclic ring.

In certain embodiments, $R^5$ is methyl. In certain embodiments, $R^6$ is hydrogen. In certain embodiments, $R^7$ represents independently for each occurrence hydrogen, alkyl, alkylene-$CO_2H$, or alkylene-$C(O)N(R^6)_2$. In certain embodiments, $R^7$ can further include hydroxyl alkylene-(optionally substituted heteroaryl), alkylene-(optionally substituted phenyl), and hydroxyl alkylene-(optionally substituted phenyl).

In certain embodiments, the compound is a compound presented in Table 1 or 2 herein or a pharmaceutically acceptable salt thereof.

In certain embodiments, the compound has an absorption and emission wavelength in the range from about 500 nm to about 1100 nm. In certain embodiments, the compound has an absorption and emission wavelength in the range from about 500 nm to about 600 nm.

One aspect of the invention provides a compound represented by Formula I-A:

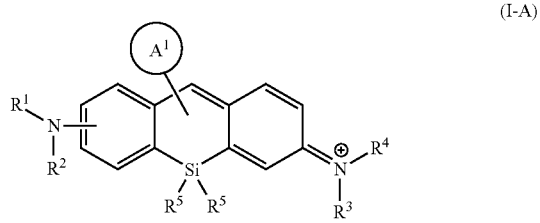

(I-A)

or a salt thereof, wherein:
$A^1$ is phenyl or a 5-6 membered heteroaryl, each of which is optionally substituted with 1, 2, or 3 substituents independently selected from the group consisting of alkyl, haloalkyl, halogen, hydroxyl, alkoxy, —$CO_2H$, —$CO_2^-$, —$CO_2$-(optionally substituted heterocycloalkyl), —$C(O)N(R^6)(R^7)$, —$N(R^6)C(O)(R^7)$, alkylene-(optionally substituted heterocyclyl), nitro, alkylene-O-alkylene-$CO_2H$, alkylene-O-alkylene-$CO_2^-$, —$SO_2$—$N(R^6)$-alkylene-$CO_2H$, —$SO_2$—$N(R^6)$-alkylene-$CO_2^-$, —$N(R^6)$—$SO_2$-alkylene-$CO_2H$, —$N(R^6)$—$SO_2$-alkylene-$CO_2^-$, —$SO_2$—$N(R^6)$-(optionally substituted heterocycloalkyl), —$SO_2$—$N(R^6)_2$, —$SO_2$—$N(R^6)$-alkylene-(optionally substituted heterocyclyl), $X^1$, and alkylene-$X^1$;

$X^1$ represents independently for each occurrence a maleimide, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitro-phenol ester, a fluoro-phenol ester, azide, —NCS, —CHO, —COCH$_2$I, a phosphoramidite, a phthalamido, or a maleimide;

$R^1$ and $R^2$ each represent independently hydrogen, alkyl, cycloalkyl, heterocycloalkyl, or —C(O)N($R^6$)(optionally substituted alkyl); or $R^1$ and $R^2$ are taken together with the nitrogen atom to which they are attached to form a monocyclic or bicyclic ring;

$R^3$ and $R^4$ each represent independently hydrogen, alkyl, cycloalkyl, heterocycloalkyl, or —C(O)N($R^6$)(optionally substituted alkyl); or $R^3$ and $R^4$ are taken together with the nitrogen atom to which they are attached to form a monocyclic or bicyclic ring;

$R^5$ represents independently for each occurrence $C_{1-6}$ alkyl;
$R^6$ represents independently for each occurrence hydrogen or alkyl;
$R^7$ represents independently for each occurrence hydrogen, alkyl, alkylene-$CO_2H$, alkylene-C(O)N($R^6$)$_2$, alkylene-(optionally substituted heterocyclyl), optionally substituted heterocyclyl, alkylene-(optionally substituted heteroaryl), or hydroxyl alkylene-(optionally substituted heterocyclyl); and
$R^8$ represents independently for each occurrence hydrogen, alkyl, or aryl.

In certain embodiments, the compound further comprises a counterion having a charge of −1. Exemplary counterions having a charge of −1 include, for example, halide (e.g., Cl$^-$, Br$^-$, or I$^-$) and $RCO_2^-$, where R is alkyl, aryl, aralkyl, and the like.

Another aspect of the invention provides compounds represented by the general Formula:

$$W^1—(SX)_{Ar}—W^2$$

wherein SX represents a 3,6-diamino-10-silaxanthenium core (including carbon numbering):

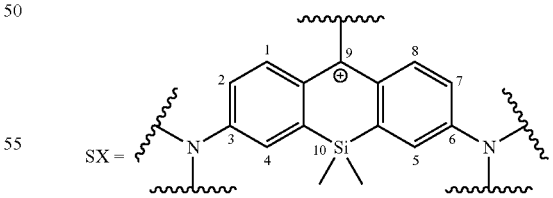

$W^1$ and $W^2$ are, independently, absent, or comprise the same or different carbocyclic or heterocyclic groups linked to the 3- and 6-amino substituents on the SX core wherein the presence or absence of $W^1$ or $W^2$ can alter the optical properties of the fluorochrome. Ar represents a substituted or unsubstituted aryl or heteroaryl substituent in the 9 position of the SX core, wherein the nature of the aryl or heteroaryl group, its orientation and substituents can alter the optical properties of the SX core.

In some embodiments of the invention, Ar is represented by a phenyl, pyridine, furan, thiophene, imidazole, pyrrole, oxazole, isoxazole, benzoxazole thiazole isothiazole, benzthiazole, pyrimidine, pyridazine, triazole. In certain embodiments, Ar is unsubstituted thiophene, e.g., attached to the core at the 2 or 3 position of the thiophene ring.

In some embodiments of the invention, $W^1$ or $W^2$, independently are absent or form, together with the 3- or 6-amino substituents of SX, heterocyclic rings represented by aziridine, azetidine, pyrrolidine, pyrazolidine, piperidine, piperazine, oxazolidine, morpholine or thiomorpholine.

In some embodiments, the substituents attached to the Si atom of the SX core can each be independently selected from $C_{1-6}$ alkyl, optionally bearing a functional group, an ester, a succinimidyl ester, a carboxamide, propargyl, azidoalkyl, isothiocyanate, $-NH_2$, $-OH$, $-SH$, $-SO_3H$, carboxyl, $-C(O)Cl$, $-(CO)O(CO)R^8$, $-CON(H)NH_2$, an acetoxymethyl ester, a substituted or unsubstituted N-hydroxysuccinimidyl ester, a substituted or unsubstituted N-hydroxysulfosuccinimido ester, a nitrophenyl ester, a fluorophenyl ester, alkyne, azide, hydrazide, alkoxylamine, $-NCS$, $-CHO$, $-COCH_2I$, a phosphoramidite, a phthalamido, or a maleimide. For example, the substituents can each be independently selected from unsubstituted $C_{1-6}$ alkyl (e.g. $CH_3$) and $C_{1-6}$ alkyl substituted with carboxyl ($CO_2H$).

Another aspect of the invention provides compounds represented by the general structure:

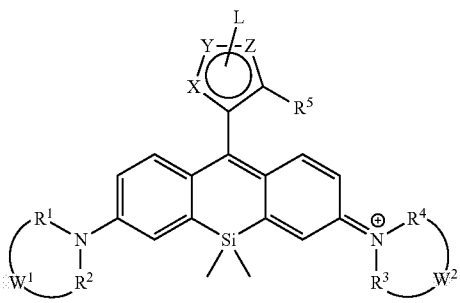

and salts thereof, wherein:
L is absent or is a linker moiety, optionally bearing a functional group or reactive group, such as a carboxylate, carboxyalkyl, maleimide, succinimidyl ester, carboxamide, propargyl, azidoalkyl, isothiocyanate, of $-NH_2$—OH, $-SH$, $-SO_3H$, carboxyl, $-COCl$, $-(CO)O(CO)R^7-$ $CONHNH_2$, acetoxymethyl esters, substituted and unsubstituted N-hydroxysuccinimidyl esters, substituted and unsubstituted N-hydroxysulfosuccinimido esters, nitro- or fluoro or phenol esters, azide, $-NCS$, $-CHO$, azide, $-COCH_2I$, phosphoramidite, phthalamido, or maleimide, wherein $R^7$ is selected from the group consisting of H, alkyl and aryl;
BM is a biomolecule, wherein the fluorescent biomolecule comprises at least one BM.
$R^1$, $R^2$, $R^3$ and $R^4$ are, independently, H, methyl, ethyl, alkyl, or cyclic alkyl, aryl, substituted aryl, heteroaryl, or heterocyclic (e.g. morpholine) alkynyl, carboxyalkyl, aminoalkyl, haloalkyl, azidoalkyl, amide, amino acid, or peptide;
$R^5$ is absent or is H, $C_{1-20}$ alkyl, carboxyl, carboxyalkyl, sulfonate, sulfonamide, halogen, hydroxy, amine, amide, nitro, cyano, O-alkyl, S-alkyl, silyl, O-silyl methyl, ethyl, isopropyl, carboxyalkyl, haloalkyl, alkylsulfhydryl, trifluoromethyl, hydrazide; and
$W^1$ and $W^2$ are, independently, absent or cyclic groups containing aliphatic carbon, nitrogen, oxygen, sulfur, or silicon forming a 4 to 9 membered ring with $R^2$ and $R^3$ or $R^4$ and $R^5$, optionally with further substituents.

X, Y, and Z are, independently, O, S, N, Si, C or (C=C).
It is understood that each of X, Y, and Z, if capable, may bear additional substituents, including but not limited to H, $C_{1-20}$ alkyl, halogen, nitro, O-alkyl, S-alkyl.

One embodiment of the invention consists of exactly one of X, Y or Z being a N, O or S atom, while the other two are C, such that the group Ar, attached to the 9-position of the silaxanthenium core, represents a pyrrolyl, thienyl, furanyl or group with additional substituents. In another embodiment, the position of the heteroatom at X, Y, or Z changes the absorption and emission wavelengths of the resulting fluorochrome compound. In one embodiment, the incorporation of the heteroatom redshifts the absorbance and emission wavelengths of the fluorochrome compound by about 5 to 35 nm. In another embodiment, the absorbance and emission wavelengths of the fluorochrome compound are red shifted by about 10 to 25 nm. Fluorochrome compounds of this type can be represented by the following formulae:

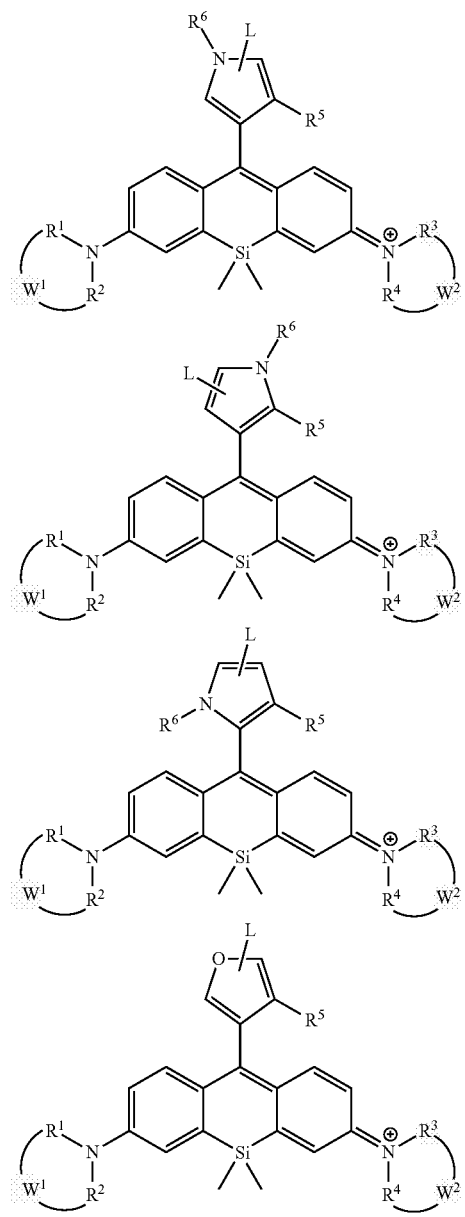

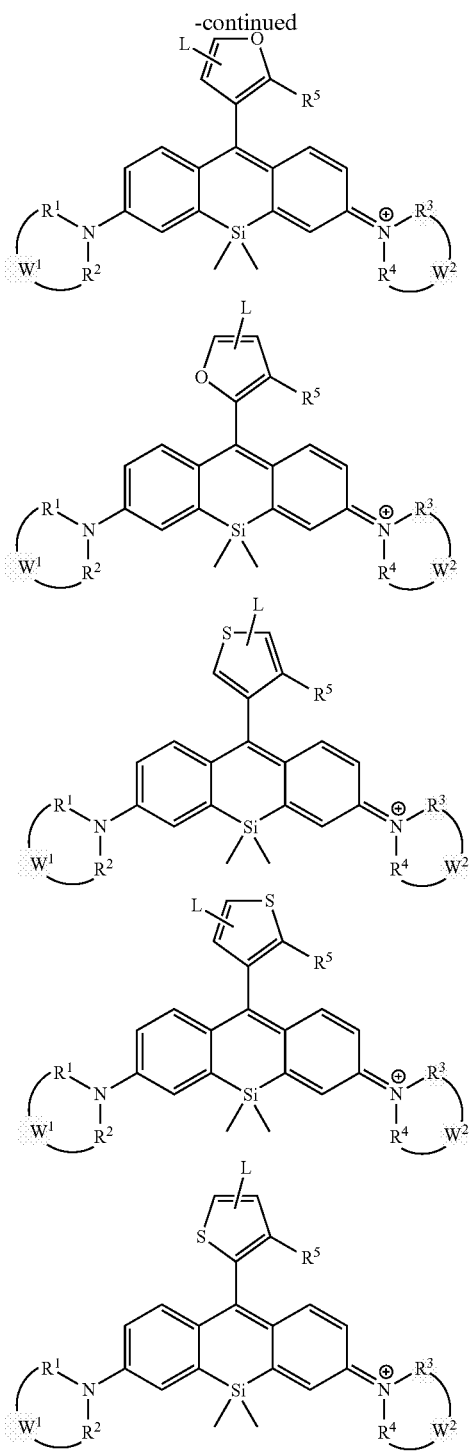

wherein $R^1$, $R^2$, $R^3$, $R^4$, $R^5$, L, $W^1$, $W^2$ are as defined herein and $R^6$ is H, $C_{1-20}$ alkyl, alkylaryl, aryl, alkenyl, alkynyl or L.

In another embodiment, the wavelength of the fluorochrome compound is red shifted by about 15-20 nm by incorporation of a S in the X position, relative to the Y or Z position, with the other two positions being C. This unexpected change in absorption by altering the position of the heteroatom without changing the empirical formula of dye allows for tuning of the fluorescence wavelengths of the fluorochromes of the present invention, for example to better align with detector filter sets and to more easily allow multiplexing with multiple fluorophores of very similar composition.

In another embodiment of the invention, exactly one of X, Y or Z is a nitrogen (N) atom (such as N, O, S, or Si) while the other two are represented by one C and one (C=C), such that the group Ar, attached to the 9-position of the silaxanthenium core, represents a pyridyl group. Fluorochrome compounds of this type can be represented by the following formulae:

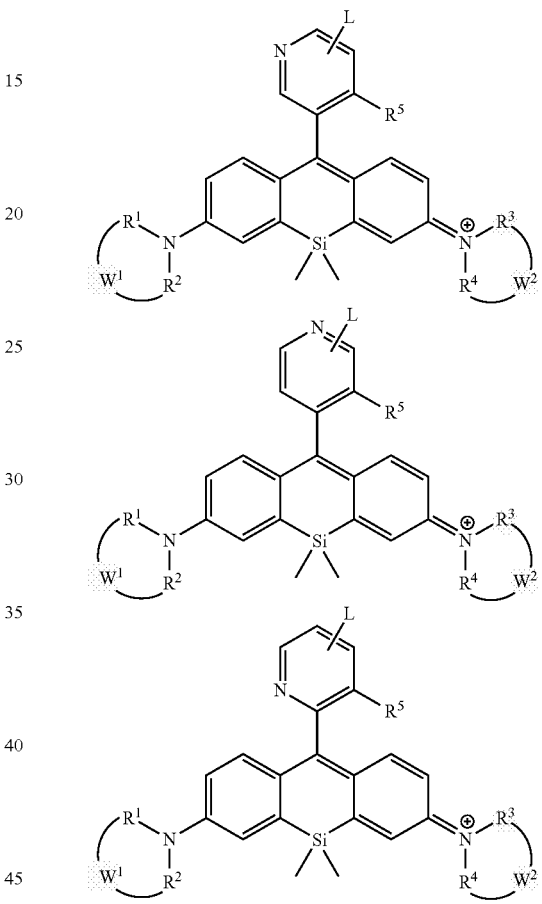

wherein $R^1$, $R^2$, $R^3$, $R^4$, $R^5$, L, $W^1$, $W^2$ are as defined herein.

In other embodiments, X, Y and Z are chosen such that the aryl group in the 9-position of the silaxanthenium core is a oxazole, isoxazole, benzoxazole thiazole isothiazole, benzthiazole, pyrimidine, pyridazine, triazole group, optionally bearing $R^5$ and L.

In other embodiments, L contains a functional group selected from the group consisting of —NH$_2$—OH, —SH, —SO$_3$H, carboxyl, —COCl, —(CO)O(CO)R$^7$— CONHNH$_2$, acetoxymethyl esters, substituted and unsubstituted N-hydroxysuccinimidyl esters, substituted and unsubstituted N-hydroxysulfosuccinimido esters, nitro- or fluoro or phenol esters, azide, —NCS, —CHO, azide, —COCH$_2$I, phosphoramidite, phthalamido, and maleimide, wherein $R^7$ is selected from the group consisting of H, alkyl and aryl.

In another embodiment, the 1, 2, 4, 5, 7, or 8 positions of the 9-silaxanthenium core may be independently substituted, for example by an alkyl, halogen, sulfonate, nitro, cyano, O-alkyl, S-alkyl, amino, carboxylic acid, carboxylic ester, amide, sulfonamide, or hydroxyl group.

It is understood that $W^1$ and $W^2$ may be the same or different. For example, $R^1$—$W^1$—$R^2$ and $R^3$—$W^2$—$R^4$ may be selected from the group consisting of:

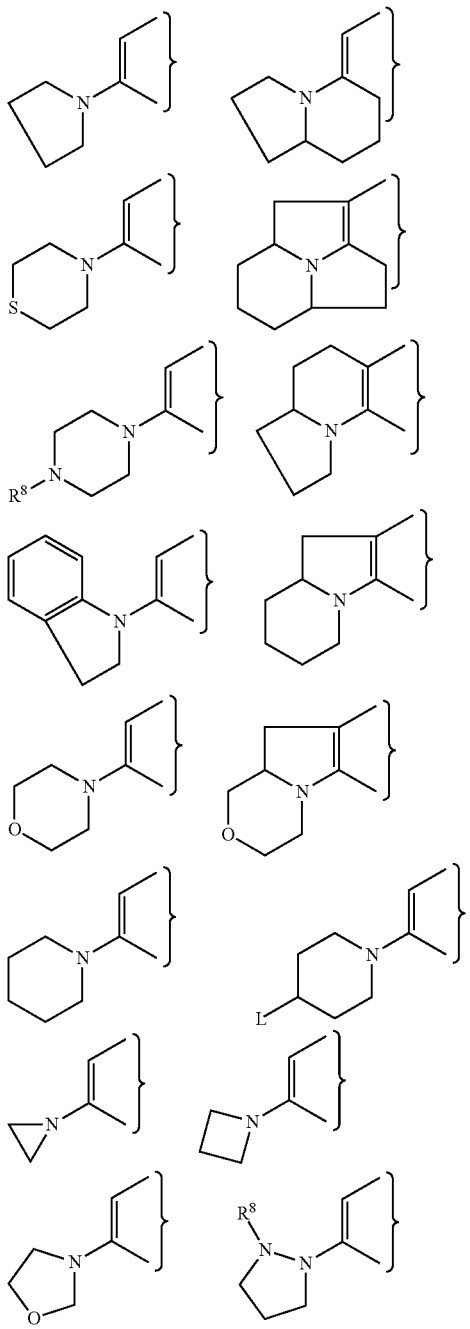

Wherein $R^8$ is H, $C_{1-20}$ alkyl, alkylaryl, aryl, alkenyl, alkynyl and L is a linker moiety, optionally bearing a functional group or reactive group, such as a carboxylate, carboxyalkyl, maleimide, succinimidyl ester, carboxamide, propargyl, azidoalkyl, isothiocyanate, that can be conjugated to a molecule, biomolecule, nanoparticle, etc. Incorporation of one or more non-hydrogen substituents on the carbocyclic or heterocyclic rings can be used to tune the absorption and emission spectrum of the resulting dye.

Generally, the fluorochrome compounds of the present invention can be synthesized in from 4,4'-methylenebis(3-bromoaniline) derivatives. Some examples of the synthesis of 10-silaxanthenes are described in Fu et al.; "A design concept of long-wavelength fluorescent analogs of rhodamine dyes: replacement of oxygen with silicon atom", Chem. Comm. 2008, 1780-1782 and Nagano, et al. "Evolution of Group 14 Rhodamines as Platforms for Near-Infrared Fluorescence Probes Utilizing Photoinduced Electron Transfer", ACS Chem. Biol. 2011, 6, 600-608. First, an N,N-disubstituted 3-bromoaniline, for example 1-(3-bromophenyl)pyrrolidine, is condensed with formaldehyde, to form a bis-(3-bromoaniline) compound which can be purified by silica gel column chromatography. Next, the bromine atoms are reacted with butyllithium followed by treatment with dichlorodimethylsilane to form a 10-silaxanthene core. The 10-silaxanthene is then oxidized with an excess of chloranil in the presence of triethylammonium bicarbonate to form a 10-silaxanthone, which can be reacted with an aryl-lithium reagent such as lithium (2,5-dicarboxylatothiophen-3-yl)lithium, which can be generated in situ by reacting 2,5-dicarboxythiophene with 3 equivalents of butyllithium, followed by an acid workup to give a substituted 3,6-amino-9-aryl-10-silaxanthenium fluorochrome compound as described below:

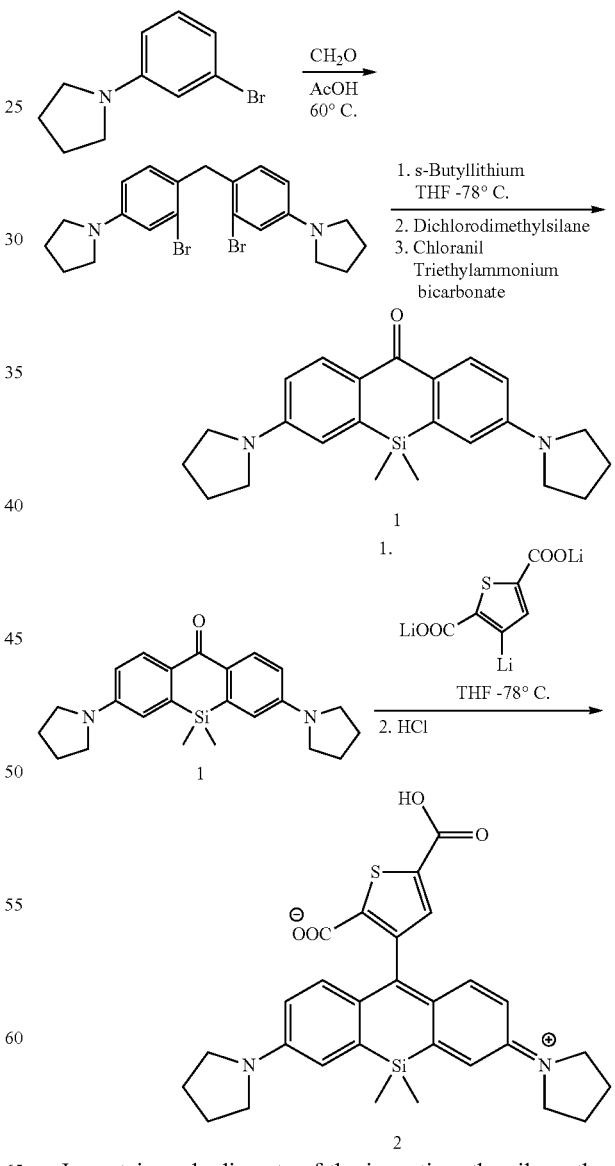

In certain embodiments of the invention, the silaxanthenium fluorochrome compounds are unsymmetrical. Such unsymmetrical xanthenium compounds can be synthesized as follows. One N,N-disubstituted 3-bromoaniline, for example N,N-diallyl-3-bromoaniline, is reacted with a single equivalent of an aldehyde, for example 3-methylthiophene-2-carbaldehyde by heating in hydrochloric acid with $ZnCl_2$. The first condensation is followed by addition of a second N,N-disubstituted 3-bromoaniline, for example N,N-dimethyl-3-bromoaniline to give an unsymmetrical bis-(3-bromoaniline) intermediate which is purified by silica gel column chromatography. The unsymmetrical intermediate is then reacted with butyllithium in THF at −78° C. followed by addition of dichlorodimethylsilane and oxidation with chloranil to give an unsymmetrical 9-aryl-10-silaxanthenium fluorochrome compound as described below.

In other embodiments of the invention, the unsymmetrical fluorochrome compound has one of the nitrogen substituents of the 3,6-diamino-10-silaxanthenium core unsubstituted, i.e. bearing only hydrogen. Such unsymmetrical fluorochrome compounds can be synthesized by the palladium catalyzed deallylation of an unsymmetrical N,N-diallyl-10-silaxanthene fluorochrome in the presence of an allyl scavenger such as N,N'-dimethylbarbituric acid (NDMBA). The N,N-diallyl-10-silaxanthene is prepared in the same manner as the N,N-diallylxanthenium fluorochrome, but the final oxidation step with chloranil is performed after the allyl deprotection as described below.

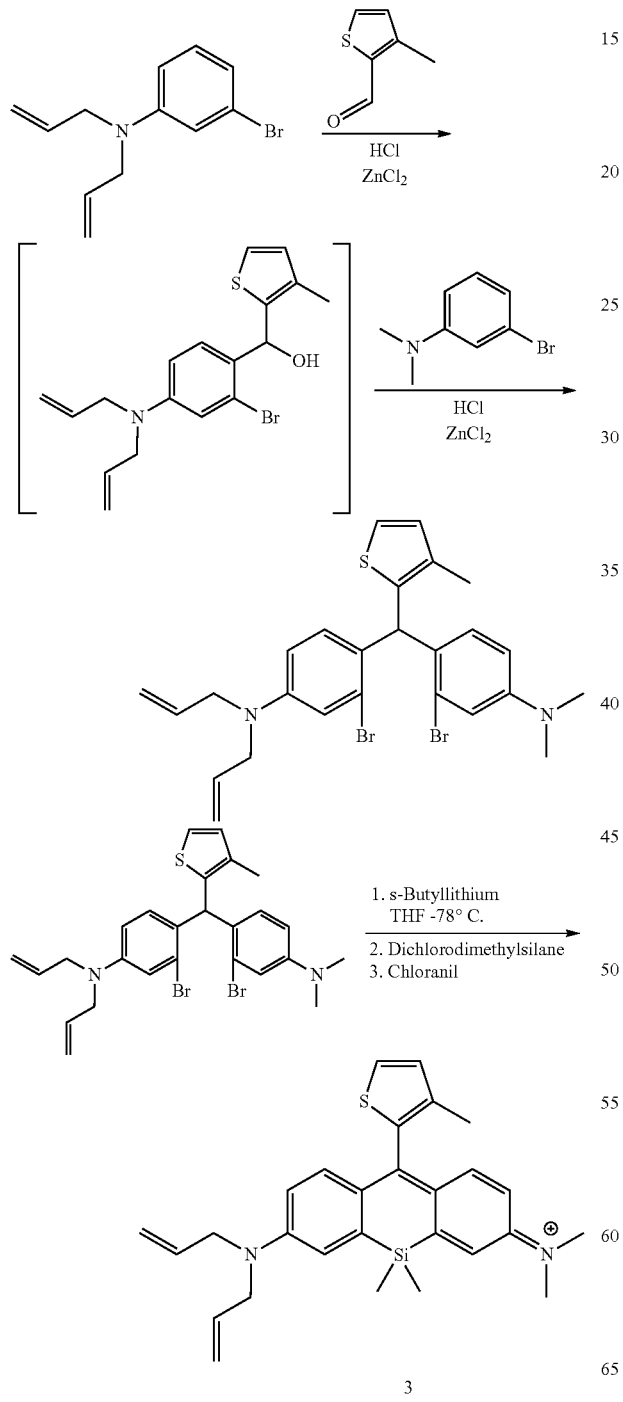

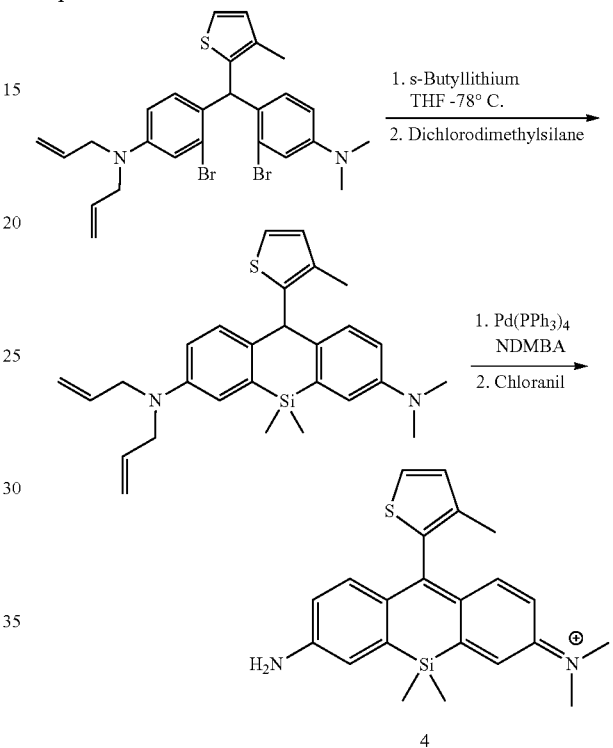

In another aspect of the current invention an unsymmetrical silaxanthenium fluorogenic, if one of the amine substituents is in the form of a nonfluorescent amide with an amino acid or peptide sequence that can be cleaved by an enzyme or protease, for example Z-Leu-Arg. Cleavage of the nonfluorescent amide with an enzyme, such as cathepsin B, K, L, S or V will release a free amine which will result in the release of a fluorescent silaxanthenium fluorochrome. Substituents at the other amine and in the 9-position of the xanthenium core, for example a 3-methylthien-2-yl group can redshift the activated fluorochrome compound relative to compounds that do not contain a heteroaryl group in the 9-position. The synthesis and enzyme activation of such a fluorogenic silaxanthenium probe is described below:

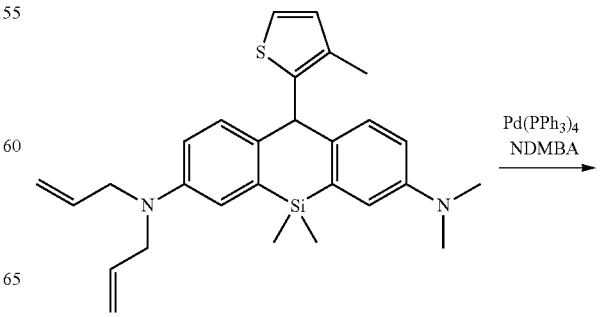

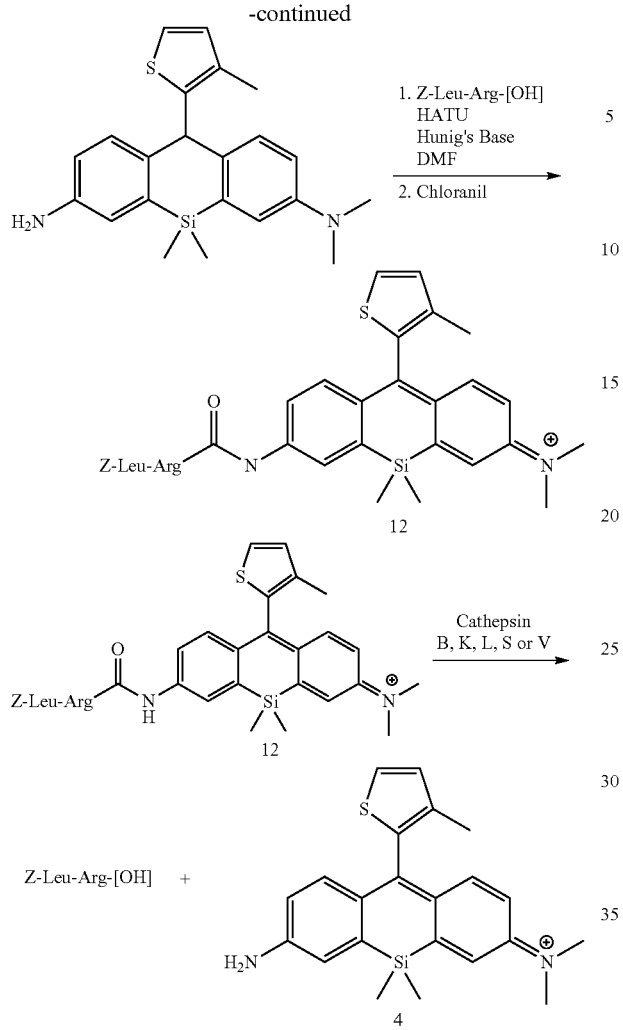

In certain embodiments, the compound comprises a compound presented in Table 1 or a salt thereof. It is appreciated that a counter ion (e.g., a halide, such as Cl⁻) may be present as necessary in order to provide a charge-neutral composition. For example, compound 13 as depicted in Table 1 shows a charge of +1, and therefore it is understood that a counterion, such as Cl⁻, is present to provide a charge-neutral composition.

TABLE 1-continued

| Compound No. | Structure |
|---|---|
| 19 | (structure) |
| 4 | (structure) |
| 20 | (structure) |
| 21 | (structure) |
| 22 | (structure) |
| 23 | (structure) |
| 24 | (structure) |
| 25 | (structure) |
| 26 | (structure) |
| 27 | (structure) |

TABLE 1-continued

| Compound No. | Structure |
| --- | --- |
| 28 | 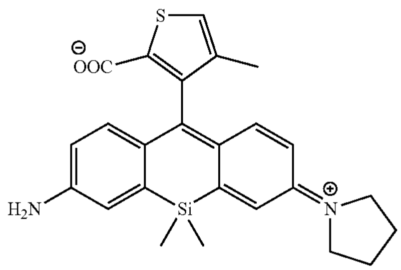 |
| 29 | 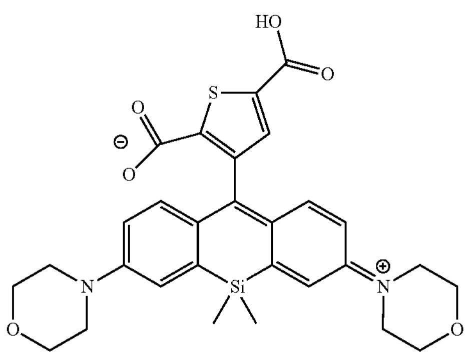 [SMILES: C[Si]1(C)C2=CC(=[N+]3CCOCC3)C=CC2=C(c2cc(C(=O)O)sc2C(=O)O)c2ccc(N3CCOCC3)cc21] |
| 30 | 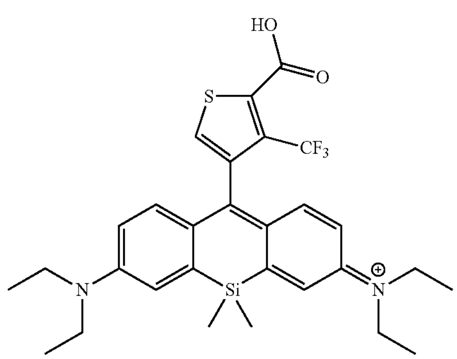 [SMILES: CCN(CC)c1ccc2c(c1)[Si](C)(C)C1=CC(=[N+](CC)CC)C=CC1=C2c1csc(C(=O)O)c1C(F)(F)F] |
| 31 | 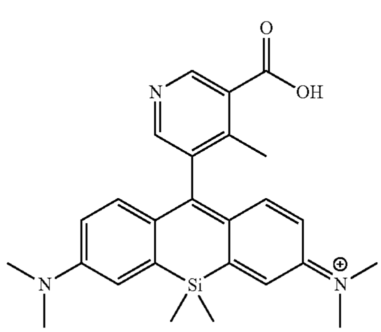 |
| 32 | |
| 33 | |
| 34 | |
| 35 | |

TABLE 1-continued

| Compound No. | Structure |
|---|---|
| 36 | *N-hydroxysuccinimide ester of pyridine-carboxylic acid linked to Si-rhodamine (dimethylamino groups)* |
| 37 | *5-carboxy-pyridine-2-carboxylate linked to Si-rhodamine (dimethylamino groups)* |
| 38 | *NHS ester of propyl-thiophene-carboxylate linked to Si-rhodamine (dimethylamino groups)* |
| 39 | *Furan with CH₂OCH₂COOH substituent linked to Si-rhodamine (dimethylamino groups)* |
| 40 | *Furan-3-carboxylate linked to Si-rhodamine (dimethylamino groups)* |
| 41 | *Furan with butanoic acid and carboxylate substituents linked to Si-rhodamine (dimethylamino groups)* |
| 42 | *5-carboxy-furan-2-carboxylate linked to Si-rhodamine (dimethylamino groups)* |
| 43 | *Methyl furan-carboxylic acid linked to Si-rhodamine (dimethylamino groups)* |
| 44 | *Methyl benzoic acid linked to Si-rhodamine (pyrrolidinyl groups)* |

TABLE 1-continued
| Compound No. | Structure |
|---|---|
| 45 | 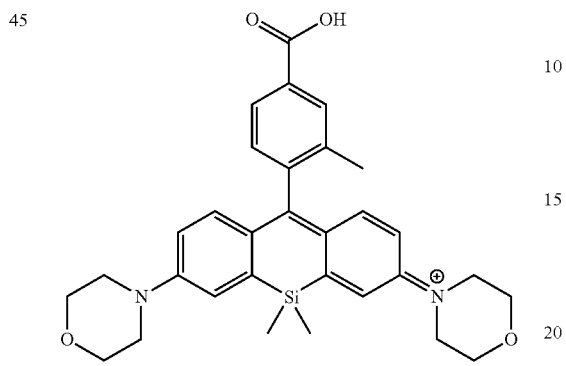 |
| 46 | 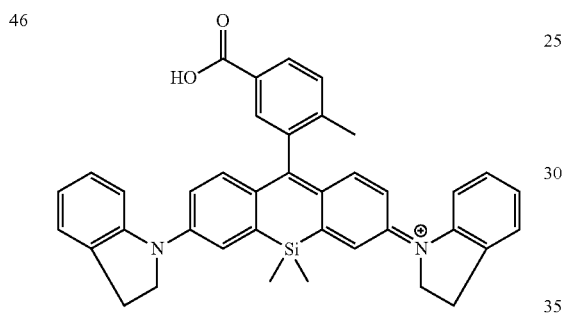 |
| 47 | 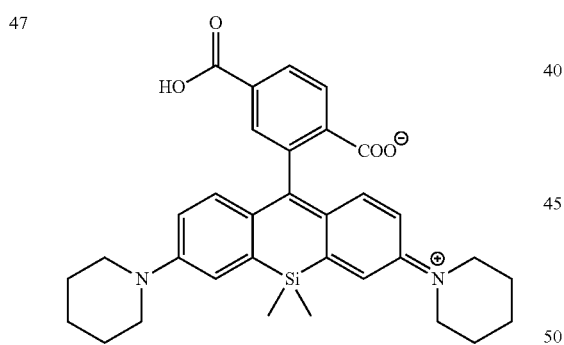 |
| 48 | 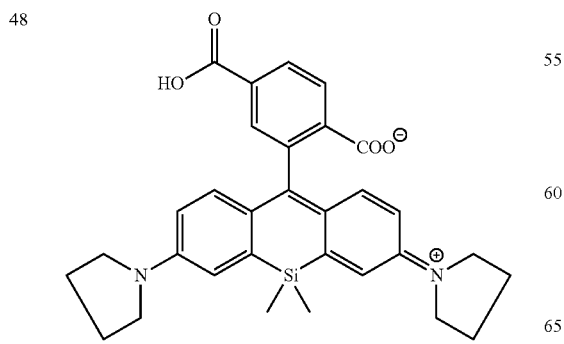 |
| 49 | 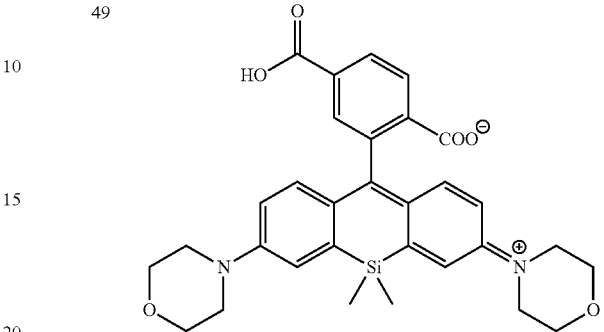 |
| 50 | 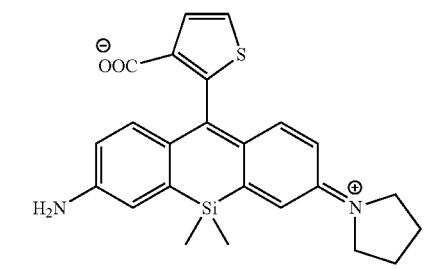 |
| 51 | 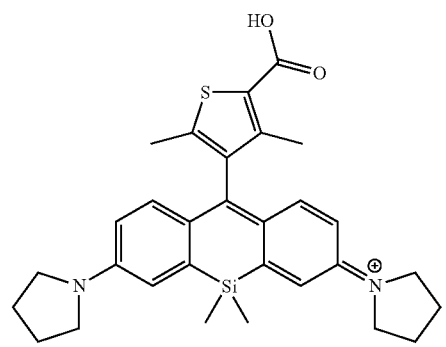 [SMILES: Cc1sc(C(=O)O)c(C)c1C1=C2C=CC(=[N+]3CCCC3)C=C2[Si](C)(C)c2cc(N3CCCC3)ccc21] |
| 52 | 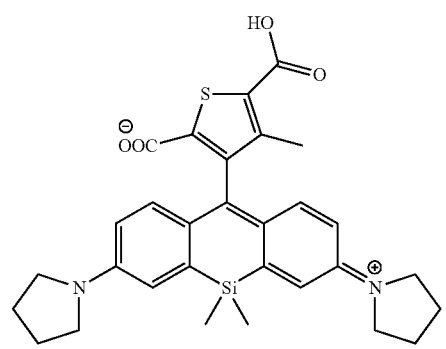 |

TABLE 1-continued

| Compound No. | Structure |
|---|---|
| 53 | *Si-rhodamine with pyrrolidine groups and furan-dicarboxylate substituent* |
| 54 | *Si-rhodamine with dimethylamino groups and 2-nitro-1-methylimidazole substituent* |
| 55 | *Si-rhodamine with dimethylamino groups and 2-nitro-1,5-dimethylimidazole substituent* |
| 56 | *Si-rhodamine with dimethylamino groups and imidazole-propanoic acid substituent* |
| 57 | *Si-rhodamine with dimethylamino groups and 1-methylimidazole-butanoic acid substituent* |
| 58 | *Si-rhodamine with indoline groups and thiophene-carboxylic acid substituent* |
| 59 | *Si-rhodamine with amino and dimethylamino groups and thiophene-carboxylate substituent* |
| 60 | *Si-rhodamine with peptide-amide and dimethylamino groups and thiophene-carboxylate substituent* |

TABLE 1-continued

| Compound No. | Structure |
|---|---|
| 61 | 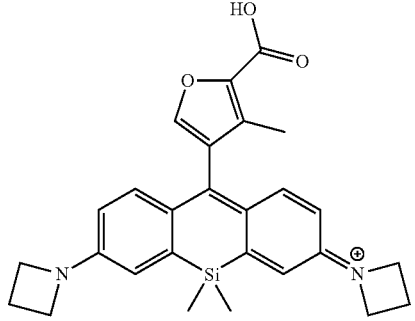 [SMILES: Cc1c(C2=C3C=CC(=[N+]4CCC4)C=C3[Si](C)(C)c3cc(N4CCC4)ccc32)coc1C(=O)O] |
| 62 | 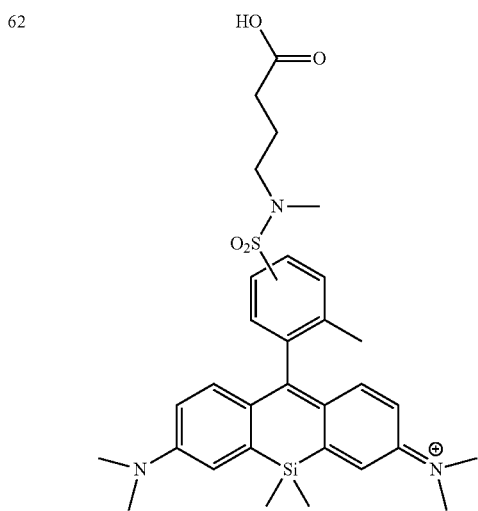 |

TABLE 1-continued

| Compound No. | Structure |
|---|---|
| 63 | 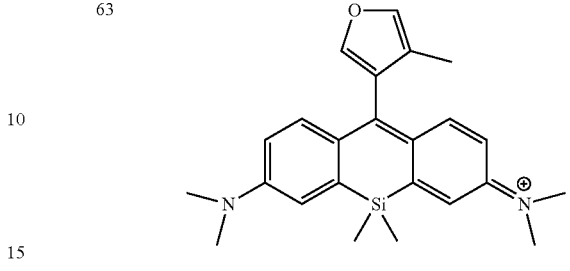 |
| 64 | 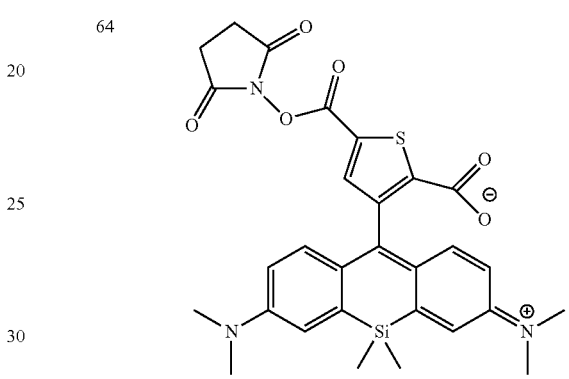 |

In certain preferred embodiments, the compound comprises a compound presented in Table 2 or a salt thereof. It is appreciated that a counter ion (e.g., a halide, such as $Cl^-$) may be present as necessary in order to provide a charge-neutral composition. For example, compound 65 as depicted in Table 2 shows a charge of +1, and therefore it is understood that a counterion, such as $Cl^-$, is present to provide a charge-neutral composition

TABLE 2

| Compound No. | Structure |
|---|---|
| 65 | 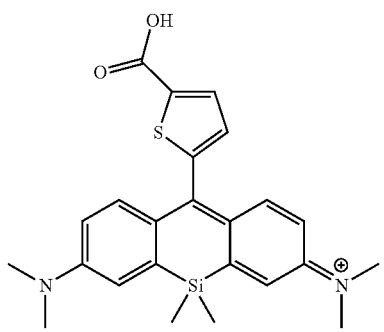 |

TABLE 2-continued
| Compound No. | Structure |
|---|---|
| 22 | 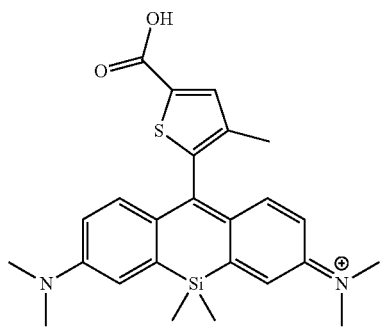 |
| 16 | 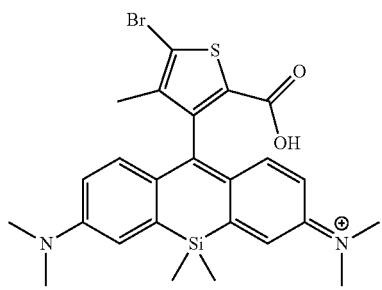 |
| 66 | 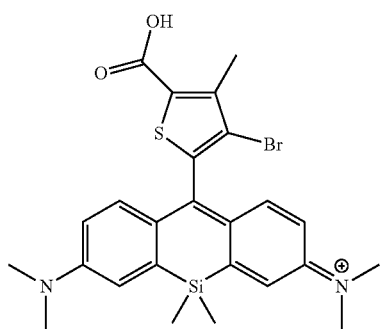 |
| 17 | 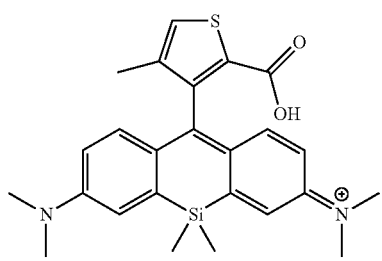 |
| 18 | 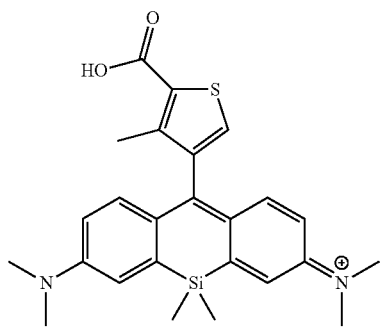 |

TABLE 2-continued

| Compound No. | Structure |
|---|---|
| 20 | (structure) |
| 21 | (structure) |
| 22 | (structure) |
| 44 | (structure) |

TABLE 2-continued

| Compound No. | Structure |
|---|---|
| 45 | 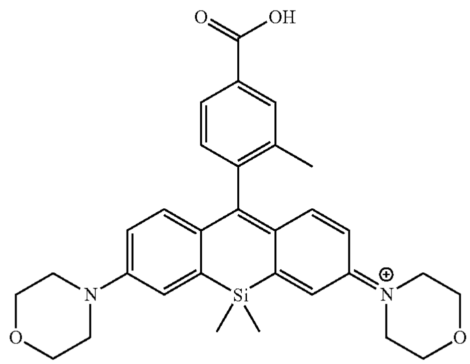 [SMILES: Cc1cc(C(=O)O)ccc1C1=C2C=CC(=[N+]3CCOCC3)C=C2[Si](C)(C)c2cc(N3CCOCC3)ccc21] |
| 46 | 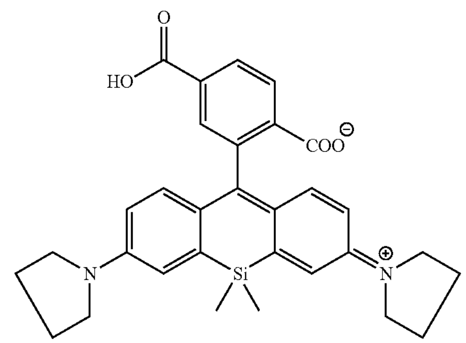 |
| 62 | 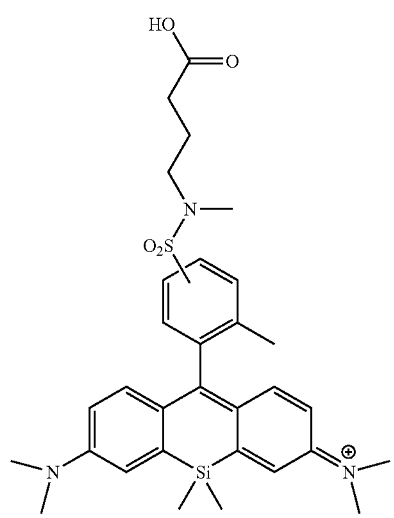 |

TABLE 2-continued
| Compound No. | Structure |
|---|---|
| 67 | 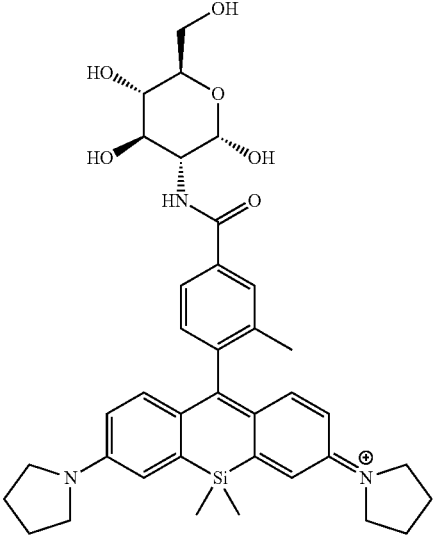 [SMILES: Cc1cc(C(=O)N[C@@H]2[C@@H](O)[C@H](O)[C@@H](CO)O[C@@H]2O)ccc1C1=C2C=CC(=[N+]3CCCC3)C=C2[Si](C)(C)c2cc(N3CCCC3)ccc21] |
| 68 | 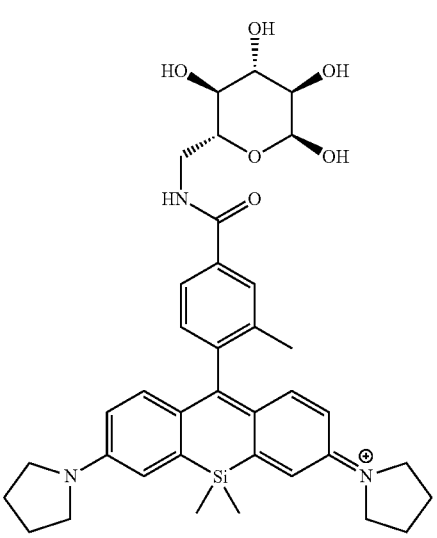 [SMILES: Cc1cc(C(=O)NC[C@H]2O[C@H](O)[C@H](O)[C@@H](O)[C@@H]2O)ccc1C1=C2C=CC(=[N+]3CCCC3)C=C2[Si](C)(C)c2cc(N3CCCC3)ccc21] |
| 69 | 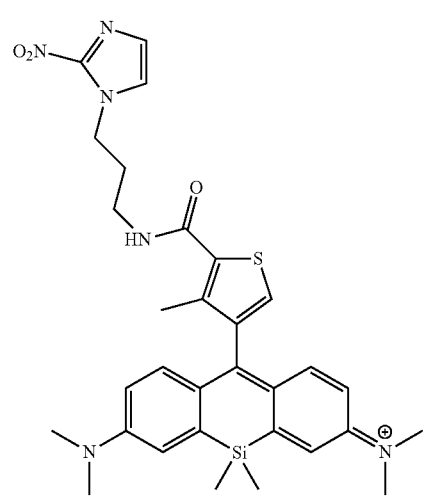 [SMILES: Cc1c(C2=C3C=CC(=[N+](C)C)C=C3[Si](C)(C)c3cc(N(C)C)ccc32)csc1C(=O)NCCCn1ccnc1[N+](=O)[O-]] |

US 9,649,389 B2
47    48
TABLE 2-continued
| Compound No. | Structure |
|---|---|
| 70 | 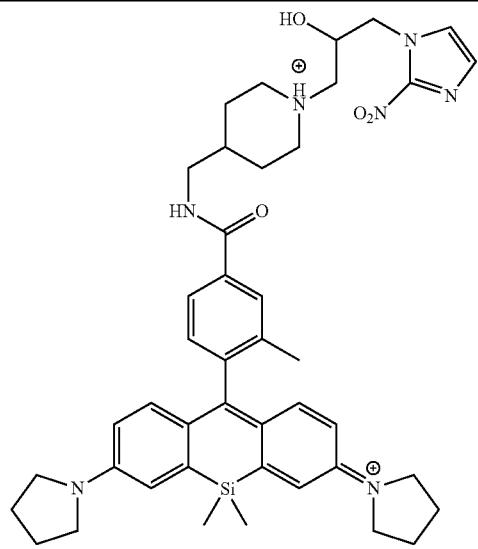 |
| 71 | 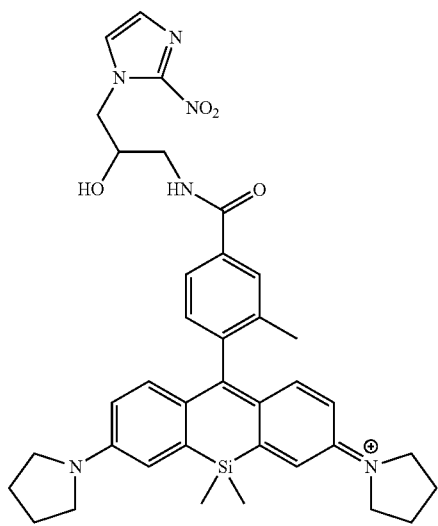 [SMILES: Cc1cc(C(=O)NCC(O)Cn2ccnc2[N+](=O)[O-])ccc1C1=C2C=CC(=[N+]3CCCC3)C=C2[Si](C)(C)c2cc(N3CCCC3)ccc21] |
| 72 | 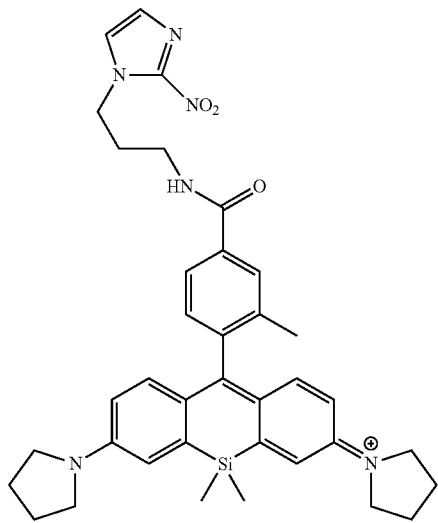 [SMILES: Cc1cc(C(=O)NCCCn2ccnc2[N+](=O)[O-])ccc1C1=C2C=CC(=[N+]3CCCC3)C=C2[Si](C)(C)c2cc(N3CCCC3)ccc21] |

TABLE 2-continued
| Compound No. | Structure |
|---|---|
| 73 | 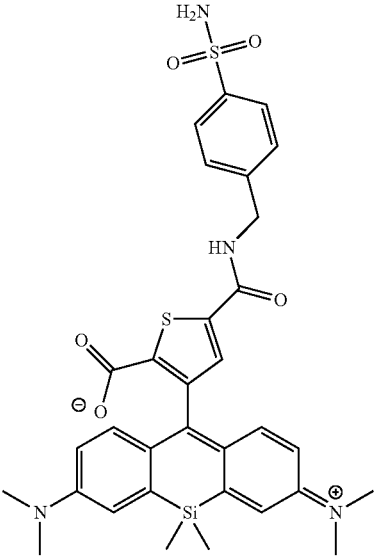 |
| 79 | 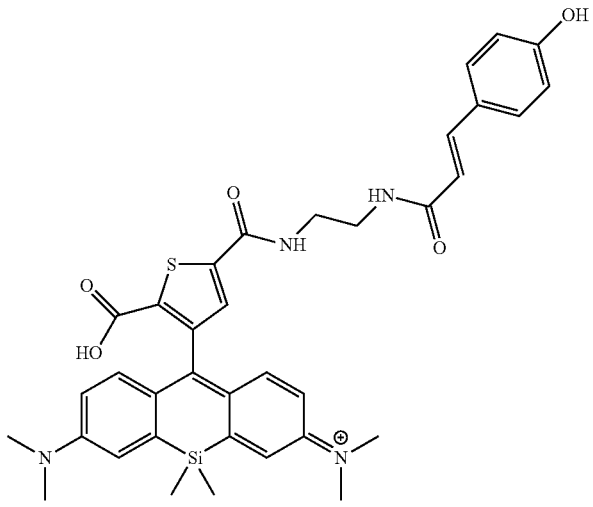 [SMILES: CN(C)c1ccc2c(c1)[Si](C)(C)C1=CC(=[N+](C)C)C=CC1=C2c1cc(C(=O)NCCNC(=O)/C=C/c2ccc(O)cc2)sc1C(=O)O] |
| 80 | 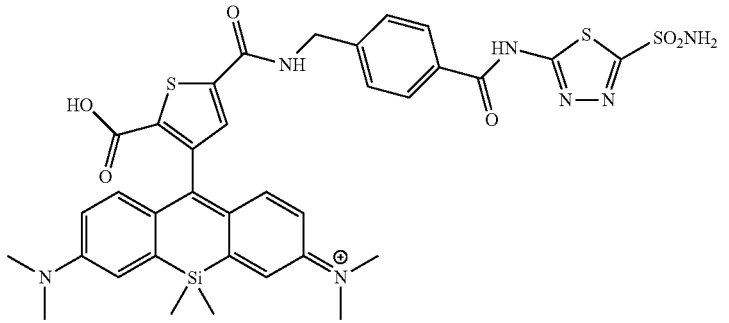 [SMILES: CN(C)c1ccc2c(c1)[Si](C)(C)C1=CC(=[N+](C)C)C=CC1=C2c1cc(C(=O)NCc2ccc(C(=O)Nc3nnc(S(N)(=O)=O)s3)cc2)sc1C(=O)O] |

TABLE 2-continued

| Compound No. | Structure |
|---|---|
| 81 | 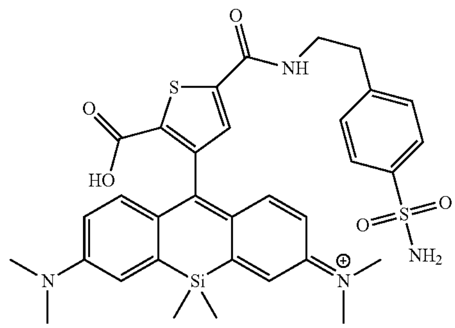 [SMILES: CN(C)c1ccc2c(c1)[Si](C)(C)C1=CC(=[N+](C)C)C=CC1=C2c1cc(C(=O)NCCc2ccc(S(N)(=O)=O)cc2)sc1C(=O)O] |
| 82 | 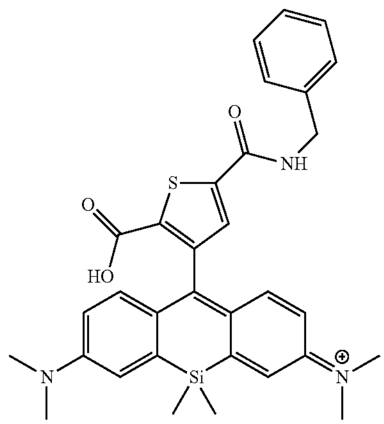 |
| 83 | 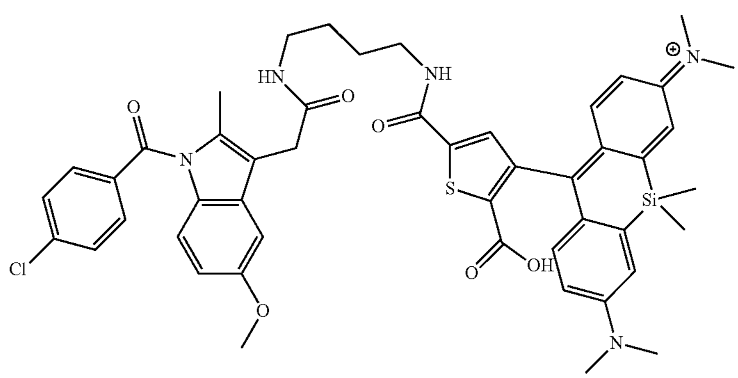 [SMILES: COc1ccc2c(c1)c(CC(=O)NCCCCNC(=O)c1cc(C3=C4C=CC(=[N+](C)C)C=C4[Si](C)(C)c4cc(N(C)C)ccc43)c(C(=O)O)s1)c(C)n2C(=O)c1ccc(Cl)cc1] |
| 84 | 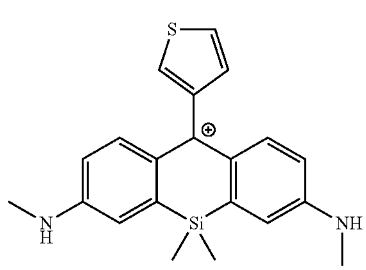 |

TABLE 2-continued
| Compound No. | Structure |
|---|---|
| 85 | 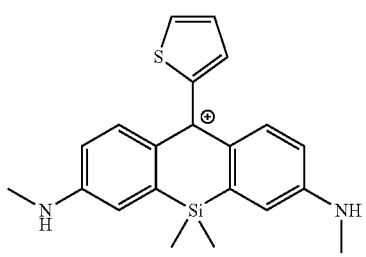 |
| 86 | 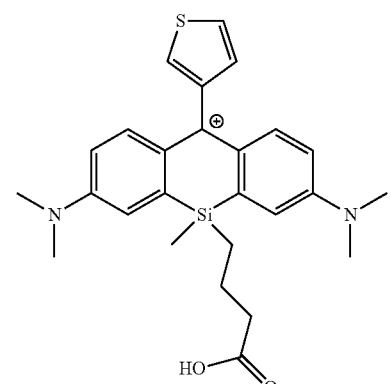 |
| 87 | 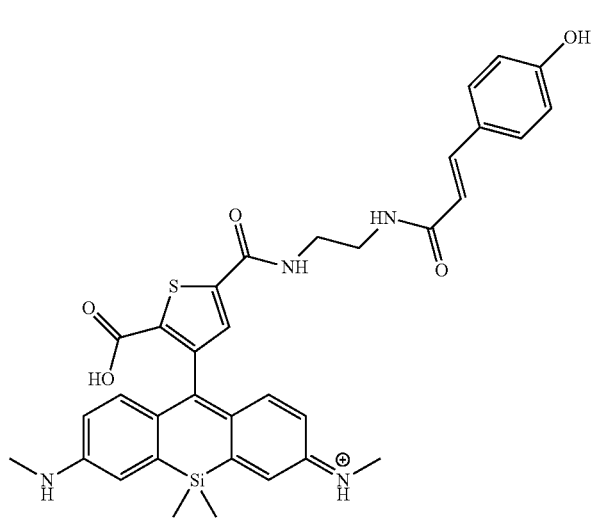 [SMILES: CNc1ccc2c(c1)[Si](C)(C)C1=C/C(=[NH+]/C)C=CC1=C2c1cc(C(=O)NCCNC(=O)/C=C/c2ccc(O)cc2)sc1C(=O)O] |
| 88 | 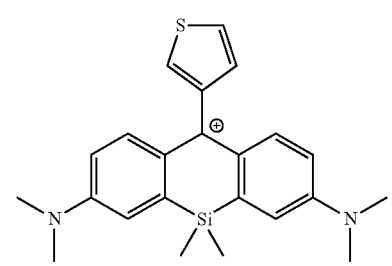 |

TABLE 2-continued
| Compound No. | Structure |
|---|---|
| 89 | 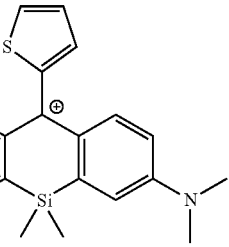 |
| 90 | 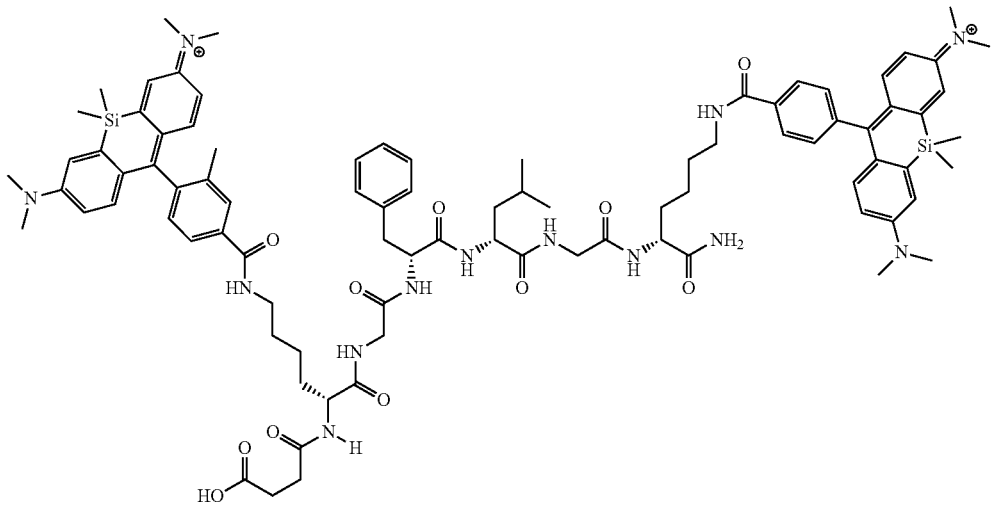 |
| 91 | 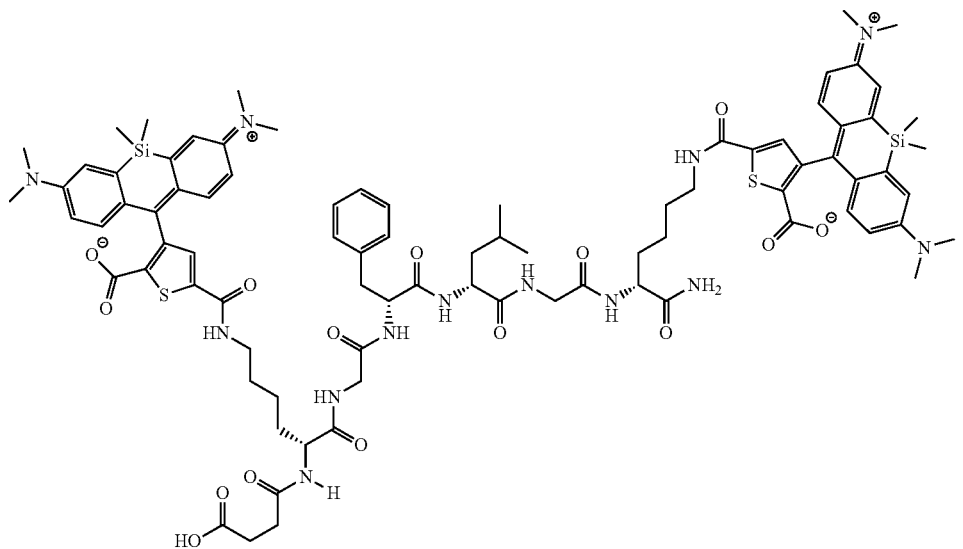 |

TABLE 2-continued

| Compound No. | Structure |
|---|---|
| 92 | 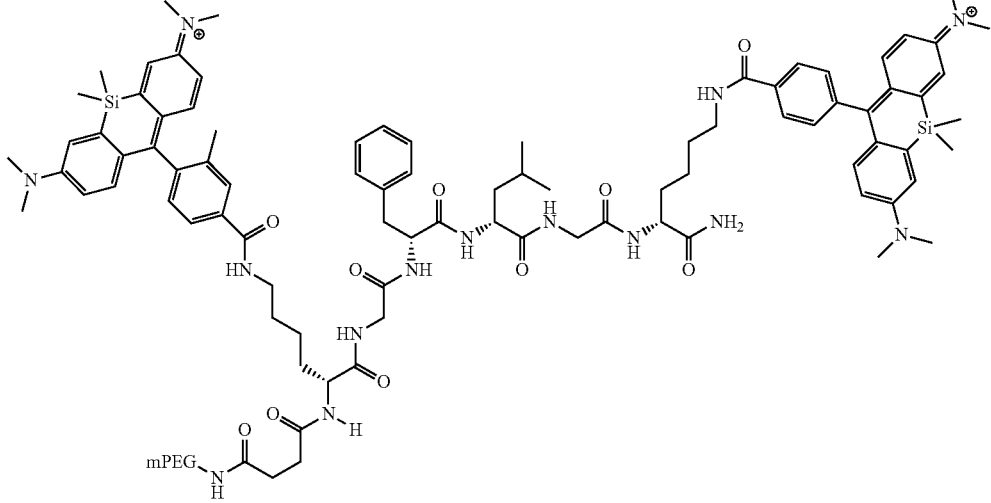 |
| 93 | 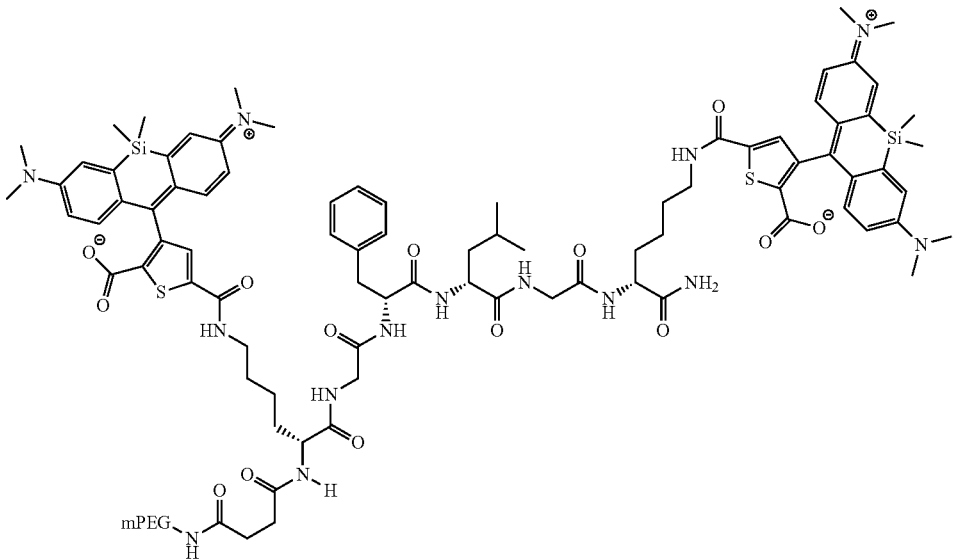 |

Another aspect of the invention provides a conjugate compound formed by reaction of a biological molecule with a compound described herein, such as a compound of Formula I.

Another aspect of the invention provides a conjugate compound that is a compound of Formula I substituted with 1, 2, or 3 groups defined by -L-BM; wherein L is a bond or a linker, -BM is a radical of a biological molecule, and Formula I is represented by:

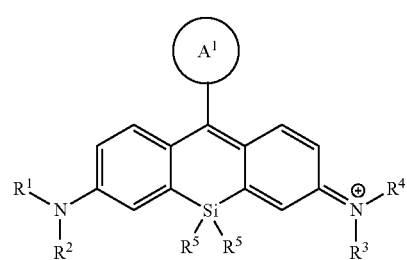

(I)

or a salt thereof, wherein:

$A^1$ is phenyl or a 5-6 membered heteroaryl, each of which is optionally substituted with 1, 2, or 3 substituents independently selected from the group consisting of alkyl, haloalkyl, halogen, hydroxyl, alkoxy, —$CO_2H$, —$CO_2^-$, —$CO_2$-(optionally substituted heterocycloalkyl), —$C(O)N(R^6)(R^7)$, —$N(R^6)C(O)(R^7)$, alkylene-(optionally substituted heterocyclyl), nitro, alkylene-O-alkylene-$CO_2H$, alkylene-O-alkylene-$CO_2^-$, —$SO_2$—$N(R^6)$-alkylene-$CO_2H$, —$SO_2$—$N(R^6)$-alkylene-$CO_2^-$, —$N(R^6)$—$SO_2$-alkylene-$CO_2H$, —$N(R^6)$—$SO_2$-alkylene-$CO_2^-$, —$SO_2$—$N(R^6)$-(optionally substituted heterocycloalkyl), —$SO_2$—$N(R^6)_2$, —$SO_2$—$N(R^6)$-alkylene-(optionally substituted heterocyclyl), $X^1$, and alkylene-$X^1$;

$X^1$ represents independently for each occurrence a maleimide, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitro-phenol ester, a fluoro-phenol ester, azide, —NCS, —CHO, —$COCH_2I$, a phosphoramidite, a phthalamido, or a maleimide;

$R^1$ and $R^2$ each represent independently hydrogen, alkyl, cycloalkyl, heterocycloalkyl, or —$C(O)N(R^6)$(optionally substituted alkyl); or $R^1$ and $R^2$ are taken together with the nitrogen atom to which they are attached to form a monocyclic or bicyclic ring;

$R^3$ and $R^4$ each represent independently hydrogen, alkyl, cycloalkyl, heterocycloalkyl, or —$C(O)N(R^6)$(optionally substituted alkyl); or $R^3$ and $R^4$ are taken together with the nitrogen atom to which they are attached to form a monocyclic or bicyclic ring;

$R^5$ represents independently for each occurrence $C_{1-6}$ alkyl;

$R^6$ represents independently for each occurrence hydrogen or alkyl;

$R^7$ represents independently for each occurrence hydrogen, alkyl, alkylene-$CO_2H$, alkylene-$C(O)N(R^6)_2$, alkylene-(optionally substituted heterocyclyl), optionally substituted heterocyclyl, alkylene-(optionally substituted heteroaryl), or hydroxyl alkylene-(optionally substituted heterocyclyl); and $R^8$ represents independently for each occurrence hydrogen, alkyl, or aryl.

In some embodiments, the variables delineated in formula (I) can be defined as follows:

$A^1$ is phenyl or a 5-6 membered heteroaryl, each of which is optionally substituted with 1, 2, or 3 substituents independently selected from the group consisting of alkyl, haloalkyl, halogen, hydroxyl, alkoxy, —$CO_2H$, —$CO_2^-$, —$CO_2$-(optionally substituted heterocycloalkyl), —$C(O)N(R^6)(R^7)$, —$N(R^6)C(O)(R^7)$, alkylene-(optionally substituted heterocyclyl), nitro, alkylene-O-alkylene-$CO_2H$, alkylene-O-alkylene-$CO_2^-$, —$SO_2$—$N(R^6)$-alkylene-$CO_2H$, —$SO_2$—$N(R^6)$-alkylene-$CO_2^-$, —$N(R^6)$—$SO_2$-alkylene-$CO_2H$, —$N(R^6)$—$SO_2$-alkylene-$CO_2^-$, —$SO_2$—$N(R^6)$-(optionally substituted heterocycloalkyl), —$SO_2$—$N(R^6)_2$, —$SO_2$—$N(R^6)$-alkylene-(optionally substituted heterocyclyl), $X^1$, and alkylene-$X^1$;

$X^1$ represents independently for each occurrence an ester, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitrophenyl ester, a fluorophenyl ester, alkyne, azide, hydrazide, alkoxylamine, —NCS, —CHO, —$COCH_2I$, a phosphoramidite, a phthalamido, or a maleimide;

$R^1$ and $R^2$ each represent independently hydrogen, alkyl, cycloalkyl, heterocycloalkyl, or —$C(O)N(R^6)$(optionally substituted alkyl); or $R^1$ and $R^2$ are taken together with the nitrogen atom to which they are attached to form a monocyclic or bicyclic ring;

$R^3$ and $R^4$ each represent independently hydrogen, alkyl, cycloalkyl, heterocycloalkyl, or —$C(O)N(R^6)$(optionally substituted alkyl); or $R^3$ and $R^4$ are taken together with the nitrogen atom to which they are attached to form a monocyclic or bicyclic ring;

$R^5$ represents independently for each occurrence $C_{1-6}$ alkyl, optionally bearing a functional group, an ester, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitrophenyl ester, a fluorophenyl ester, alkyne, azide, hydrazide, alkoxylamine, —NCS, —CHO, —$COCH_2I$, a phosphoramidite, a phthalamido, or a maleimide;

$R^6$ represents independently for each occurrence hydrogen or alkyl;

$R^7$ represents independently for each occurrence hydrogen, alkyl, alkylene-$CO_2H$, alkylene-$C(O)N(R^6)_2$, alkylene-(optionally substituted heterocyclyl), optionally substituted heterocyclyl, alkylene-(optionally substituted heteroaryl), or hydroxyl alkylene-(optionally substituted heterocyclyl); and $R^8$ represents independently for each occurrence hydrogen, alkyl, or aryl.

In certain embodiments, the compound further comprises a counterion having a charge of −1. Exemplary counterions having a charge of −1 include, for example, halide (e.g., $Cl^-$, $Br^-$, or $I^-$) and $RCO_2^-$, where R is alkyl, aryl, aralkyl, and the like.

In certain embodiments, $R^1$ and $R^2$ each represent independently hydrogen or alkyl; or $R^1$ and $R^2$ are taken together with the nitrogen atom to which they are attached to form a 4-6 membered, saturated heterocyclic ring.

In certain embodiments, $R^3$ and $R^4$ each represent independently hydrogen or alkyl; or $R^3$ and $R^4$ are taken together with the nitrogen atom to which they are attached to form a 4-6 membered, saturated heterocyclic ring.

In certain embodiments, $R^5$ is methyl. In certain embodiments, $R^6$ is hydrogen. In certain embodiments, $R^7$ represents independently for each occurrence hydrogen, alkyl, alkylene-$CO_2H$, or alkylene-$C(O)N(R^6)_2$.

Another aspect of the invention provides a conjugate compound represented by Formula II:

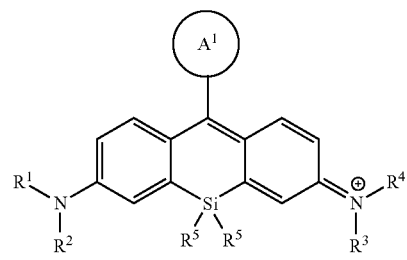

(II)

or a salt thereof, wherein:

$A^1$ is phenyl or a 5-6 membered heteroaryl, each of which is optionally substituted with 1, 2, or 3 substituents independently selected from the group consisting of —C(O)-ψ, —C(O)N($R^6$)-ψ, alkylene-C(O)-ψ, alkylene-C(O)N($R^6$)-ψ, —N($R^6$)C(O)-ψ, alkylene-C(O)-ψ, alkylene-N($R^6$)C(O)-ψ, alkyl, haloalkyl, halogen, hydroxyl, alkoxy, —$CO_2H$, —$CO_2^-$, —$CO_2$— (optionally substituted heterocycloalkyl), —C(O)N($R^6$)($R^7$), —N($R^6$)C(O)($R^7$), alkylene-(optionally substituted heterocyclyl), nitro, alkylene-O-alkylene-$CO_2H$, alkylene-O-alkylene-$CO_2^-$, —$SO_2$—N($R^6$)-alkylene-$CO_2H$, —$SO_2$—N($R^6$)-alkylene-$CO_2^-$, —N($R^6$)—$SO_2$-alkylene-$CO_2H$, N($R^6$)—$SO_2$-alkylene-$CO_2^-$, —$SO_2$—N($R^6$)-(optionally substituted heterocycloalkyl), —$SO_2$—N($R^6$)$_2$, and —$SO_2$—N($R^6$)-(alkylene-(optionally substituted heterocyclyl);

Ψ is a radical of a biological molecule;

$R^1$ and $R^2$ each represent independently hydrogen, alkyl, cycloalkyl, heterocycloalkyl, or —C(O)N($R^6$)(optionally substituted alkyl); or $R^1$ and $R^2$ are taken together with the nitrogen atom to which they are attached to form a monocyclic or bicyclic ring;

$R^3$ and $R^4$ each represent independently hydrogen, alkyl, cycloalkyl, heterocycloalkyl, or —C(O)N($R^6$)(optionally substituted alkyl); or $R^3$ and $R^4$ are taken together with the nitrogen atom to which they are attached to form a monocyclic or bicyclic ring;

$R^5$ represents independently for each occurrence $C_{1-6}$ alkyl;

$R^6$ represents independently for each occurrence hydrogen or alkyl; and $R^7$ represents independently for each occurrence hydrogen, alkyl, alkylene-$CO_2H$, alkylene-C(O)N($R^6$)$_2$, alkylene-(optionally substituted heterocyclyl), optionally substituted heterocyclyl, alkylene-(optionally substituted heteroaryl), or hydroxyl alkylene-(optionally substituted heterocyclyl).

In some embodiments, the variables delineated in formula (II) can be defined as follows:

$A^1$ is phenyl or a 5-6 membered heteroaryl, each of which is optionally substituted with 1, 2, or 3 substituents independently selected from the group consisting of —C(O)-ψ, —C(O)N($R^6$)-ψ, alkylene-C(O)-ψ, alkylene-C(O)N($R^6$)-ψ, —N($R^6$)C(O)-ψ, alkylene-C(O)-ψ, alkylene-N($R^6$)C(O)-ψ, alkyl, haloalkyl, halogen, hydroxyl, alkoxy, —$CO_2H$, —$CO_2^-$, —$CO_2$— (optionally substituted heterocycloalkyl), —C(O)N($R^6$)($R^7$), —N($R^6$)C(O)($R^7$), alkylene-(optionally substituted heterocyclyl), nitro, alkylene-O-alkylene-$CO_2H$, alkylene-O-alkylene-$CO_2^-$, —$SO_2$—N($R^6$)-alkylene-$CO_2H$, —$SO_2$—N($R^6$)-alkylene-$CO_2^-$, —N($R^6$)—$SO_2$-alkylene-$CO_2H$, N($R^6$)—$SO_2$-alkylene-$CO_2^-$, —$SO_2$—N($R^6$)-(optionally substituted heterocycloalkyl), —$SO_2$—N($R^6$)$_2$, and —$SO_2$—N($R^6$)-(alkylene-(optionally substituted heterocyclyl);

Ψ is a radical of a biological molecule;

$R^1$ and $R^2$ each represent independently hydrogen, alkyl, cycloalkyl, heterocycloalkyl, or —C(O)N($R^6$)(optionally substituted alkyl); or $R^1$ and $R^2$ are taken together with the nitrogen atom to which they are attached to form a monocyclic or bicyclic ring;

$R^3$ and $R^4$ each represent independently hydrogen, alkyl, cycloalkyl, heterocycloalkyl, or —C(O)N($R^6$)(optionally substituted alkyl); or $R^3$ and $R^4$ are taken together with the nitrogen atom to which they are attached to form a monocyclic or bicyclic ring;

$R^5$ represents independently for each occurrence $C_{1-6}$ alkyl, optionally bearing a functional group, an ester, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitrophenyl ester, a fluorophenyl ester, alkyne, azide, hydrazide, alkoxylamine, —NCS, —CHO, —$COCH_2I$, a phosphoramidite, a phthalamido, or a maleimide;

$R^6$ represents independently for each occurrence hydrogen or alkyl; and $R^7$ represents independently for each occurrence hydrogen, alkyl, alkylene-$CO_2H$, alkylene-C(O)N($R^6$)$_2$, alkylene-(optionally substituted heterocyclyl), optionally substituted heterocyclyl, alkylene-(optionally substituted heteroaryl), or hydroxyl alkylene-(optionally substituted heterocyclyl).

In certain embodiments, the compound further comprises a counterion having a charge of −1. Exemplary counterions having a charge of −1 include, for example, halide (e.g., Cl−, Br−, or I−) and $RCO_2^-$, where R is alkyl, aryl, aralkyl, and the like.

In certain embodiments, $R^1$ and $R^2$ each represent independently hydrogen or alkyl; or $R^1$ and $R^2$ are taken together with the nitrogen atom to which they are attached to form a 4-6 membered, saturated heterocyclic ring.

In certain embodiments, $R^3$ and $R^4$ each represent independently hydrogen or alkyl; or $R^3$ and $R^4$ are taken together with the nitrogen atom to which they are attached to form a 4-6 membered, saturated heterocyclic ring.

In certain embodiments, $R^5$ is methyl. In certain embodiments, $R^6$ is hydrogen. In certain embodiments, $R^7$ represents independently for each occurrence hydrogen, alkyl, alkylene-$CO_2H$, or alkylene-C(O)N($R^6$)$_2$.

In certain embodiments, the biological molecule is a polypeptide, nucleic acid, or a cell.

Another aspect of the current invention comprises a peptide, protein or other biomolecule that presents a proteolytic or enzymolytic scissile bond, and two or more fluorochrome compounds of the present invention that are chemically linked to the peptide, protein or biomolecule such that their fluorescence is significantly quenched. Upon the action of an enzyme by e.g. enzymatic cleavage upon the peptide, protein or biomolecule scissile bond, the fluorochrome compounds are separated and the agent emits a fluorescent signal when excited by electromagnetic radiation of appropriate wavelength and frequency. As used herein, the term "quenched" is understood to mean the process of partially or completely reducing the fluorescent signal from a fluorophore. For example, a fluorescent signal from the fluorochrome compounds of the present invention can be reduced inter- or intra-molecularly through the placement of a second fluorochrome (either the same or a different compound) in close proximity to the first fluorochrome or the placement of a non-fluorogenic quenching chromophore molecule, e.g., quencher, in close proximity to the first fluorophore. The agent is de-quenched (or activated), for example, through the enzymatic cleavage of a peptide, protein or biomolecule proteolytic or enzymolytic scissile bond. In some embodiments, one or more of the fluorochrome compounds of the present invention are linked to a biomolecule (e.g., a peptide) through the cyclic moiety that is attached to the 9-position of the 3,6-diamino-10-silaxanthenium core (e.g., A1 in formula (I) or (II)). See, e.g., compounds 90-93 described herein.

In other embodiments, the fluorochrome compounds of the invention may have very low intrinsic fluorescence (quantum yield) but retain high absorption in the far-red to NIR region of the electromagnetic spectrum. It is contemplated that such fluorochrome compounds could be used as quencher compounds when in close proximity to another fluorescent compound that emits fluorescence at wavelengths close to the absorption wavelengths. Such compounds, containing one fluorescent compound and a complementary quencher compound of the present invention with low intrinsic fluorescence could be activatable if, for example, the fluorescent compound and the quencher compound are separated by a peptide, protein or biomolecule enzymolytic scissile bond that is recognized and cleaved by a particular enzyme or protease. It is further contemplated that the intramolecularly quenched fluorochrome and quencher compounds of the current invention could be activated through chemical means as well, such as an oxidation or reduction with or without the aid of an enzyme.

In certain embodiments, the compounds of the invention can be chemically linked through L to a biological molecule or biomolecule (BM). The resulting fluorochrome-biomolecule conjugate can have a high binding affinity to a target, for example, due to an interaction between the biological molecule and the target, for example, via a receptor-ligand interaction, enzyme-substrate interaction, an antibody-antigen interaction or the like. Such chemically linked compounds, of the general formula [W$^1$—(SX)$_{Ar}$—W$^2$]-L-BM can be represented as:

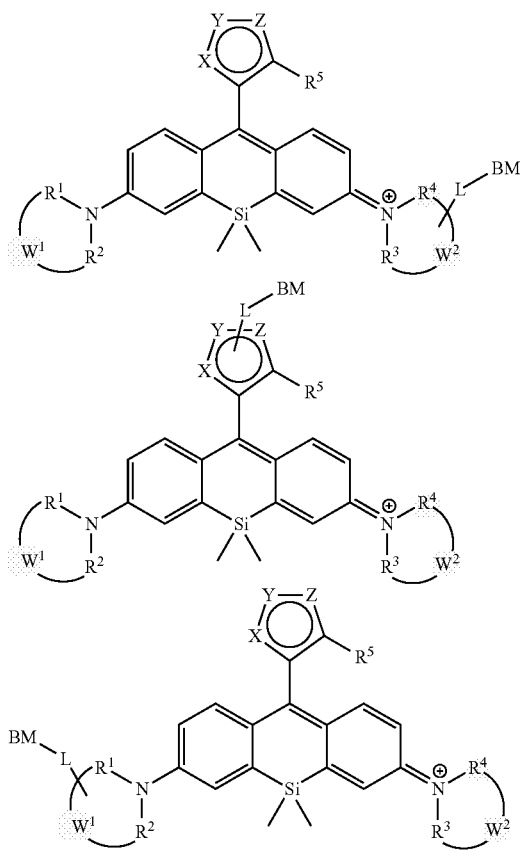

wherein, R$^1$, R$^2$, R$^3$, R$^4$, R$^5$, L, W$^1$, W$^2$, X, Y, and Z are as defined herein, and BM is a biomolecule. The foregoing structures are exemplary and it is understood that a biomolecule (BM) can be chemically linked directly or through a linker L to such compound via any one or more of the groups identified as R$^1$, R$^2$, R$^3$, R$^4$, R$^5$, L, W$^1$, W$^2$, X, Y, and Z.

Another embodiment of the invention is a 9-thienyl-3,6-diamino-10-silaxanthenium or salt thereof, which has optional substituents on the two amino groups (such as methyl, ethyl, or carbocyclic groups) and on the thienyl group (such as a methyl and a carboxylate). Incorporation of a silicon atom at the 10 position causes an approximately 100 nm red shift relative to 10-oxoxanthene dyes, and the substituents at the 9 position and the 3- and 6-amino groups can further improve the optical properties of the dye by shifting the wavelength of absorption or emission or by increasing the quantum yield. Various combinations of substituents can be used to "tune" the properties of the dye for a particular purpose (e.g. to match a given filter set on a microscope or to increase overall brightness). Additionally, functional handles can be incorporated into the dyes for linking to targeting ligands or biomolecules, for example by linking to the thienyl group. Two representative molecules in the first class of dyes that has been synthesized is 3,6-bis-(dimethylamino)-9-(3-methyl-5-carboxy-thien-2-yl)-10,10-dimethyl-10-silaxanthen-9-ium and 3,6-bis(dimethylamino)-9-(2-carboxy-3-methyl-thien-4-yl)-10,10-dimethyl-10-silaxanthenium or salts thereof. An unexpected observation of this class of molecules is that the position of attachment of the thienyl group to the xanthenium core has a drastic effect on the absorption wavelength maximum. For example, when the thienyl group is attached to the xanthenium core at the 2 or 5 position of the thienyl group, the wavelength of maximum absorption is red-shifted by 20-25 nm relative to attachment through the 3 or 4 position. Other substituents also have an impact on the optical properties, for example a methyl substituent adjacent to the silaxanthenium core results in an 8-fold increase in the quantum yield. A series of six 9-thienyl-10-silaxanthenium dyes has been synthesized demonstrating the differences in optical properties.

An embodiment of the invention comprises a 9-substituted-3,6-diamino-10-silaxanthen-9-ium core with carbocyclic, heterocyclic or bicyclic substituents on the amines in the 3 and 6 positions forming, for example, an aziridine, azetidine, pyrrolidine, pyrazolidine, piperidine, piperazine, oxazolidine, morpholine or thiomorpholine. Such cyclic substituents can alter the optical properties or solubility properties of the dye. For example, a cyclic pyrrole group gives the dye a higher quantum yield than the equivalent dye bearing only methyl substituents. As another example, the solubility properties in some solvents including water are enhanced with a morpholine substituent. The cyclic amine substituents can also be polycyclic being fused to a second ring or fused to the silaxanthenium core of the dye through the 2, 4, 5, or 7 position of the silaxanthenium. Polycyclic configurations may alter the dye properties, such as the wavelength of absorption and emission and the quantum yield. The dyes can be symmetrical or unsymmetrical with respect to the cyclic groups on the nitrogens at the 3 and 6 positions or one of the nitrogens may not have a cyclic group. Exemplary N-cyclic silaxanthenium fluorochrome compounds that have been synthesized are 3,6-bis-(pyrrolidin-1-yl)-9-(2-methyl-4-carboxyphenyl)-10,10-dimethyl-10-silaxanthen-9-ium and salts thereof and 3,6-bis-(pyrrolidin-1-yl)-9-(3-methyl-5-carboxy-thien-2-yl)-10,10-dimethyl-10-silaxanthen-9-ium and salts thereof.

The current invention also provides methods for the synthesis of key intermediates (10-silaxanthones) which greatly improve yield and time by removing a difficult purification step and reducing reaction times used in literature syntheses of xanthones. The new procedure allows direct synthesis of 10-silaxanthones from bis-3-bromoanilines without having to isolate a pyronine intermediate.

In another aspect of the current invention, the compounds can also be made to be fluorogenic, if one of the amine substituents is in the form of a nonfluorescent amide with, for example, an amino acid or peptide sequence that can be cleaved by an enzyme. Cleavage of the non-fluorescent amide will release a free amine which will become fluorescent. Substituents at the other amine and in the 9-position of the xanthenium core are chosen to ensure redshifting of the activated fluorophore into the far red/NIR region (greater than about 635 nm).

In some embodiments of the invention, the fluorochrome compounds or conjugates thereof are highly permeable to cell membranes. In other embodiments, the compounds or conjugates are tens, hundreds or thousands of times more permeable than common indocyanine dyes that absorb and emit at comparable wavelengths, as quantified by flow cytometry. In other embodiments, the fluorochrome compounds or conjugates thereof are capable of localizing in specific regions inside cells, such as mitochondria or the nucleus and can be imaged, for example, by fluorescence microscopy. In other embodiments, the fluorochrome compounds or conjugates thereof bind to specific intracellular markers, receptors or proteins. In other embodiments, imaging binding of the compounds or conjugates to intracellular markers, receptors or proteins is indicative of a disease or a state of the cell, e.g. cancer or hypoxia. In other embodiments, the fluorochrome compounds of the present invention can be used directly to label cells in vitro or in vivo, or modified by covalent or noncovalent attachment to targeting ligands, small molecules, drugs, enzyme inhibitors, biomolecules, peptides, carbohydrates, proteins, antibodies, micelles or nanoparticles and used to label and image proteins, receptors, cells, tissues or in live animals. Furthermore, for imaging purposes, the invention can be used with many existing fluorescence imaging devices including but not limited to in vivo imaging instruments such as and IVIS or FMT, fluorescence microscopes, flow cytometers and cell sorters, and fluorescence plate readers.

In some aspects of the invention, the fluorochrome compounds of the present invention are substrates for P-glycoprotein (P-gp). In other aspects, the compounds are used for in vitro assessment of P-gp activity in live cells. In other aspects, the compounds are used to assess inhibition of P-gp activity in live cells by another molecule, such as a drug. In other aspects, the compounds are used to image P-gp inhibition in live animals, for example by imaging accumulation of the compounds in the brain of an animal, such as a mouse or a rat, in the presence and absence of an inhibitor or drug that may interact with P-gp. Inhibition of P-gp at the blood brain barrier would result in a higher accumulation of the fluorochrome compounds that are P-gp substrates in the brain. Changes in brain accumulation could be detected and quantified, for example, by fluorescence molecular tomography (FMT) imaging.

In another aspect of the invention, the fluorochrome compounds are chemically linked to a molecule such as a sulfonamide, for example benzenesulfonamide or acetazolamide that bind to intracellular enzymes or proteins such as carbonic anhydrase II, or extracellular or membrane bound enzymes or proteins such as carbonic anhydrase IX. In another aspect of the invention, the fluorochrome compounds are chemically linked to a drug, for example indomethacin. In another aspect of the invention, the drug linked fluorochrome compounds are used to image the drug target, such as cyclooxygenase-2 (COX-2). In a further aspect of the invention, the drug target that is imaged is intracellular. In some aspects, the targeted fluorochrome compounds can be used to image particular cellular structures or regions, such as the nucleus, cytosol, mitochondria, membrane, perinuclear regions, lysosomes or other structures, especially but not limited to applications such as microscopy, super-resolution microscopy, confocal microscopy or imaging flow cytometry. In other aspects, the targeting of specific intracellular proteins, targets, structures or biomarkers, such as the nucleus, mitochondria, membranes, lysosomes, receptors or enzymes such as carbonic anhydrases or cyclooxygenase 2, DNA, RNA, or other structures is used as a fluorescent label for the cell as a whole, for applications such as microscopy, flow cytometry, cell counting, cell sorting, or cell tracking in vitro or in vivo.

Combined with their cell permeability and handles for conjugation to targeting ligands, peptides, proteins, antibodies, or other biomolecules, the fluorochrome compounds of the present invention offer the in vivo imaging of intracellular targets that might otherwise be inaccessible using conventional red to near infrared dyes. In some aspects of the invention, the overall molecular weight of the fluorochrome compounds is low, from about 400 to about 750 Da, depending on the substituents, and preferably from 400 to 600 Da. Smaller size, relative to other near infrared fluorochromes such as indocyanine dyes, is a significant benefit for labeling biomolecules such as peptides, proteins, carbohydrates, nucleic acids, or antibodies as there is less steric interference with the natural function of the biomolecule, allowing for better imaging agents.

$W^1$, $W^2$, SX and/or Ar optionally can include a linker moiety capable of forming a covalent bond, and/or chemical linkage to a biomolecule. Such a linker moiety can include a reactive group that is capable of chemically reacting with a functional group on a different compound to form a covalent linkage, or a functional group that is capable of chemically reacting with a reactive group on different compound to form a covalent linkage. Such a reactive group can include, for example, an electrophile or nucleophile that can form a covalent linkage via exposure to a corresponding functional group that is a nucleophile or electrophile, respectively. Alternatively, the reactive group is a photoactivatable group, and becomes chemically reactive only after illumination with light of an appropriate wavelength. A reaction between the compound of the invention and the biomolecule to be linked can result in one or more atoms of a reactive group incorporated into a new linkage attaching a compound of the invention to the conjugated substance.

Biomolecules contemplated herein include, but are not limited to, proteins (for example, enzymes, hormones, antibodies and antigen binding fragments thereof, and single chain antibodies), peptides, amino acids, glycoproteins, ligands for cell receptors, polysaccharides, carbohydrates, nucleic acids (for example, DNA and RNA), nucleosides, nucleotides, aptamers, peptidyl nucleic acids, cell receptors, enzyme substrates, enzyme cofactors, biotin, hormones, neurotransmitters, growth factors, cytokines, lymphokines, lectins, selectins, lipids, lipid assemblies (for example, micelles or vesicles), and toxins. Other biomolecules can be used, such as those involved in targeting and delivery such as folate-mediated targeting (Leamon & Low, *Drug Discovery Today*, 6:44-51, 2001), transferrin, vitamins, carbohydrates and ligands that target internalizing receptors, including, but not limited to, asialoglycoprotein receptor, somatostatin, nerve growth factor, oxytocin, bombesin, calcitonin, arginine vasopressin, angiotensin II, atrial natriuretic peptide, insulin, glucagons, prolactin, gonadotropin, various opioids and urokinase-type plasminogen activator. Also contemplated are membrane, transmembrane, and nuclear translocation signal sequences, which can be derived from a number of sources including, without limitation, viruses and bacteria. Biomolecules can also include organic molecules, polymers, dendrimers, cells (for example, mammalian cells, non mammalian cells, plant cells, insect cells, embryonic cells), bacteria, bacteriophage, viruses, organisms, particles, microparticles, or nanoparticles. Biomolecules can also include therapeutic drug molecules including but not limited to phototherapy or radiotherapy molecules. Other examples of biomolecules include, without limitation, the moieties that are linked to the ring that is attached to the 9-position of the 3,6-diamino-10-silaxanthenium core (e.g., A1 in formula (I) or (II)) in compounds 67-83, 87, and 90-93.

The fluorochrome compounds of the present invention can be used to create one or more of the following types of imaging agents or probes: a molecular probe, an activatable probe, an enzyme-activatable probe, a quantum dot-based imaging probe, a nanoparticle-based imaging probe, a probe targeted to a biomolecule, a wavelength shifting beacon, a multicolor probe, a probe with high binding affinity to a target, a non-specific imaging probe, cell based probe, a dual modality agent, an optical/CT dual modality agent (e.g., an optical agent physically or chemically bound to a CT agent), an optical/MR dual modality agent (e.g., an optical agent physically or chemically bound to an MR agent), an optical/nuclear dual modality agent (e.g., an optical agent physically or chemically bound or with a radioactive atom) and/or any combination thereof.

Compounds of the invention that include a chemically linked biomolecule may have enhanced fluorescence as compared to the compound that is not chemically linked to a biomolecule. In certain embodiments, the fluorescence is enhanced by about 10%, about 25% or about 50% when compared with the unlinked compound. Biomolecules chemically linked to the compounds of the invention may alter or enhance accumulation, biodistribution, elimination, targeting, binding, and/or recognition of the molecules in vivo, ex vivo and/or in vitro.

One or more biomolecules may be chemically linked to the fluorochrome via multivalent linkages or linkers containing several reactive functional groups to form a biocompatible fluorescent molecule of the structure $(SX)-((L)_v(BM)_r)_t$, wherein L is a linker or spacer or multivalent spacer or linker, BM is a biomolecule, SX is as previously defined, and $t=1-6$, $v=1-500$ and $r=1-500$. $(L)_v$, when v is greater than 1, represents copies of the same linker or a combination of different linkers.

Examples of appropriate linker moieties for compounds of the present invention have been previously described in the literature (see, U.S. Patent Appl. 2002/0064794 (2002); U.S. Pat. No. 6,086,737; U.S. Pat. No. 6,048,982; U.S. Pat. No. 6,747,159; and U.S. Pat. No. 6,448,008).

It is understood that more than one fluorochrome compound of the present invention can be chemically linked to a single biomolecule. An example of such a structure can be represented as: $SX_u$-BM, wherein $u=1-500$ and SX and BM are as defined above.

Salts of the disclosed compounds are also contemplated, and include both base and acid addition salts. The compounds of the present invention can have one or more sufficiently acidic protons that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

The compounds of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

In other embodiments, $T_1$ is selected from the group consisting of $-NH_2$, $-OH$, $-SH$, $-SO_3H$, carboxyl, $-COCl$, $-(CO)O(CO)R_{13}$, $-CONHNH_2$, substituted and unsubstituted N-hydroxysuccinimido esters, substituted and unsubstituted N-hydroxysulfosuccinimido esters, nitro- or fluoro-phenol esters, azide, $-NCS$, $-CHO$, azide, $-COCH_2I$, phosphoramidite, phthalamido, and maleimide, wherein $R_{13}$ is selected from the group consisting of H, alkyl and aryl.

When a compound of the invention is depicted herein by structure indicating the positions of the double bonds in the SX rings and amine substituents, it is to be understood that the structure also encompasses any resonance structures as shown, for example, in the figure below:

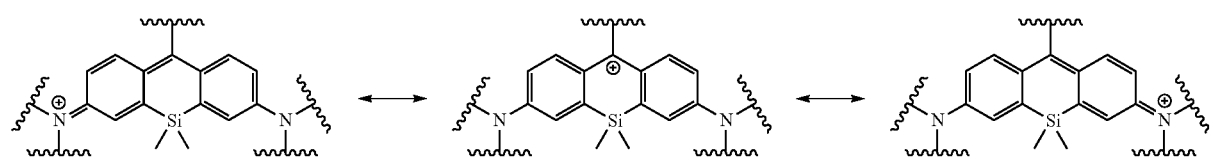

wherein, in each of the foregoing structures, substituents about the SX core are as defined herein.

In another aspect, the invention provides compounds of general structural formula:

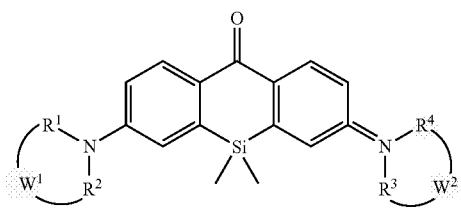

wherein $R^1$, $R^2$, $R^3$, $R^4$, $W^1$ and $W^2$ are as defined above.

In certain embodiments, $W^1$ and $W^2$ are, independently, absent or selected from groups containing aliphatic carbon, nitrogen, oxygen, sulfur, or silicon forming a 3 to 9 membered ring together with $R^1$ and $R^2$ or $R^3$ and $R^4$, optionally with further substituents on the cyclic ring Another aspect of the invention provides the following compounds:

1

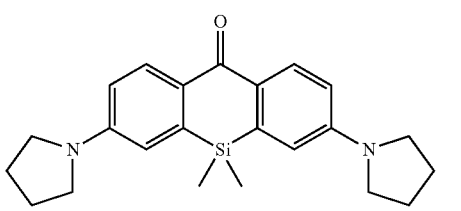

5

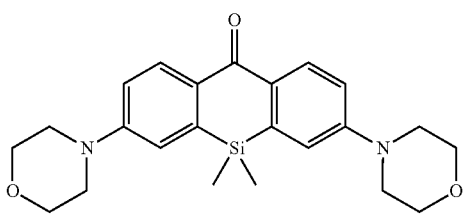

6

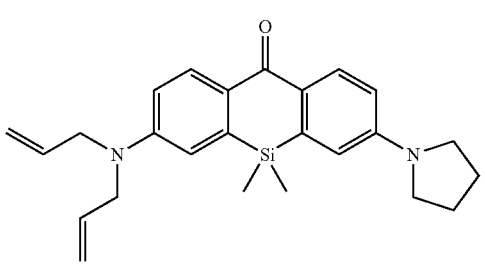

7

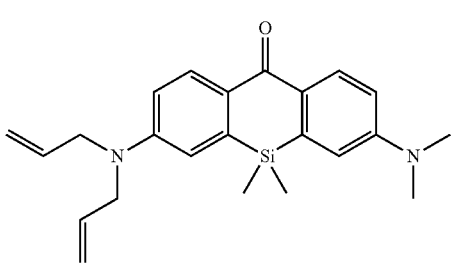

8

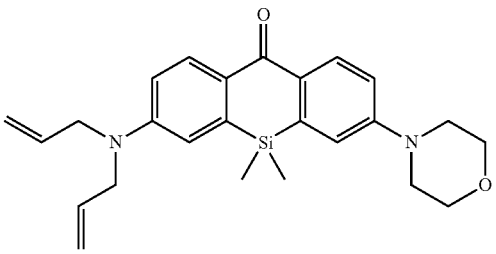

9

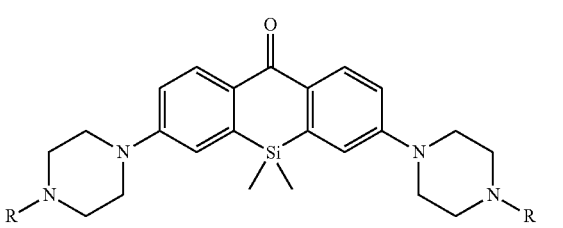

10

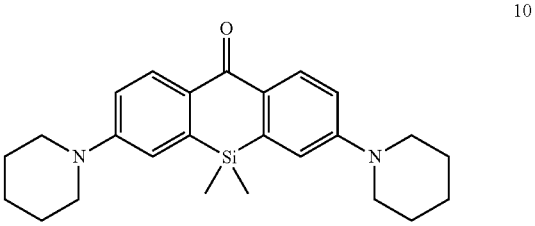

11

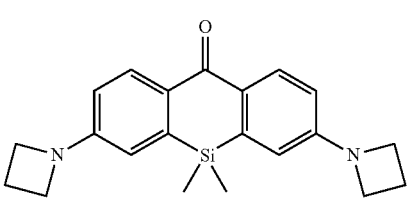

The compounds can be labeled with a biomolecules or cells as follows. The compounds (fluorochromes) of the present invention bearing reactive functional groups as described herein are incubated with one or more biomolecules at various concentrations for about 5 minutes to 24 hours or more at a temperature from about 4° C. to about 37° C. After the incubation, the free fluorochrome or the fluorochrome that has not been chemically linked to the biomolecule can be removed using methods known to those skilled in art, such as for example, chromatography or ultrafiltration methods.

Cells can be centrifuged after incubation to create a cell pellet from which the supernatant is removed. Cells can be resuspended in culture media or physiologic saline to wash away residual, unbound or free fluorochrome. This can be repeated several times. In this manner, cells can be labeled either by direct conjugation to internal or external cellular molecules or by non-specific cell uptake into various intracellular compartments, including but not limited to cytosol, endosomes, nucleus, Golgi apparatus, and other intracellular organelles.

The disclosed compounds and/or compositions can be packaged as a kit, which may optionally include instructions for using the compounds. Non-limiting examples include kits that contain, for example, a composition in a powder or lyophilized form, and instructions for using, including reconstituting, dosage information, and storage information for in vivo and/or in vitro applications. Kits may optionally contain containers of a composition in a liquid form ready for use, or requiring further mixing with solutions for administration, such as vials for reconstituting powder forms, syringes for injection, customized IV delivery systems, inhalers, etc. Such containers may contain single or multiple subject doses. Additionally, a kit can contain components that aid in the detection of the compositions in vivo or in vitro, for example, specialized endoscopes, light filters.

Compounds disclosed herein, including those compounds chemically linked to a biomolecule, can be formulated in a pharmaceutical composition suitable for administration to a subject, for example, an animal or human subject. Accordingly, the formulations include the compounds together with a physiologically acceptable carrier suitable for the desired form and/or dose of administration. Physiologically acceptable carriers can include water, saline, and may further include agents such as buffers, and other agents such as preservatives that are compatible for use in pharmaceutical formulations. The preferred carrier is a fluid, preferably a liquid, more preferably an aqueous solution; however, carriers for solid formulations, topical formulations, inhaled formulations, ophthalmic formulations, and transdermal formulations are also contemplated as within the scope of the invention.

In addition, the pharmaceutical compositions can include one or more stabilizers in a physiologically acceptable carrier. Suitable example of stabilizers for use in such compositions include, for example, low molecular weight carbohydrates, for example a linear polyalcohol, such as sorbitol, and glycerol. Other low molecular weight carbohydrates, such as inositol, may also be used.

It is contemplated that the compounds of the invention can be administered orally or parenterally. For parenteral administration, the compounds can be administered intravenously, intramuscularly, cutaneously, percutaneously, subcutaneously, rectally, nasally, vaginally, and ocularly. Thus, the composition may be in the form of, e.g., solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The pharmaceutical compositions can be formulated according to conventional pharmaceutical practice (see, for example, Remington: The Science and Practice of Pharmacy, 20th edition, 2000, ed. A. R. Germaro, Lippincott Williams & Wilkins, Philadelphia, and Encyclopedia of Pharmaceutical Technology, eds. J. Swarbrick and J. C. Boylan, 1988-1999, Marcel Dekker, New York).

III. APPLICATIONS OF THE FLUOROCHROME COMPOUNDS OF THE INVENTION

The compounds of the invention can be used in a variety of in vivo and in vitro applications. These applications are discussed in the following sections.

(a) In Vivo Applications

The invention provides novel fluorescent compounds that can be used in a variety of imaging applications, for example, optical imaging applications. For a review of optical imaging techniques, see, e.g., Alfano et al., *Ann. NY Acad. Sci.* 820:248-270, 1997; Weissleder, Nature Biotechnology 19, 316-317 (2001); Ntziachristos et al., Eur. Radiol. 13:195-208 (2003); Graves et al., *Curr. Mol. Med.* 4:419-430 (2004); Citrin et al., *Expert Rev. Anticancer Ther.* 4:857-864 (2004); Ntziachristos, *Ann. Rev. Biomed. Eng.* 8:1-33 (2006); Koo et al., *Cell Oncol.* 28:127-139 (2006); and Rao et al., *Curr. Opin. Biotechnol.* 18:17-25 (2007).

An imaging system useful in the practice of this invention typically includes three basic components: (1) an appropriate light source for exciting the fluorochrome compounds of the invention, (2) a system for separating or distinguishing emissions from light used for inducing fluorochrome excitation, and (3) a detection system. This detection system can be hand-held or incorporated into other useful imaging devices such as endoscopes, catheters, intraoperative microscopes and/or viewers.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., *Proc. Natl. Acad. Sci. USA* 91:4887-4891, 1994; Ntziachristos et al., *Proc. Natl. Acad. Sci. USA* 97:2767-2772, 2000; and Alexander, *J. Clin. Laser Med. Surg.* 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et at, *J. Photochem. Photobiol. B* 52:131-135, 1999), ovarian cancer (Major et al., *Gynecol. Oncol.* 66:122-132, 1997), colon and rectum (Mycek et al., *Gastrointest. Endosc.* 48:390-394, 1998; and Stepp et al., *Endoscopy* 30:379-386, 1998), bile ducts (Izuishi et al., *Hepatogastroenterology* 46:804-807, 1999), stomach (Abe et al., *Endoscopy* 32:281-286, 2000), bladder (Kriegmair et at, *Urol. Int.* 63:27-31, 1999; and Riedl et al., *J. Endourol.* 13:755-759, 1999), lung (Hirsch et al., *Clin Cancer Res* 7:5-220, 2001), brain (Ward, *J. Laser Appl.* 10:224-228, 1998), esophagus, and head and neck regions can be employed in the practice of the present invention.

Other types of light gathering components are catheter-based devices, including fiber optics devices. Such devices are particularly suitable for intravascular imaging. See, for example, Tearney et al., *Science* 276: 2037-2039, 1997; and *Circulation* 94: 3013, 1996.

Still other imaging technologies, including phased array technology (Boas et al., *Proc. Natl. Acad. Sci. USA* 91:4887-4891, 1994; Chance, *Ann. NY Acad. Sci.* 838:29-45, 1998), optical tomography (Cheng et al., *Optics Express* 3:118-123, 1998; and Siegel et al., *Optics Express* 4:287-298, 1999), intravital microscopy (Dellian et al., *Br. J. Cancer* 82:1513-1518, 2000; Monsky et al, *Cancer Res.* 59:4129-4135, 1999; and Fukumura et al., *Cell* 94:715-725, 1998), confocal imaging (Korlach et al., *Proc. Natl. Acad. Sci. USA* 96:8461-8466, 1999; Rajadhyaksha et al., *J. Invest. Dermatol.* 104: 946-952, 1995; and Gonzalez et al., *J. Med.* 30:337-356, 1999) and fluorescence molecular tomography (FMT) (Nziachristos et al., *Nature Medicine* 8:757-760, 2002; U.S. Pat. No. 6,615,063, PCT Application No. WO 03/102558, and PCT US/03/07579) can be used with the fluorochrome compounds of the invention. Similarly, the fluorochrome compounds can be used in a variety of imaging systems, for example, [1] the IVIS® Imaging Systems: 100 Series, 200 Series (Xenogen, Alameda, Calif.), [2] SPECTRUM and LUMINA (Xenogen, Alameda, Calif.), [3] the SoftScan® or the eXplore Optix™ (GE Healthcare, United Kingdom), [4] Maestro™ and Nuance™-2 Systems (CRi, Woburn, Mass.). [5] Image Station In-Vivo FX from Carestream Molecular Imaging, Rochester, N.Y. (formerly Kodak Molecular Imaging Systems), [6] OV100, IV100 (Olympus Corporation, Japan), [7] Cellvizio Mauna Kea Technologies, France) [8] NanoSPECT/CT or HiSPECT (Bioscan, Washington, D.C.), [9] CTLM® or LILA™ (Imaging Diagnostic Systems, Plantation, Fla.), [10] DYNOT™ (NIRx Medical Technologies, Glen Head, N.Y.) and [11] NightOWL Imaging Systems by Berthold Technologies, Germany.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

Optical imaging and measurement techniques include, but are not limited to, fluorescence imaging, luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; intravital imaging; two photon imaging; interferometry; coherence interferometry; diffuse optical tomography and fluorescence molecular tomography.

It is contemplated that the fluorochrome compounds of the injection can be coupled to or incorporated within a solid support, for example, a particle. Accordingly, it is understood that the fluorochrome compounds can be coupled to metal oxide nanoparticles that have magnetic properties to produce particles that are also fluorescent. Accordingly, the resulting particles can also be used in MRI imaging using techniques known in the art. For a review of MRI techniques see Westbrook, Handbook of MRI Technique, $2^{nd}$ Edition, 1999, Blackwell Science. It is possible that images obtained, for example, by fluorescent molecular tomography and by magnetic resonance imaging can be co-registered or fused with one another to provide additional information about the item being imaged. Furthermore, multi-modality imaging systems (i.e., combined optical and MR imaging systems) can be used to create combined optical MR images.

In addition, the compositions and methods of the present invention can be used in combination with other imaging compositions and methods. For example, the fluorochrome compounds of the invention can be used to image regions of interest via optical imaging protocols either alone or in combination with other traditional imaging modalities, such as, X-ray, computed tomography (CT), MR imaging, ultrasound, positron emission tomography (PET), and single photon computerized tomography (SPECT). For instance, the compositions and methods of the present invention can be used in combination with CT or MR imaging to obtain both anatomical and molecular information simultaneously, for example, by co-registration of an image generated by another imaging modality. The compositions and methods of the present invention can also be used in combination with X-ray, CT, PET, ultrasound, SPECT, MR and other optical contrast agents or alternatively, the fluorochrome compounds of the present invention may also contain imaging agents, such as iodine, gadolinium atoms and radioactive isotopes, which can be detected using CT, PET, SPECT, and MR imaging modalities in combination with optical imaging.

An exemplary method of in vivo optical imaging comprises the steps of (a) administering to a subject, for example, a human or an animal, a fluorescent compound of the present invention; (b) allowing sufficient time for the fluorochrome compound to distribute within the subject or to contact or interact with a biological target; (c) exposing the subject to electromagnetic radiation, for example, light of a wavelength absorbable by the fluorochrome compound; and (d) detecting an optical signal emitted by the fluorochrome compound.

It is understood that the subject may be a vertebrate animal, for example, a mammal, including a human. The animal may also be non-vertebrate, (e.g., *C. elegans, Drosophila*, or other model research organisms, etc.). The biological target can include, without limitation, cells, cell culture, tissues, tissue sections, organs, organ sections, cytospin samples, proteins, nucleic acids, carbohydrates, lipids, or the like.

The foregoing steps, including, for example, steps (a)-(d), can be repeated at predetermined time intervals thereby to permit evaluation of the emitted signals of the fluorochrome compounds in the subject over time. The illuminating and detecting steps (steps (c) and (d), respectively) can be performed using a planar imaging system, endoscope, catheter, tomographic system, hand-held optical imaging system, goggles, or an intraoperative microscope. The signal emitted by the fluorochrome compound can be used to construct an image, for example, a tomographic image.

Before or during these steps, a detection system can be positioned around or in the vicinity of a subject (for example, an animal or a human) to detect optical and/or other signals (e.g., MR, nuclear, X-ray) emitted from the subject. The emitted optical and/or other signals can be processed to construct an image, for example, a tomographic or planar image. In addition, the processed signals can be displayed as images either alone or as fused (combined) images.

In addition, it is possible to practice an in vivo imaging method that selectively detects and images one or more imaging agents simultaneously. In such an approach, for example, in step (a) noted above, two or more imaging agents whose signal properties are distinguishable from one another are administered to the subject, either at the same time or sequentially, wherein at least one of the imaging agents contains a fluorochrome compound of the invention. The use of multiple agents permits the recording of multiple biological processes, functions or targets.

The invention also features an in vivo imaging method where labeled cells are administered to the subject. The cells can be labeled with the fluorochrome compound ex vivo. The cells can be derived directly from a subject or from another source (e.g., from another subject, cell culture, etc.). The fluorochrome compound can be mixed with the cells to effectively label the cells and the resulting labeled cells administered into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

It is understood that the formulation of the fluorochrome compounds, the choice of mode of administration, the dosages of fluorochrome compounds administered to the subject, and the timing between administration of the fluorochrome compounds and their exposure of to light (and also other forms of electromagnetic radiation if appropriate under the circumstances) is within the level of skill in the art.

The methods of the invention can be used to determine a number of indicia, including tracking the localization of the fluorochrome compounds in the subject over time or assessing changes or alterations in the metabolism and/or excretion of the fluorochrome compounds in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions of the invention can also be used to help a physician or surgeon to identify and characterize areas of disease, such as arthritis, cancers and specifically colon polyps, or vulnerable or unstable plaque, to distinguish diseased and normal tissue, such as detecting tumor margins that are difficult to detect using an ordinary operating microscope, e.g., in brain surgery, to help dictate a therapeutic or surgical intervention, for example, by determining whether a lesion is cancerous and should be removed or non-cancerous and left alone, or in surgically staging a disease, e.g., intraoperative lymph node staging, sentinel lymph node mapping, or assessing intraoperative bleeding or to delineate tumor margins.

The methods and compositions of the invention can also be used in the detection, characterization and/or determination of the localization of a disease, especially early disease, the severity of a disease or a disease-associated condition, the staging of a disease, and/or monitoring a disease. The presence, absence, or level of an emitted signal can be indicative of a disease state. The methods and compositions of the invention can also be used to monitor and/or guide various therapeutic interventions, such as surgical procedures, and monitoring drug therapy, including cell based therapies. The methods of the invention can also be used in prognosis of a disease or disease condition.

With respect to each of the foregoing, examples of such disease or disease conditions that can be detected or monitored (before, during or after therapy) include, for example, inflammation (e.g., inflammation caused by arthritis, for example, rheumatoid arthritis), cancer (e.g., colorectal, ovarian, lung, breast, prostate, cervical, testicular, skin, brain, gastrointestinal, pancreatic, liver, kidney, bladder, stomach, leukemia, mouth, esophageal, bone), cardiovascular disease (e.g., atherosclerosis and inflammatory conditions of blood vessels, ischemia, stroke, thrombosis, disseminated intravascular coagulation), dermatologic disease (e.g., Kaposi's Sarcoma, psoriasis, allergic dermatitis), ophthalmic disease (e.g., macular degeneration, diabetic retinopathy), infectious disease (e.g., bacterial, viral, fungal and parasitic infections, including Acquired Immunodeficiency Syndrome, malaria, Chagas disease, schistosomiasis), immunologic disease (e.g., an autoimmune disorder, lymphoma, multiple sclerosis, rheumatoid arthritis, diabetes mellitus, lupus erythematosis, myasthenia gravis, Graves disease), central nervous system disease (e.g., a neurodegenerative disease, such as Parkinson's disease, Alzheimer's disease, Huntington's disease, amyotrophic lateral sclerosis, prion disease), inherited diseases, metabolic diseases, environmental diseases (e.g., lead, mercury and radioactive poisoning, skin cancer), bone-related disease (e.g., osteoporosis, primary and metastatic bone tumors, osteoarthritis), neurodegenerative disease, and surgery-related complications (such as graft rejection, organ rejection, alterations in wound healing, fibrosis, or other complications related to surgical implants).

The methods and compositions of the invention, therefore, can be used, for example, to determine the presence and/or localization of tumor cells, the presence and/or localization of inflammation, including the presence of activated macrophages, for instance in atherosclerosis or arthritis, the presence and in localization of vascular disease including areas at risk for acute occlusion (i.e., vulnerable plaques) in coronary and peripheral arteries, regions of expanding aneurysms, unstable plaque in carotid arteries, and ischemic areas. The disclosed methods of the invention can be used, for example, in identification and evaluation of apoptosis, necrosis, hypoxia and angiogenesis. Alternatively, the disclosed methods may also be used to assess the effect of a therapeutic compound or therapy on a specified molecular target by, for example, imaging a subject prior to and after treatment with the therapeutic compound or therapy, and comparing corresponding images.

(b) In Vitro Applications

In addition, it is appreciated that the fluorochrome compounds can be used in a variety of in vitro assays, for example, binding experiments, detection of analytes, fluorescence resonance energy transfer (FRET) assays, time-resolved fluorescence assays, signal amplification assays, such as tyramide signal amplification assays, homogeneous assays, such as luminescent oxygen channeling immunoassays, high throughput screening, high content screening, flow cytometry, cell assays (lysed or live), microscopy and in vitro imaging experiments. It is understood that the imaging technologies discussed in the previous section are also applicable to in vitro imaging experiments.

An exemplary in vitro imaging method comprises: (a) contacting a sample with a probe comprising a fluorochrome compound of the invention; (b) allowing the fluorochrome compound to (i) become activated by and/or (ii) bind to a biological target; (c) optionally removing unactivated or unbound fluorochrome compound; (d) exposing the sample to electromagnetic radiation, for example, light, of a wavelength absorbable by the fluorochrome compound; and (e) detecting signal emitted from the fluorochrome compounds thereby to determine whether the probes have been activated or bound by the biological target.

It is also appreciated that the fluorochrome compounds of the present invention can be used alongside or in parallel with other classes of fluorochrome compounds, such as fluoresceins, rhodamines, cyanines, boron-dipyrromethenes, or oxazines, and that the unique chemical, physical, and optical properties of the fluorochromes of the present invention makes them particularly well suited to multiplexed fluorescent assays that include the simultaneous use of one or more fluorochromes from another class of fluorochrome compounds.

The sample can be a liquid or solid sample containing, for example, primary cells, cell cultures, or tissue, a virus, an analyte, proteins, immunoglobulins, carbohydrates, enzymes, lipids, cytokines, histones, modified, histones, DNA, modified DNA, or other biomolecules. The biological target can be, for example, a cell, an aggregation of cells, a tissue or tissue sample, a structure (both on the macrocellular level (for example, bone or tissue) or on a subcellular level (for example, a mitochondria or nucleus)), and a cellular component, for example, a protein (for example, an enzyme or structural protein), lipid, nucleic acid or polysaccharide. It is also considered that the sample could contain markers of the presence of particular cells or biological entities, such as proteins, peptides, viruses, DNA, RNA, lipids, carbohydrates, etc. in the absence of live or intact cells, as in water samples, soil samples, food samples, or other samples of biological or non-biological origin.

It is also contemplated that the fluorochrome compounds of the present invention could be used to detect non-biological materials or materials from non-biological origin in samples of biological or non-biological origin. Examples include the detection of such materials as explosives, toxins, weapons, fertilizers, drugs, heavy metals, trace metals, metal cations, industrial wastes, or other analytes.

The fluorochrome compounds can be used in a variety of in vitro ligand binding assays such, when incorporated into magnetic particles, can be used in magnetic detection based assays (see, U.S. Pat. Nos. 6,046,585 and 6,275,031, U.S. Pat. No. 5,445,970; U.S. Pat. No. 4,219,335, Chemla, et. al. (2000) *Proc Natl Acad. Sci USA* 97, 14268-72). They can also be used in magnetic resonance based ligand binding assays such as those described in U.S. Pat. No. 5,164,297 and Perez et al. *Nature Biotechnol.* 2002, 20(8):816-20. The fluorochrome compounds can also be used for cell sorting and counting applications.

The fluorochrome compounds can also be used as reporter groups in a nucleic acid-based assays. For example, the fluorochrome compounds can be coupled to nucleic acids, for example, DNA or RNA, modified nucleic acids, PNAs, molecular beacons, or other nucleic acid binding molecules (for example, small interfering RNA or siRNA) for use in hybridization assays, for example, in situ hybridization assays, sequencing reactions, amplification reactions, for example, real-time polymerase chain reaction amplification reactions. For example, for detecting a single stranded nucleic acid (i.e., mRNA, cDNA or denatured double-stranded DNA) in a sample via nucleic acid hybridization principles, a fluorochrome compound of the invention is chemically linked to a single-stranded nucleic acid (probe) and contacted with a sample suspected of containing one or more single stranded nucleic acids (target nucleic acids), optionally immobilized on a solid support. The probe is incubated with the sample under conditions to permit the probe to hybridize to target nucleic acid in the sample to form a duplex. Unbound probe can be removed by washing, and the bound probe can be detected, wherein the presence or level of fluorescence emitted by the fluorochrome compound in the probe is indicative of the presence or amount of the target nucleic acid in the sample.

The fluorochrome compounds can also be used in fluorescence resonance energy transfer (FRET) based assays, or time resolved FRET (TR-FRET) assays, or in conjunction with a quencher molecule. When the fluorochrome compounds are in close proximity to an appropriate acceptor or donor for FRET, for example a metal chelate such as Europium, or another fluorochrome, transfer of energy may occur to or from the fluorochrome compounds to the other donor or acceptor molecule. Changes in the proximity of the fluorochrome compound to the other donor or acceptor molecule through binding, accumulation, action of an enzyme or the like will change the efficiency of the FRET or TR-FRET. Such changes can be measured and used to quantify the binding, accumulation or action of an enzyme.

In another aspect of the invention, the fluorochromes of the present invention can be used to detect the presence, absence, quantity, or change in quantity of a metal or metal cation. Suitable metal chelating groups can be attached to the fluorochrome compounds and a change in the fluorescence of the fluorochrome compound observed upon binding or release of a target metal, such as copper, zinc, calcium, lead, cadmium, mercury, iron, cobalt, manganese, chromium, or other metals.

The fluorochrome compounds are particularly useful for the detection and quantification of an analyte. During a detection assay, the signal emitted from the compound is indicative of activation of the compound and/or binding to a biological target, or to determine the presence, absence or quantity of an analyte in the sample, optionally with temporal resolution as in a time resolved fluorescence measurement.

In one aspect, the signal of the compound is amplified by the presence of an enzyme, wherein the enzyme is bound to or in the proximity of the biological target, and wherein the activity of the enzyme results in accumulation or binding of the fluorescent compound to the target, analyte or surrounding area. An example enzyme is horseradish peroxidase, which can be bound to other molecules, such as an antibody, and which can act on fluorochrome compounds conjugated to, for example, tyramide or 4-hydroxycinnamamide to signal amplified accumulation and binding of the fluorochrome compounds to molecules in close proximity to the enzyme.

In an aspect of the invention, the fluorochrome compounds can be used as a component in a homogeneous assay for the determination of the presence or quantity of an analyte consisting of (a) an analyte-specific binding partner containing a singlet oxygen sensitizer (donor) that can be excited with incident light at an appropriate wavelength and (b) a second analyte-specific binding partner containing a singlet oxygen sensitive moiety and one or more fluorescent or luminescent moieties, including the compound of the present invention, that will emit light in the presence of singlet oxygen.

In another aspect of the invention, the fluorochrome compounds can be used for the analysis or imaging of individual cells as under a microscope or in a flow cytometer or in an imaging flow cytometer.

In another aspect of the invention, the fluorochrome compounds can be used for the analysis or imaging of groups of cells, as in a sample of intact tissue or similar sample, as under a microscope or other suitable imaging device (e.g., a flow cytometer or in an imaging flow cytometer).

In another aspect of the invention, the fluorochrome compounds can be used for the analysis or imaging multiple samples successively as in a high throughput screening assay. Such an assay could take place within, for example, a 96-well plate, or a 384-well plate, or a 1536 well plate.

The fluorochrome compounds can also be used as a component or components in the analysis of multiple biomarkers, targets or analytes in a sample or set of samples, along with a suitable imaging or analysis device, in a multiplexed assay, a high content screening assay, or a high content analysis assay. Two, three, four, five, six or more different targets or markers in a single sample can be quantified or imaged together with individual probes to provide a high content readout of the state of the sample under analysis.

(c) Ex Vive Applications

In addition, it is appreciated that the fluorochrome compounds can be used in a variety of ex vivo assays, for example, binding experiments, and ex vivo imaging experiments. It is understood that the imaging technologies discussed in the previous sections are also applicable to ex vivo imaging experiments.

An exemplary ex vivo imaging method comprises: (a) contacting a sample with a probe comprising a fluorochrome compound of the invention; (b) allowing the fluorochrome compound to (i) become activated by and/or (ii) bind to a biological target; (c) optionally removing unactivated or unbound fluorochrome compound; (d) exposing the sample to electromagnetic radiation, for example, light, of a wavelength absorbable by the fluorochrome compound; and (e) detecting signal emitted from the fluorochrome compounds thereby to determine whether the probes have been activated or bound by the biological target.

The sample can be a liquid or solid sample containing, for example, primary cells, cell cultures, or tissue. The biological target can be, for example, a cell, an aggregation of cells, a tissue or tissue sample, a structure (both on the macrocellular level (for example, bone organ or tissue) or on a subcellular level (for example, a mitochondria or nucleus), and a cellular component, for example, a protein (for example, an enzyme or structural protein), lipid, nucleic acid or polysaccharide.

EXAMPLES

The invention now being generally described, will be more readily understood by reference to the following examples, which are included merely for purposes of illustration of certain aspects and embodiments of the present invention, and are not intended to limit the invention.

Representative materials and methods that may be used in preparing the compounds of the invention are described further below. All commercially available chemicals and solvents (reagent grade) are used as supplied without further purification in general. Analytical and preparative HPLC methods include:

A Column: Agilent Zorbax 80 Å, Extend C18, 4.6×250 mm (5 μm).
Mobile phase: Acetonitrile, 25 mM triethylammonium acetate.
B Column: Varian Dynamax, 100 Å, C18, 41.4×250 mm.
Mobile phase: Acetonitrile, 25 mM triethylammonium acetate.
C Column: Phenomenex Jupiter, 300 Å, C18
Mobile phase: Acetonitrile, 25 mM triethylammonium acetate.

Example 1—Synthesis of Compound 22: (3,6-bis (dimethylamino)-9-(2-carboxy-4-methyl-thien-5-yl)-10,10-dimethyl-10-silaxanthenium chloride)

Compound 22 was synthesized according to the following scheme:

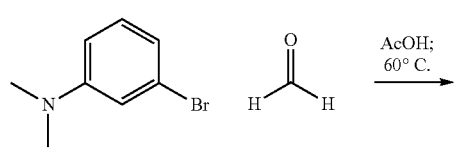

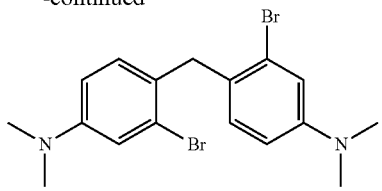

To a solution of compound N,N dimethyl-3-bromo aniline (10.0 g, 50.0 mmol) in AcOH (250 mL) was added 12.16 mL of 37% formaldehyde aqueous solution (4.5 g, 150.0 mmol), and the mixture was stirred at 60° C. for 115 min. After cooling to room temperature, a portion of acetic acid was removed by vacuum. Then, the reaction mixture was neutralized with saturated NaHCO₃ aq. and NaOH aq., and extracted with CH₂Cl₂. The organic layer was washed with brine, dried over Na₂SO₄ and evaporated to dryness. The residue was purified by flash chromatography (silica gel) to give pure 4,4'-methylenebis(3-bromo-N,N-dimethylaniline) (5.24 g, 12.7 mmol, 51% yield).

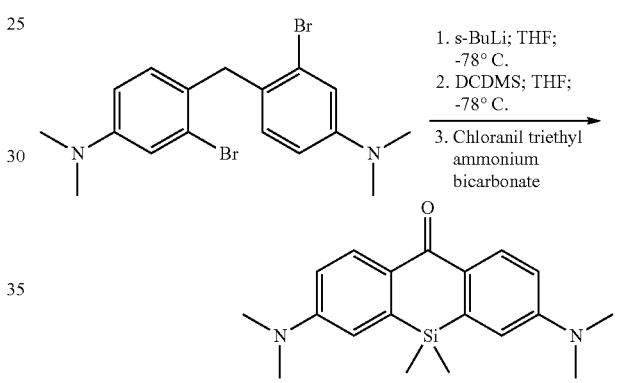

To a nitrogen purged flask, 4,4'-methylenebis(3-bromo-N,N-dimethylaniline) (1000 mg, 2.42 mmol) and anhydrous THF (25 mL) were added. The solution was cooled to −78° C., 1.4 M s-BuLi (3.46 mL, 4.84 mmol) was added, and the mixture was stirred for 30 min. At the same temperature, Me₂SiCl₂ (324 μL, 2.62 mmol) dissolved in anhydrous THF (25 mL) was slowly added, and the mixture was warmed to r.t., then stirred for 1 hour. The reaction was quenched by addition of 2 N HCl and the mixture was stirred at r.t. for 10 min. Saturated NaHCO₃ was added, and the whole was extracted with CH₂Cl₂. Chloranil (1750 mg, 7.05 mmol) was then added to the combined organic layers along with 1 M triethylammonium bicarbonate (3 mL) and the mixture was stirred overnight. The solvent was evaporated and the residue purified by flash chromatography (silica gel) provide pure 3,6-bis(dimethylamino)-10,10-dimethyl-10-silaxanthone (425 mg, 1.3 mmol, 54% yield).

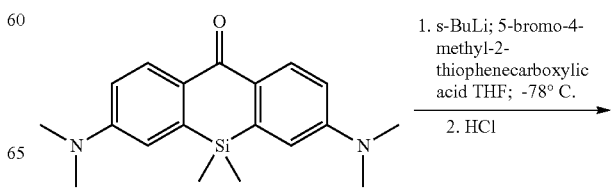

-continued

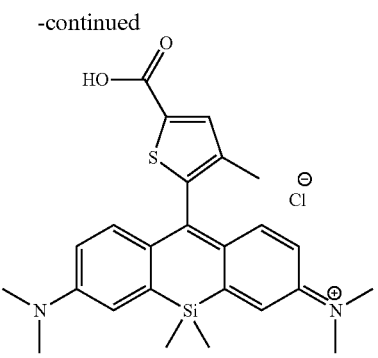

22

To a nitrogen purged flask, 3,6-bis(dimethylamino)-10,10-dimethyl-10-silaxanthone (50.0 mg, 0.16 mmol) was dissolved in anhydrous THF (10 mL). The solution was cooled to −78° C. At the same temperature 4-methyl-5-bromo-2-thiophenecarboxylic acid (136 mg, 0.81 mmol) and anhydrous THF (5 mL) were added to a flask, 1 M s-BuLi (1.16 mL, 1.62 mmol) was added, and the mixture was stirred for 30 min. The lithiated solution was slowly added, and the mixture was warmed to r.t., then stirred for 2 h. The reaction was quenched by addition of 2 N HCl and the mixture was stirred at r.t. for 10 min. Saturated NaHCO₃ was added, and the whole was extracted with CH₂Cl₂. The organic layer was dried over Na₂SO₄, and the solvent was evaporated. The crude mixture was purified by HPLC to afford pure 3,6-bis(dimethylamino)-9-(2-carboxy-4-methyl-thien-5-yl)-10,10-dimethyl-10-silaxanthenium chloride 22 (9.7 mg, 0.022 mmol, 14% yield).

Example 2—Synthesis of Compound 65: (3,6-bis(dimethylamino)-9-(2-carboxy-thien-5-yl)-10,10-dimethyl-10-silaxanthenium chloride)

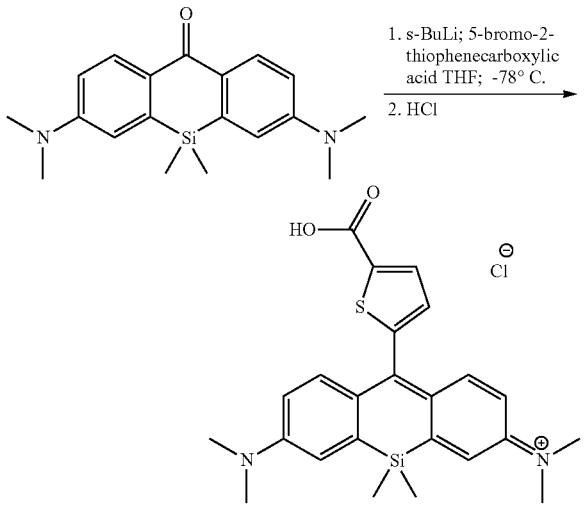

65

To a nitrogen purged flask, 3,6-bis(dimethylamino)-10,10-dimethyl-10-silaxanthone (50.0 mg, 0.16 mmol) was dissolved in anhydrous THF (10 mL). The solution was cooled to −78° C. At the same temperature tert-butyl 4-bromo-3-methyl-2-thiophenecarboxylic acid (136 mg, 0.81 mmol) and anhydrous THF (5 mL) were added to a flask, 1 M s-BuLi (1.16 mL, 1.62 mmol) was added, and the mixture was stirred for 30 min. The lithiated solution was slowly added, and the mixture was warmed to r.t., then stirred for 2 h. The reaction was quenched by addition of 2 N HCl and the mixture was stirred at r.t. for 10 min. Saturated NaHCO₃ was added, and the whole was extracted with CH₂Cl₂. The organic layer was dried over Na₂SO₄, and the solvent was evaporated. The crude mixture was purified by HPLC to afford pure 3,6-bis(dimethylamino)-9-(2-carboxy-thien-5-yl)-10,10-dimethyl-10-silaxanthenium chloride 65 (9.7 mg, 0.022 mmol, 14% yield).

Example 3—Synthesis of Compound 18: (3,6-bis(dimethylamino)-9-(2-carboxy-3-methyl-thien-4-yl)-10,10-dimethyl-10-silaxanthenium chloride)

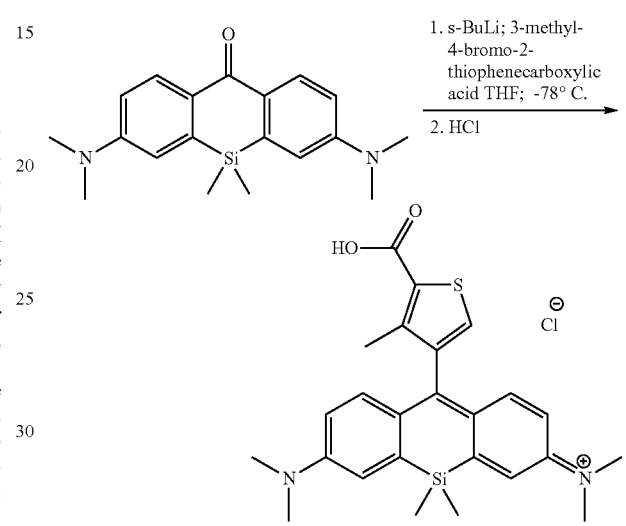

18

To a nitrogen purged flask, 3,6-bis(dimethylamino)-10,10-dimethyl-10-silaxanthone (50.0 mg, 0.16 mmol) was dissolved in anhydrous THF (10 mL). The solution was cooled to −78° C. At the same temperature 3-methyl-4-bromo-2-thiophenecarboxylic acid (136 mg, 0.81 mmol) and anhydrous THF (5 mL) were added to a flask, 1 M s-BuLi (1.16 mL, 1.62 mmol) was added, and the mixture was stirred for 30 min. The lithiated solution was slowly added, and the mixture was warmed to r.t., then stirred for 2 h. The reaction was quenched by addition of 2 N HCl and the mixture was stirred at r.t. for 10 min. Saturated NaHCO₃ was added, and the whole was extracted with CH₂Cl₂. The organic layer was dried over Na₂SO₄, and the solvent was evaporated. The crude mixture was purified by HPLC to afford pure 3,6-bis(dimethylamino)-9-(2-carboxy-3-methyl-thien-4-yl)-10,10-dimethyl-10-silaxanthenium chloride 18 (9.7 mg, 0.022 mmol, 14% yield).

Example 4—Synthesis of Compound #17: (2,6-bis(dimethylamino)-9-(2-carboxy-4-methyl-thien-3-yl)-10,10-dimethyl-10-silaxanthenium chloride) IV Compound 17 was prepared as described in the following scheme:

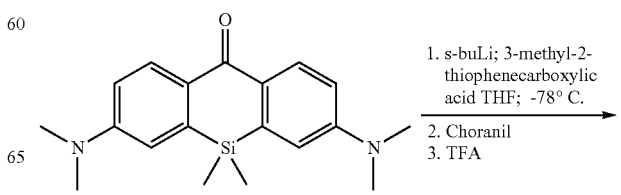

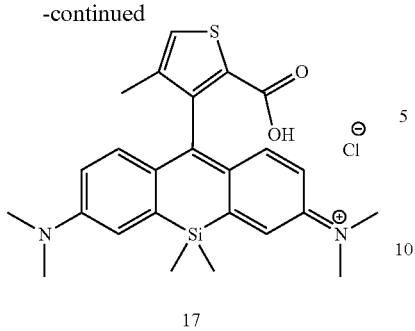

17

To a nitrogen purged flask, 3,6-bis(dimethylamino)-10,10-dimethyl-10-silaxanthone (50.0 mg, 0.16 mmol) was dissolved in anhydrous THF (10 mL). The solution was cooled to −78° C. At the same temperature tert-butyl 4-bromo-3-methylbenzoate (136 mg, 0.81 mmol) and anhydrous THF (5 mL) were added to a flask, 1 M s-BuLi (1.16 mL, 1.62 mmol) was added, and the mixture was stirred for 30 min. The lithiated solution was slowly added, and the mixture was warmed to r.t., then stirred for 2 h. The reaction was quenched by addition of 2 N HCl and the mixture was stirred at r.t. for 10 min. Saturated NaHCO$_3$ was added, and the whole was extracted with CH$_2$Cl$_2$. The organic layer was dried over Na$_2$SO$_4$, and the solvent was evaporated. The crude mixture was purified by HPLC to afford pure 3,6-bis(dimethylamino)-9-(2-carboxy-4-methyl-thien-3-yl)-10,10-dimethyl-10-silaxanthenium chloride 17 (9.7 mg, 0.022 mmol, 14% yield).

Example 5—Synthesis of Compound 44: (2,6-bis(pyrridolin-1-yl)-9-(2-methyl-4-carboxyphenyl)-10,10-dimethyl-10-silaxanthenium)

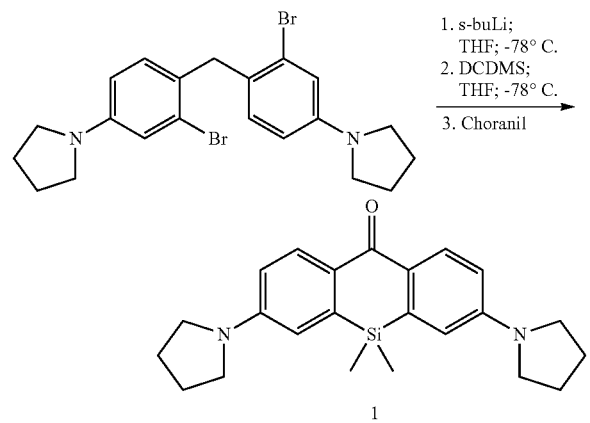

1

To a nitrogen purged flask, bis(2-bromo-4-(pyrrolidin-1-yl)phenyl)methane (1000 mg, 2.42 mmol) and anhydrous THF (25 mL) were added. The solution was cooled to −78° C., 1.4 M s-BuLi (3.46 mL, 4.84 mmol) was added, and the mixture was stirred for 30 min. At the same temperature, Me$_2$SiCl$_2$ (3.24 µL, 2.62 mmol) dissolved in anhydrous THF (25 mL) was slowly added, and the mixture was warmed to r.t., then stirred for 1 hour. The reaction was quenched by addition of 2 N HCl and the mixture was stirred at r.t. for 10 min. Saturated NaHCO$_3$ was added, and the whole was extracted with CH$_2$Cl$_2$. The organic layer was dried over Na$_2$SO$_4$ and evaporated. The residue was dissolved in CH$_2$Cl$_2$ (10 mL), followed by addition of chloranil (1250 mg, 5.0 mmol) along with 1 M triethylammonium bicarbonate (2.5 mL, 2.5 mmol) and the mixture was stirred at room temperature overnight. The solvent was evaporated and the residue purified by flash chromatography (silica gel) to provided pure 3,6-bis(pyrridolin-1-yl)-10,10-dimethyl-10-silaxanthone.

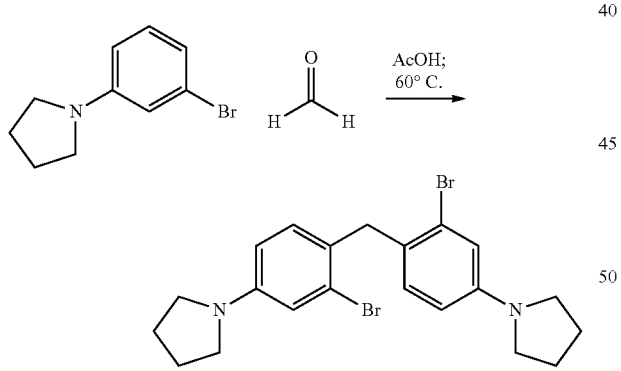

To a solution of compound 1-(3-bromophenyl)-pyrrolidine (10.0 g, 44 mmol) in AcOH (250 mL) was added 12.16 mL of 37% formaldehyde aqueous solution (4.5 g, 150.0 mmol), and the mixture was stirred at 60° C. for 115 min. After cooling to room temperature, a portion of acetic acid was removed by vacuum. Then, the reaction mixture was neutralized with saturated NaHCO$_3$ aq. and NaOH aq., and extracted with CH$_2$Cl$_2$. The organic layer was washed with brine, dried over Na$_2$SO$_4$ and evaporated to dryness. The residue was purified by flash chromatography (silica gel) to give pure bis(2-bromo-4-(pyrrolidin-1-yl)phenyl)methane (5.1 g, 11 mmol, 50% yield).

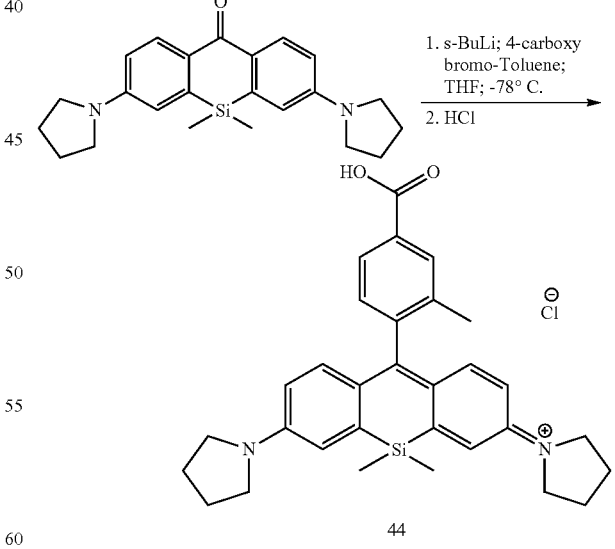

44

To a nitrogen purged flask, 2,6-bis(pyrridolin-1-yl)-10,10-dimethyl-10-silaxanthone (50.0 mg, 0.162 mmol) was dissolved in anhydrous THF (10 mL). The solution was cooled to −78° C. At the same temperature tert-butyl 4-bromo-3-methylbenzoate (136 mg, 0.81 mmol) and anhydrous THF (5 mL) were added to a flask, 1 M s-BuLi (0.58 mL, 0.81 mmol) was added, and the mixture was stirred for 30 min. The lithiated solution was slowly added, and the mixture was warmed to r.t., then stirred for 2 h. The reaction was quenched by addition of 2 N HCl and the mixture was stirred at r.t. for 10 min. Saturated NaHCO$_3$ was added, and the whole was extracted with CH$_2$Cl$_2$. The organic layer was dried over Na$_2$SO$_4$, and the solvent was evaporated. The crude mixture was purified by HPLC to afford pure residue which was dissolved in TFA (1 mL). TFA was removed by vacuum affording 3,6-bis(pyrridolin-1-yl)-9-(2-methyl-4-carboxyphenyl)-10,10-dimethyl-10-silaxanthenium 44 (9.7 mg, 0.022 mmol, 14% yield).

Example 6: Synthesis of Compound 74—(3,6-bis(piperidin-1-yl)-9-(2-methyl-4-carboxyphenyl)-10,10-dimethyl-10-silaxanthenium)

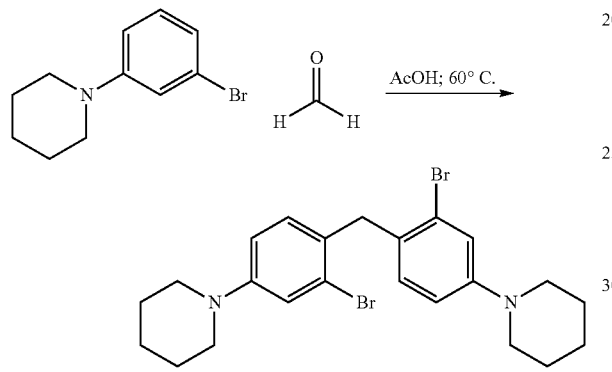

To a solution of compound 1-(3-bromophenyl)-piperidine (10.0 g, 50.0 mmol) in AcOH (250 mL) was added 12.16 mL of 37% formaldehyde aqueous solution (4.5 g, 150.0 mmol), and the mixture was stirred at 60° C. for 115 min. After cooling to room temperature, a portion of acetic acid was removed by vacuum. Then, the reaction mixture was neutralized with saturated NaHCO$_3$ aq. and NaOH aq., and extracted with CH$_2$Cl$_2$. The organic layer was washed with brine, dried over Na$_2$SO$_4$ and evaporated to dryness. The residue was purified by flash chromatography (silica gel) to give bis(2-bromo-4-(piperidin-1-yl)phenyl)methane (5.24 g, 12.7 mmol, 51% yield).

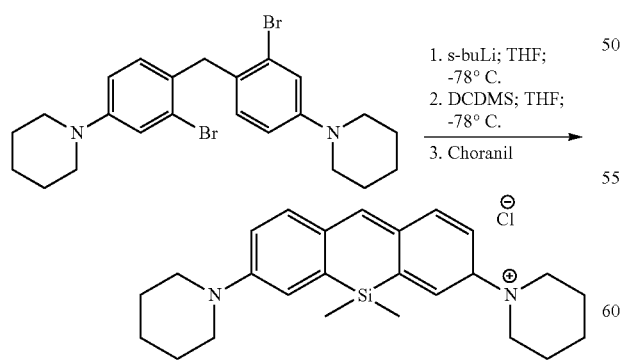

To a nitrogen purged flask, bis(2-bromo-4-(piperidin-1-yl)phenyl)methane (1.0 g, 2.2 mmol) and anhydrous THF (25 mL) were added. The solution was cooled to −78° C., 1.4 M s-BuLi (3.46 mL, 4.84 mmol) was added, and the mixture was stirred for 30 min. At the same temperature, Me$_2$SiCl$_2$ (3.24 µL, 2.62 mmol) dissolved in anhydrous THF (25 mL) was slowly added, and the mixture was warmed to r.t., then stirred for 1 hour. The reaction was quenched by addition of 2 N HCl and the mixture was stirred at r.t. for 10 min. Saturated NaHCO$_3$ was added, and the whole was extracted with CH$_2$Cl$_2$. The organic layer was dried over Na$_2$SO$_4$ and evaporated. The residue was dissolved in CH$_2$Cl$_2$ (10 mL), followed by addition of chloranil (600 mg, 2.4 mmol). The solvent was evaporated again. Purification of the residue by flash chromatography (silica gel) provided pure 3,6-bis(pyrrolidin-1-yl)-10,10-dimethyl-10-silaxanthen-9-ium chloride (340 mg, 40% yield).

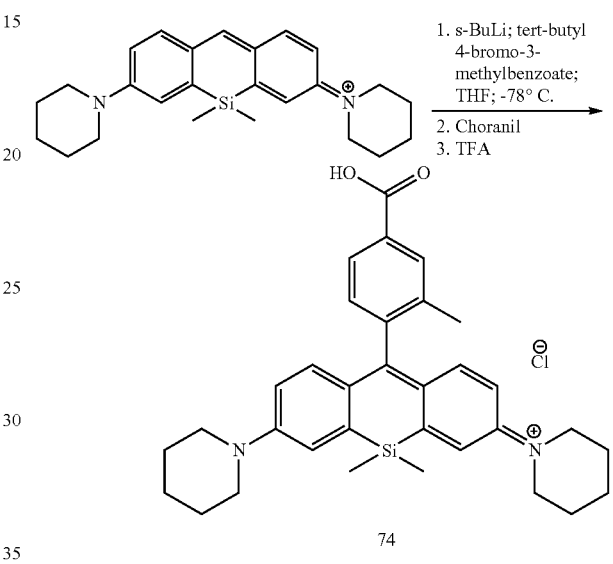

To a nitrogen purged flask, 3,6-bis(pyrrolidin-1-yl)-10,10-dimethyl-10-silaxanthen-9-ium chloride (50.0 mg, 0.125 mmol) was dissolved in anhydrous THF (10 mL). The solution was cooled to −78° C. At the same temperature tert-butyl 4-bromo-3-methylbenzoate (136 mg, 0.81 mmol) and anhydrous THF (5 mL) were added to a flask, 1 M s-BuLi (0.58 mL, 0.81 mmol) was added, and the mixture was stirred for 30 min. The lithiated solution was slowly added, and the mixture was warmed to r.t., then stirred for 2 h. The reaction was quenched by addition of 2 N HCl and the mixture was stirred at r.t. for 10 min. Saturated NaHCO$_3$ was added, and the whole was extracted with CH$_2$Cl$_2$. The organic layer was dried over Na$_2$SO$_4$, and the solvent was evaporated. The crude mixture was purified by HPLC to afford pure residue which was dissolved in TFA (1 mL). TFA was removed by vacuum affording 3,6-bis(piperidin-1-yl)-9-(2-methyl-4-carboxyphenyl)-10,10-dimethyl-10-silaxanthenium 74 (11.2 mg 16% yield).

Example 7—Synthesis of Compound 45: (3,6-bis(morpholino)-9-(2-methyl-4-carboxyphenyl)-10,10-dimethyl-10-silaxanthenium)

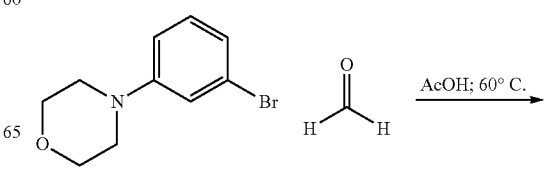

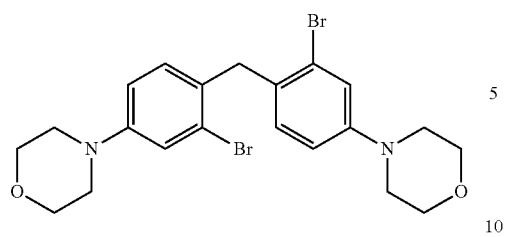

To a solution of compound 1-(3-bromophenyl)-morpholine (10.0 g, 41.0 mmol) in AcOH (250 mL) was added 12.16 mL of 37% formaldehyde aqueous solution (4.5 g, 150.0 mmol), and the mixture was stirred at 60° C. for 115 min. After cooling to room temperature, a portion of acetic acid was removed by vacuum. Then, the reaction mixture was neutralized with saturated NaHCO$_3$ aq. and NaOH aq., and extracted with CH$_2$Cl$_2$. The organic layer was washed with brine, dried over Na$_2$SO$_4$ and evaporated to dryness. The residue was purified by flash chromatography (silica gel) to give bis(2-bromo-4-morpholinophenyl)methane (5.1 g, 50% yield).

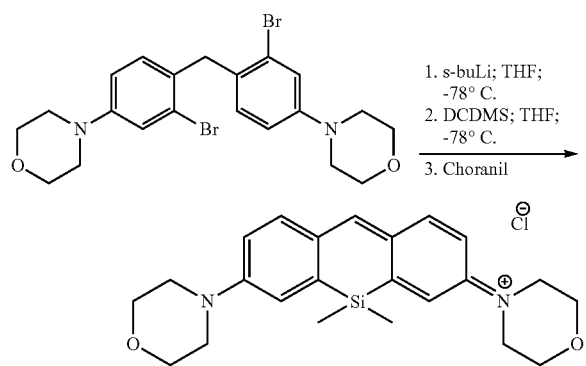

To a nitrogen purged flask, bis(2-bromo-4-morpholinophenyl)methane (1.0 g, 2.2 mmol) and anhydrous THF (25 mL) were added. The solution was cooled to −78° C., 1.4 M s-BuLi (3.46 mL, 4.84 mmol) was added, and the mixture was stirred for 30 min. At the same temperature, Me$_2$SiCl$_2$ (3.24 μL, 2.62 mmol) dissolved in anhydrous THF (25 mL) was slowly added, and the mixture was warmed to r.t., then stirred for 1 hour. The reaction was quenched by addition of 2 N HCl and the mixture was stirred at r.t. for 10 min. Saturated NaHCO$_3$ was added, and the whole was extracted with CH$_2$Cl$_2$. The organic layer was dried over Na$_2$SO$_4$ and evaporated. The residue was dissolved in CH$_2$Cl$_2$ (10 mL), followed by addition of chloranil (600 mg, 2.4 mmol). The solvent was evaporated again. Purification of the residue by flash chromatography (silica gel) provided pure 3,6-bis(pyrrolidin-1-yl)-10,10-dimethyl-10-silaxanthen-9-ium chloride (340 mg, 40% yield).

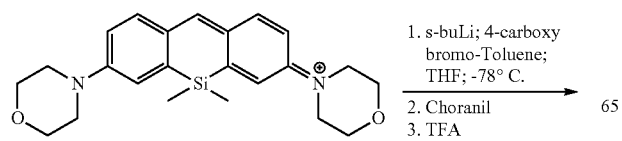

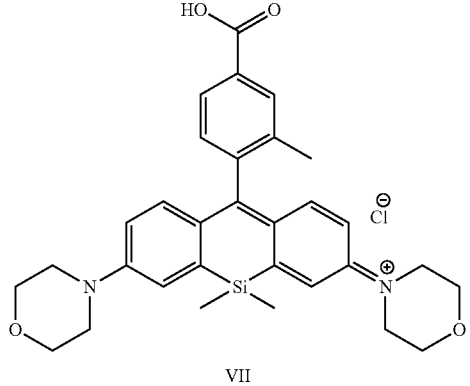

VII

To a nitrogen purged flask, 3,6-bis(pyrrolidin-1-yl)-10,10-dimethyl-10-silaxanthen-9-ium chloride (50.0 mg, 0.125 mmol) was dissolved in anhydrous THF (10 mL). The solution was cooled to −78° C. At the same temperature tert-butyl 4-bromo-3-methylbenzoate (136 mg, 0.81 mmol) and anhydrous THF (5 mL) were added to a flask, 1 M s-BuLi (0.58 mL, 0.81 mmol) was added, and the mixture was stirred for 30 min. The lithiated solution was slowly added, and the mixture was warmed to r.t., then stirred for 2 h. The reaction was quenched by addition of 2 N HCl and the mixture was stirred at r.t. for 10 min. Saturated NaHCO$_3$ was added, and the whole was extracted with CH$_2$Cl$_2$. The organic layer was dried over Na$_2$SO$_4$, and the solvent was evaporated. The crude mixture was purified by HPLC to afford pure residue which was dissolved in TFA (1 mL). TFA was removed by vacuum affording 3,6-bis(morpholino)-9-(2-methyl-4-carboxyphenyl)-10,10-dimethyl-10-silaxanthenium 45 (11.2 mg 16% yield).

Example 8. Exemplary Substituent Effects on Optical Properties for 9-Substituted 10-Silaxanthenium Fluorochromes This example shows the optical properties (absorption and emission maximum wavelength and relative brightness). The relative brightness is defined by the fluorescence intensity of a solution of the fluorochrome in a 1 cm square cuvette when excited at its wavelength of maximum absorption divided by the absorption of the same sample at the wavelength of maximum absorption. The three examples shown with a S atom in the X position of Formula II are red shifted about 20 nm relative to three examples with the S atom in the Y or Z positions. Further derivatization of the thienyl substituent with methyl, bromo, or carboxy substituents shows a 28-fold range of relative brightness:

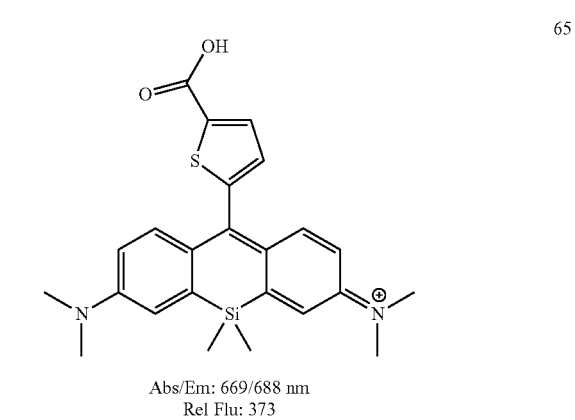

Abs/Em: 669/688 nm
Rel Flu: 373

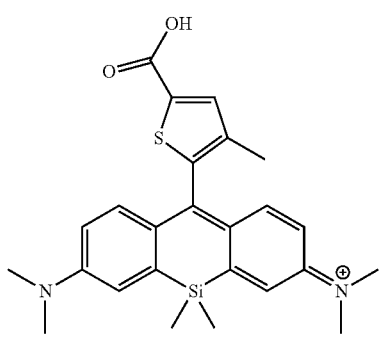

22

Abs/Em: 668/678 nm
Rel Flu: 3,032

66

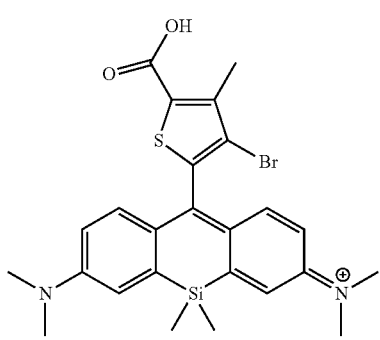

Abs/Em: 672/688 nm
Rel Flu: 3,838

16

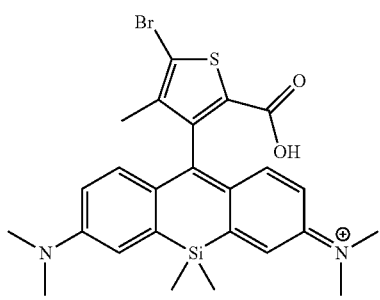

Abs/Em: 649/664 nm
Rel Flu: 6,185

18

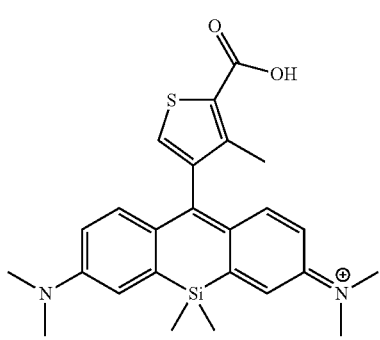

Abs/Em: 653/6668 nm
Rel Flu: 9,608

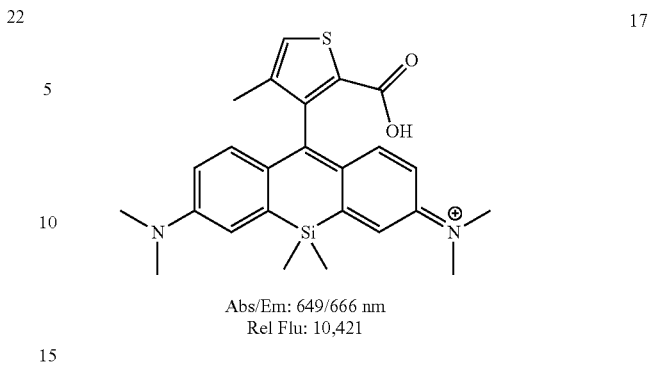

Abs/Em: 649/666 nm
Rel Flu: 10,421

Figure 1B:
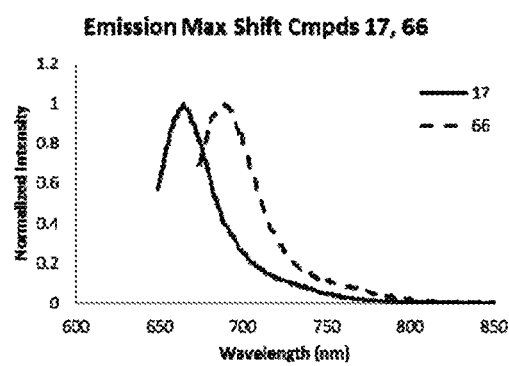

FIG. 1 illustrates a 23 nm red shift observed upon moving the sulfur atom of a 9-thienyl SX compound from the Z position of Formula I (compound 17) to the X position and adding a bromine substituent (compound 66). This shift is sufficient to allow multiplex imaging on two different wavelengths with these two compounds, for example on a four channel FMT tomographic in vivo imaging system or a multichannel fluorescence microscope.

Example 9. Properties of Some Exemplary Silaxanthenium Fluorochrome Compounds

This example summarizes in Table 3 the absorption and emission characteristics of some exemplary silaxanthenium (SX) fluorochromes relative to a cell impermeable cyanine dye (sulfonated Cy5 analog) CY1. Absorption and emission characteristics were measured in 1×PBS in a 1 cm square cuvette. Relative fluorescence (brightness) was measured as in Example 8 and normalized to that of compound CY1.

TABLE 3

| Compound | Abs. λmax (nm) | Em. λmax (nm) | Relative Fluorescence |
|---|---|---|---|
| CY1 | 648 | 666 | 1.00 |
| 75 | 649 | 662 | 1.46 |
| 76 | 649 | 663 | 1.38 |
| 77 | 650 | 666 | 1.20 |
| 17 | 649 | 666 | 1.11 |
| 45 | 651 | 670 | 0.75 |
| 18 | 653 | 668 | 1.02 |
| 62 | 654 | 667 | 1.12 |
| 44 | 655 | 669 | 1.54 |
| 65 | 669 | 683 | 0.05 |

75

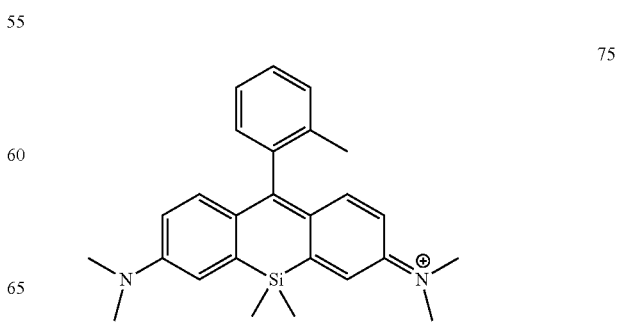

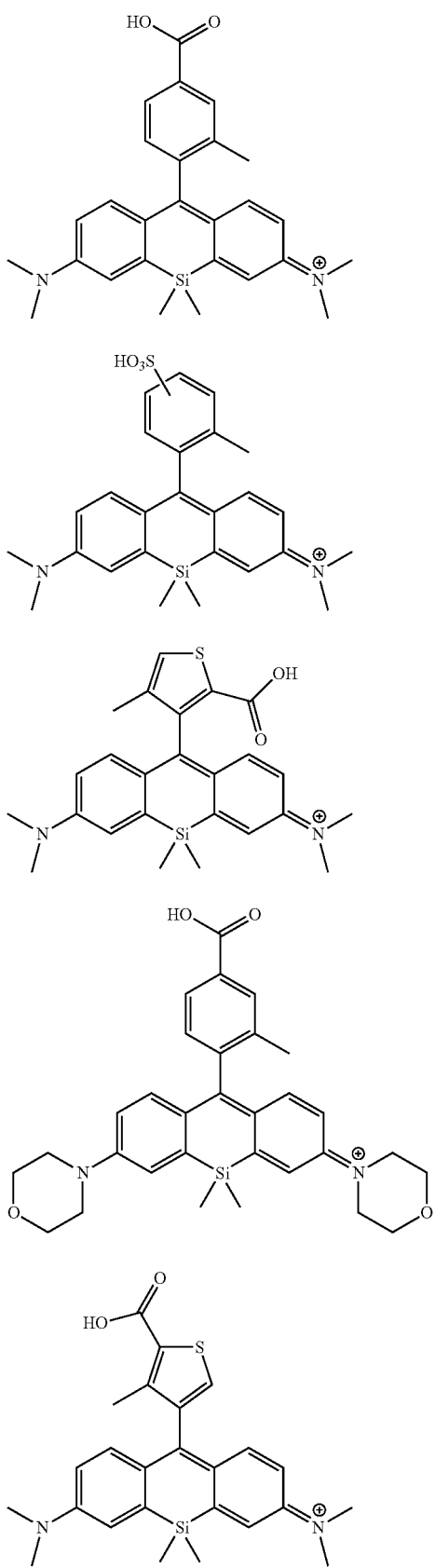
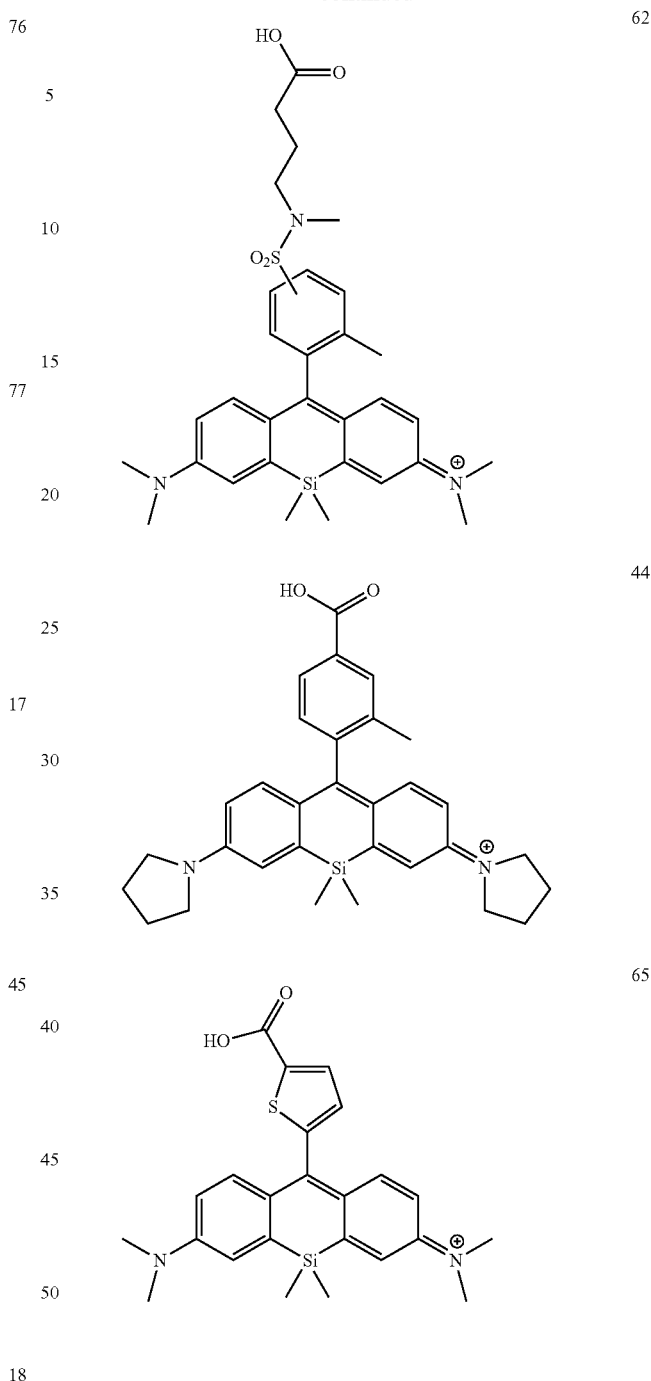

Example 10. Conjugation of a Silaxanthenium Fluorochrome Compound to a Biomolecule (Glucosamine)

Compound 44 (1 mg, 1.9 μmol) was dissolved in 100 μL of DMF and HATU (1-[Bis(dimethylamino)methylene]-1H-1,2,3-triazolo[4,5-b]pyridinium 3-oxide hexafluorophosphate, 0.75 mg, 2.0 μmol) and 0.3 μL (2.1 μmol) of triethylamine were added. After 10 minutes at room temperature, D-glucosamine hydrochloride (1 mg, 4.7 μmol) was added and the solution was allowed to react at room temperature for 2 h. The glucosamine conjugated fluorochrome compound 67 was purified by HPLC.

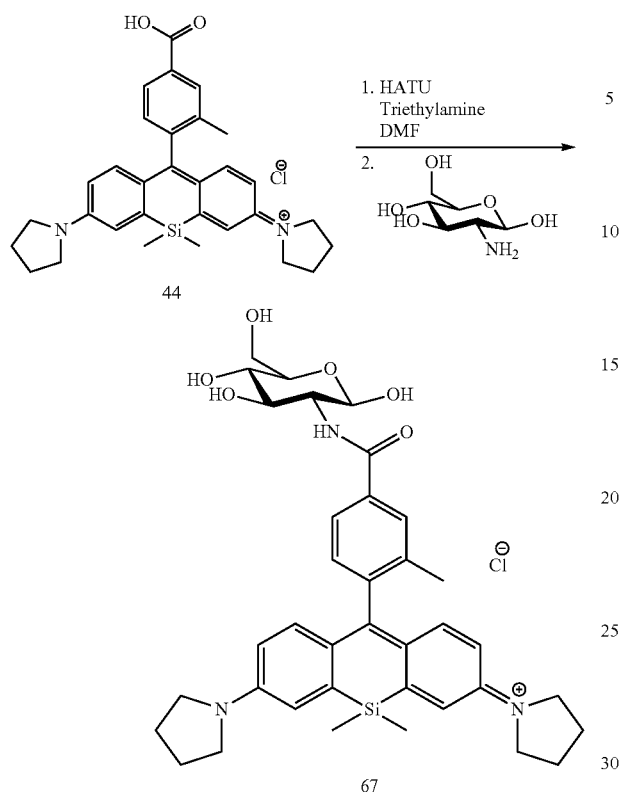

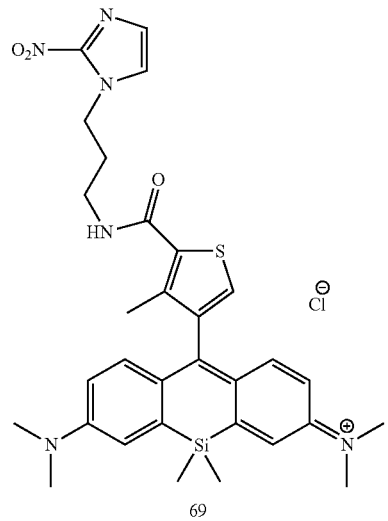

Example 11. Conjugation of a Silaxanthenium Fluorochrome Compound to a Nitroimidazole Compound 18 (1 mg, 2.1 µmol) was dissolved in 100 µL of DMF and HATU (1-[Bis(dimethylamino)methylene]-1H-1,2,3-triazolo[4,5-b]pyridinium 3-oxide hexafluorophosphate, 0.83 mg, 2.2 µmol) and 0.33 µL (2.3 µmol) of triethylamine were added. After 10 minutes at room temperature 1-(3-aminopropyl)-2-nitroimidazole (1 mg, 5.9 µmol) was added and the solution was allowed to react at room temperature for 2 h. The 2-nitroimidazole conjugated fluorochrome Compound 69 was purified by HPLC.

Example 12. Conjugation of a Silaxanthenium Fluorochrome Compound to an Antibody This example illustrates the synthesis of a reactive N-hydroxysuccinimidyl ester of a silaxanthenium fluorochrome and its subsequent use for fluorescent labeling of a biomolecule consisting of an antibody. To generate the amine reactive succinimidyl ester 64, Compound 21 (1 mg, 2.1 µmol) is dissolved in 50 µL DMF and disuccinimidyl carbonate (1 mg, 4 µmol) is added along with 1 µL of N-methylmorpholine. The reaction is allowed to proceed at room temperature for 30 minutes then the product is precipitated by the addition of 1500 µL of ether and isolated by centrifugation and decanting of the ether followed by drying under vacuum.

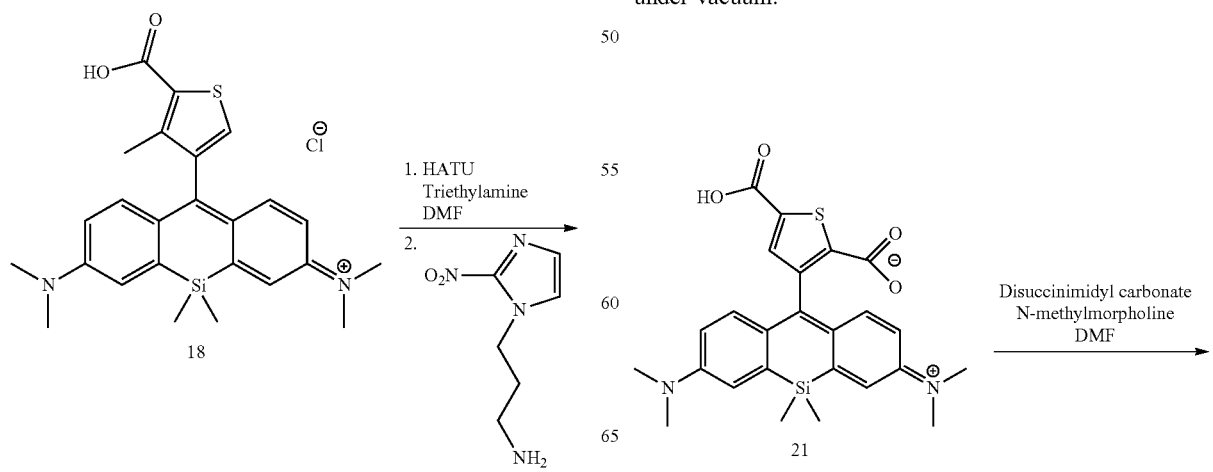

-continued

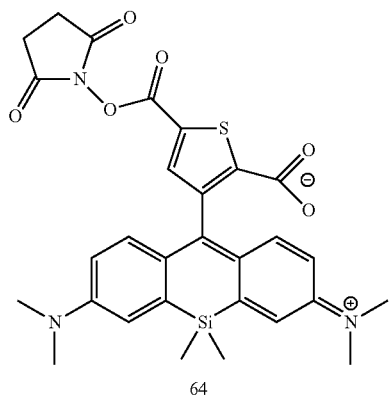

64

To label an antibody, 1 mg of Compound 64 (1.75 µmol) is dissolved in 100 µL of DMSO. 5 µL of this solution is then added to 1 mL of antibody at a concentration of 1 mg/mL in 1×PBS. 50 µL of 1 M sodium bicarbonate is added, and the solution is rotated at room temperature for 1 h. The labeled antibody is purified by size exclusion chromatography using a 10 DG column obtained from BioRad.

Example 13. Cell Uptake of Silaxanthenium Fluorochrome Compounds

Figure 2A:
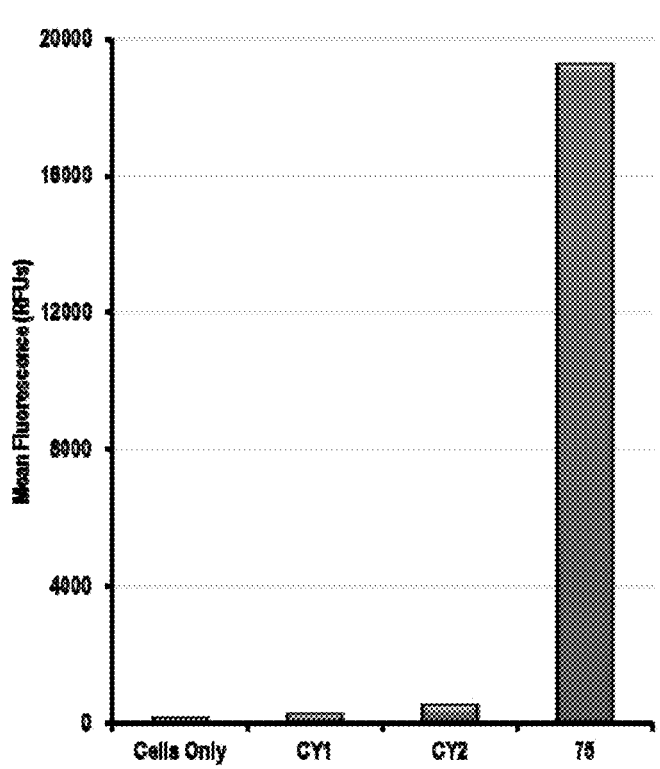
FIG. 2A is a graph showing that very low amounts of fluorescence signal were quantified in cells incubated with the two cyanine dyes CY1 and CY2, 2× and 4× the background of unlabeled cells, while the silaxanthenium dye 75 signal was 140× the background cells. After subtracting the background from unlabeled cells, 75 had 155× and 51× more fluorescence than CY1 and CY2 respectively.
Figure 2B:
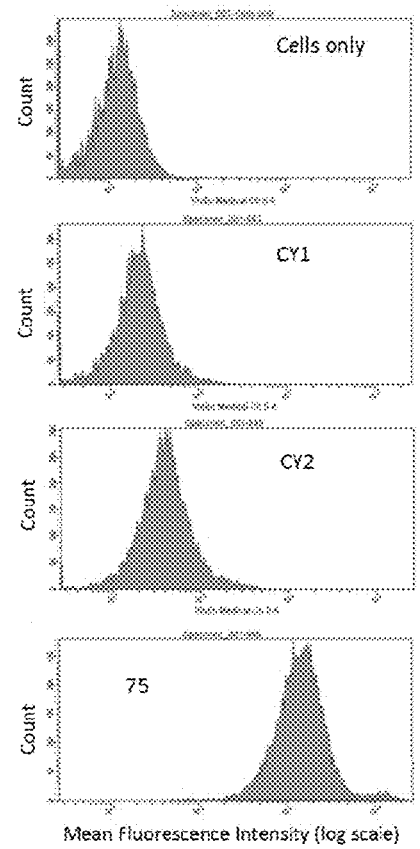
FIG. 2B shows representative histograms.

This example illustrates cell uptake by flow cytometry. HT-29 cells were incubated with 0.5 µM CY1, CY2 (common cyanine dyes of similar optical absorbance and emission wavelengths), or 75 for 5 minutes at room temperature. The cells were spun in a centrifuge then resuspended in 1×PBS for analysis by flow cytometry using a BD LSR II flow cytometer (BD Biosciences, Rockville, Md.) equipped with a solid-state 660 nm (60 mW) red laser and 712/21 nm bandpass filter. Very low amounts of fluorescence signal were quantified in cells incubated with the two cyanine dyes CY1 and CY2, 2× and 4× the background of unlabeled cells, while the silaxanthenium dye 75 signal was 140× the background cells. After subtracting the background from unlabeled cells, 75 had 155× and 51× more fluorescence than CY1 and CY2 respectively. The quantified data are shown in FIG. 2 below, along with representative histograms.

Figure 3:
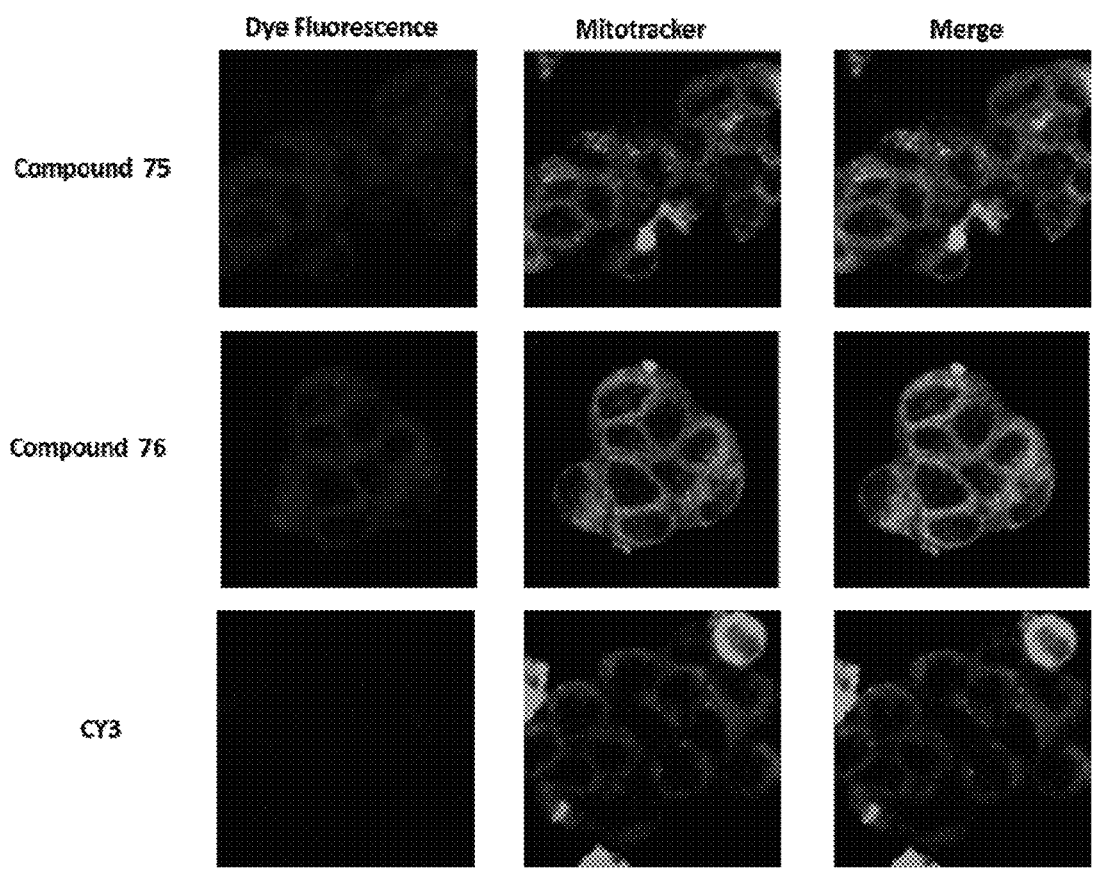
FIG. 3 shows confocal microscopy images that illustrate the uptake and intracellular localization of silaxanthenium dyes in HT-29 cells. HT-29 cells were incubated with 0.25 μM 75, 76 or CY3, a non-sulfonated cyanine dye) for 1 hour and 0.25 μM Mitotracker Green, a mitochondrial marker, for 30 minutes. The cells were washed and cytospun analyzed by confocal microscopy.

Example 14. Fluorescence Microscopy of Two Silaxanthenium Compounds and Colocalization with Mitotracker Green This example illustrates the uptake and intracellular localization of silaxanthenium dyes in HT-29 cells. HT-29 cells were incubated with 0.25 µM 75, 76 or CY3, a non-sulfonated cyanine dye) for 1 hour and 0.25 µM Mitotracker Green, a mitochondrial marker, for 30 minutes. The cells were washed and cytospun analyzed by confocal microscopy as shown in FIG. 3. Dye fluorescence is shown in blue in the first panels, Mitotracker in green in the middle panels and an overlay of the two in the third set of panels. Both SX dyes efficiently penetrated the cells and colocalized with Mitotracker. The non-sulfonated, neutral cyanine dye CY3 did not efficiently penetrate the cells under these conditions.

Example 15. Cell Uptake of a Biomolecule Conjugated SX Compound

Figure 4:
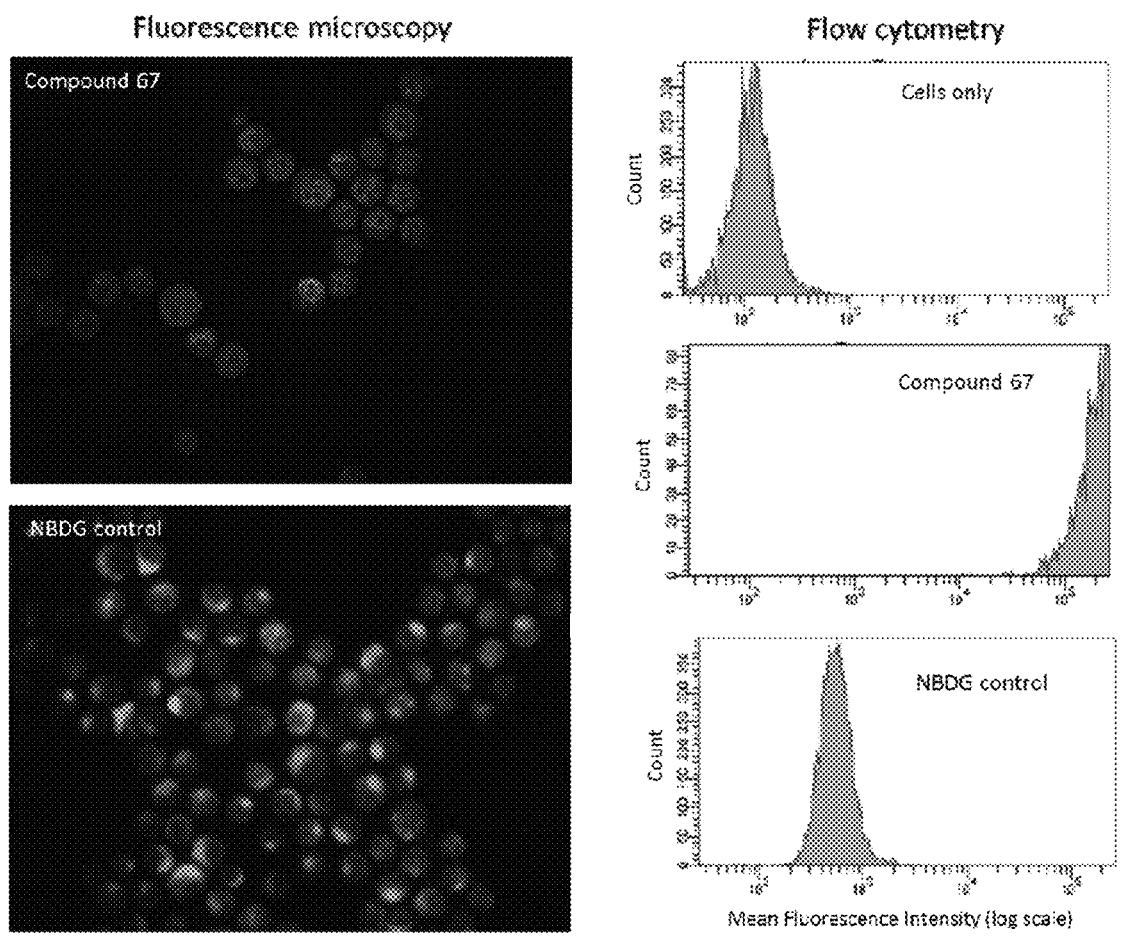
FIG. 4 depicts fluorescence microscopy images and flow cytometry quantification of the cellular uptake of a glucose conjugated silaxanthenium compound in comparison to a commercial fluorescent glucose molecule.

This example illustrates cell uptake of a biomolecule (glucosamine) conjugated SX compound, compound 67 in KB cells. KB cells were cultured in media for 2 h then incubated with 30 µM of compound 67 for 30 minutes before analysis of the cells by fluorescence microscopy and flow cytometry with appropriate filter sets for the two different fluorescent dyes. As a control, cells were also incubated with the commercial fluorescent glucosamine derivative 2-NBDG also at 30 µM. FIG. 4 shows the results of fluorescence microscopy (nuclear stain DAPI in blue, compound 67 in red and 2-NBDG in green) and flow cytometry. Both fluorescent glucosamine derivatives were taken up by the cells, however, as indicated by the histograms, quantification by flow cytometry revealed detector saturation for compound 67 while the commercial derivative 2-NBDG was in normal analysis range for the instrument and filter set. This unexpected detector saturation is indicative of very large amounts of fluorescent signal from compound 67 within the cells and is illustrative of the excellent cell permeability properties of the SX compounds of the invention.

Example 16. Cell Uptake of a Nitroimidazole Conjugated SX Compound

Figure 5:
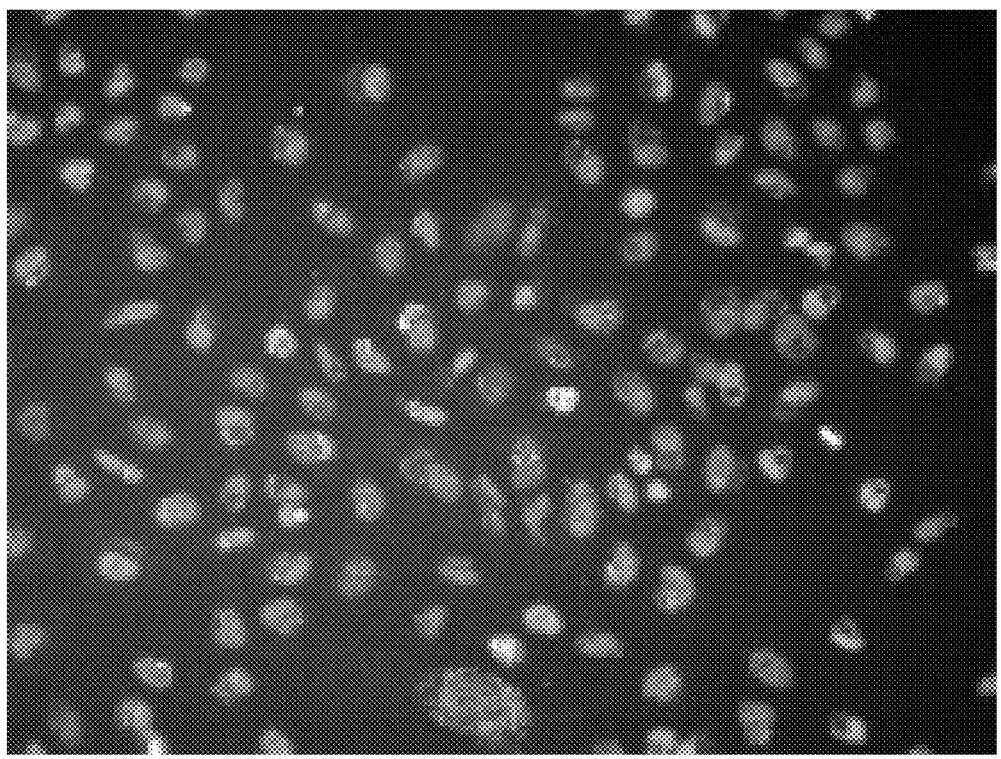
FIG. 5 depicts the uptake and localization of a nitroimidazole conjugated silaxanthenium compound 69 in HeLa cells.

This example shows uptake and localization of a nitroimidazole conjugated SX compound, compound 69 in HeLa cells. HeLa cells were seeded in a 384 well plate (5000 cells/well) and kept overnight in an incubator. The medium was removed and 0.25 µM of compound 69 in medium without serum was added. The cells were incubated for 60 minutes then the medium was exchanged with full medium and the cells were imaged on an Operetta imaging system (non-confocal, 20× high NA) with excitation and emission filters at 620-640 nm and 650-760 nm respectively. In FIG. 5, the nuclear stain DAPI is shown in blue while Compound 69 fluorescence is shown in red.

Figure 6A:
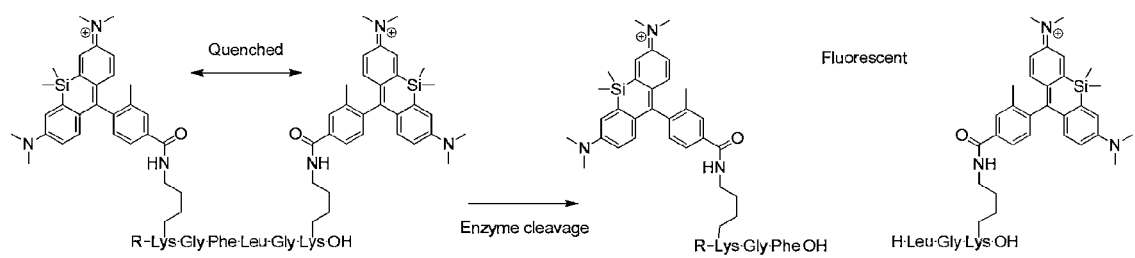
FIG. 6A illustrates fluorescence activation upon enzyme cleavage of an internally quenched pair of silaxanthenium fluorochromes separated by an enzyme cleavable peptide sequence (Compound 78).
Figure 6B:
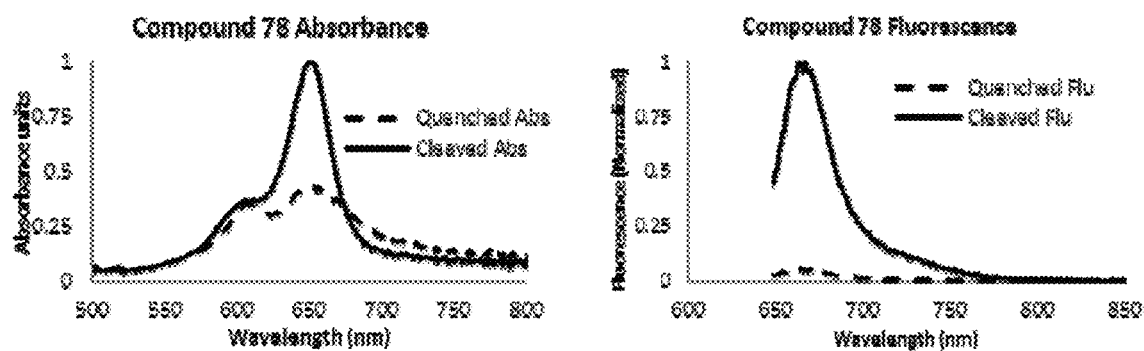
FIG. 6B shows the absorbance and emission spectra of quenched and activated silaxanthenium based probe for enzyme activity.

Example 17. Peptide-Conjugated Internally-Quenched Activatable Silaxanthenium Fluorochrome Compound FIG. 6A illustrates fluorescence activation upon enzyme cleavage of an internally quenched pair of silaxanthenium fluorochromes separated by an enzyme cleavable peptide sequence (Compound 78). Compound 78 was synthesized by conjugating two carboxylic acid dyes to lysine side chain amines in the peptide sequence using HATU and triethylamine. The quenched probe was purified by HPLC. Absorbance and fluorescence, measured on a Cary 50 UV-vis spectrophotometer (Varian) and a Cary Eclipse fluorescence spectrophotometer, respectively, of the quenched (dashed lines) and activated (cleaved by chymotrypsin in 1×PBS, solid lines) fluorochromes are shown in FIG. 6B. Fluorescence signal intensity is dramatically increased when the peptide sequence separating the two fluorochrome compounds is cleaved by an enzyme.

Example 18. In Vivo Imaging of a Silaxanthenium Fluorochrome Compound 44

Figure 7:
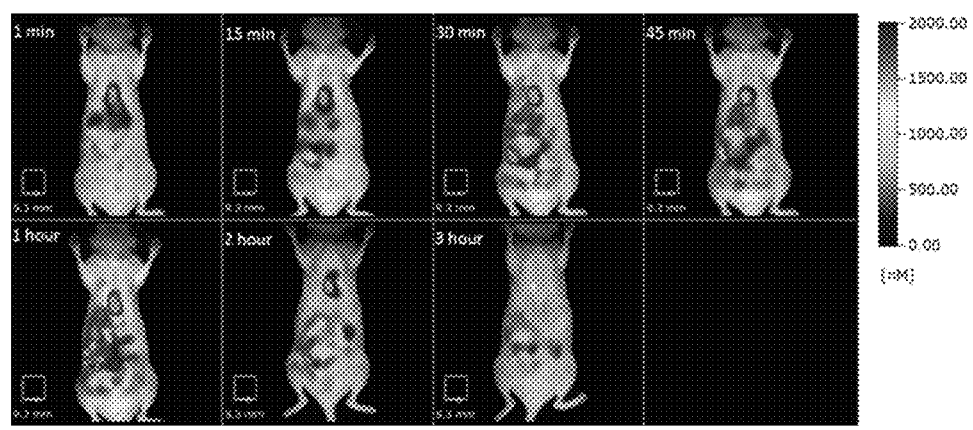
FIG. 7 demonstrates tomographic imaging by FMT 2500 tomographic in vivo imaging system (PerkinElmer, Waltham, Mass.) of a fluorochrome compound of the present invention after intravenous injection.

FIG. 7 demonstrates tomographic imaging by FMT 2500 tomographic in vivo imaging system (PerkinElmer, Waltham, Mass.) of a fluorochrome compound of the present invention after intravenous injection of Compound 44 into live mice. Two SKH-1 E female mice (9 weeks old) were injected with 2 nmoles of compound 44. Tomographic images of the whole body of the mouse were taken at 1, 15, 30 and 45 minutes and 1, 2 and 3 hours. Rapid accumulation of the fluorochrome compound can be seen in the heart region followed by slower accumulation to other areas of the body with wash out of the untargeted compound by 3 h, representing a window for in vivo imaging.

Example 19. Synthesis of a Carbonic Anhydrase Targeted Silaxthenium Compound 73

Compound 20 (0.5 mg, 1.0 µmol) was dissolved in 100 µL of DMF and HATU (1-[Bis(dimethylamino)methylene]-1H-1,2,3-triazolo[4,5-b]pyridinium 3-oxide hexafluorophosphate, 0.83 mg, 2.2 µmol) and 0.33 µL (2.3 µmol) of N-methylmorpholine were added. After 30 minutes at room temperature 4-(aminomethyl)benzenesulfonamide (1 mg, 5.4 µmol) was added and the solution was allowed to react at room temperature for 2 h. The 2-nitroimidazole conjugated fluorochrome Compound 73 was purified by HPLC.

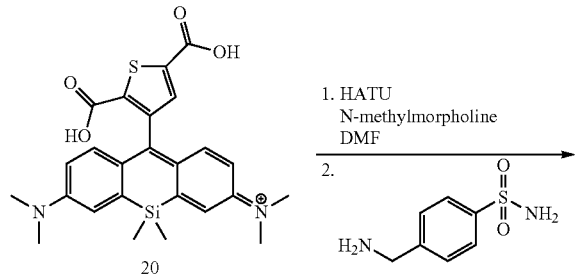

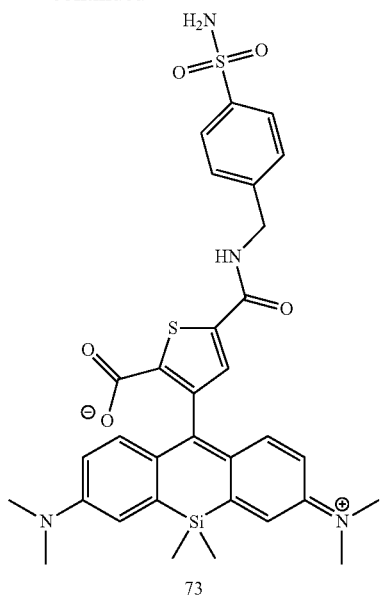

Example 20. Synthesis of a 4-Hydroxycinnamamide Derivatized Silaxthenium Compound 74

Compound 20 (0.5 mg, 1.0 µmol) was dissolved in 100 µL of DMF and HATU (1-[Bis(dimethylamino)methylene]-1H-1,2,3-triazolo[4,5-b]pyridinium 3-oxide hexafluorophosphate, 0.83 mg, 2.2 µmol) and 0.33 µL (2.3 µmol) of N-methylmorpholine were added. After 30 minutes at room temperature N-(2-aminoethyl)-4-hydroxycinnamamide (1 mg, 5 µmol) was added and the solution was allowed to react at room temperature for 2 h. The 2-nitroimidazole conjugated fluorochrome Compound 74 was purified by HPLC.

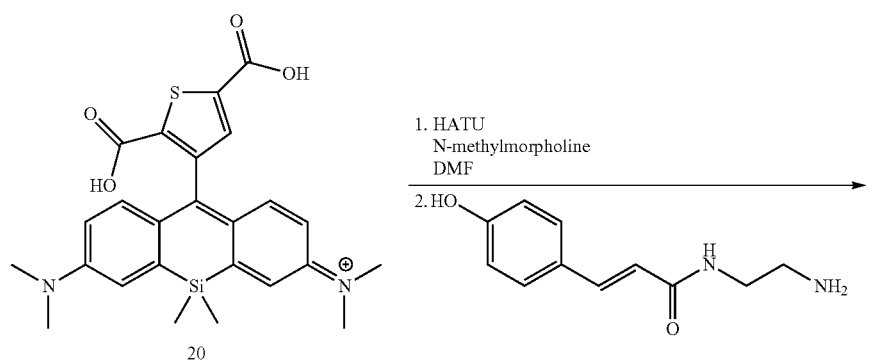

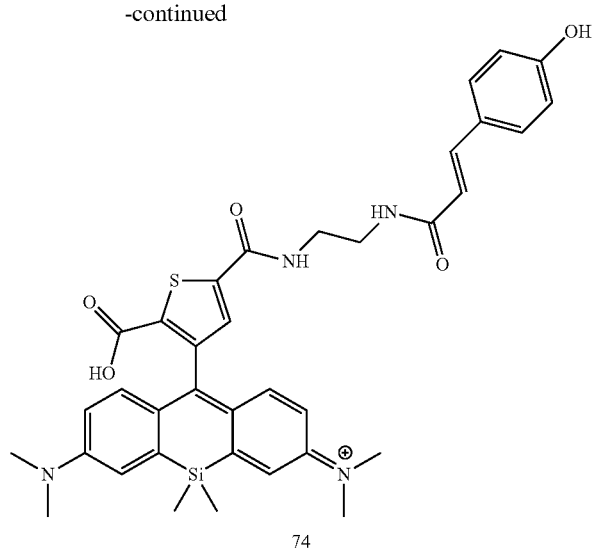

Example 21. Synthesis of a Acetazolamide Conjugated Silaxthenium Compound 75

Compound 20 (0.5 mg, 1.0 μmol) was dissolved in 100 μL of DMF and HATU (1-[Bis(dimethylamino)methylene]-1H-1,2,3-triazolo[4,5-b]pyridinium 3-oxide hexafluorophosphate, 0.83 mg, 2.2 μmol) and 0.33 μL (2.3 μmol) of N-methylmorpholine were added. After 30 minutes at room temperature 4-(aminomethyl)-N-(5-sulfamoyl-1,3,4-thiadiazol-2-yl)benzamide (1.5 mg, 4.8 μmol) was added and the solution was allowed to react at room temperature for 2 h. The 2-nitroimidazole conjugated fluorochrome Compound 75 was purified by HPLC.

Example 22. Synthesis of a (4-Aminoethyl)Benzenesulfonamide Derivatized Silaxthenium Compound 76

Compound 20 (0.5 mg, 1.0 μmol) was dissolved in 100 μL of DMF and HATU (1-[Bis(dimethylamino)methylene]-1H-1,2,3-triazolo[4,5-b]pyridinium 3-oxide hexafluorophosphate, 0.83 mg, 2.2 μmol) and 0.33 μL (2.3 μmol) of N-methylmorpholine were added. After 30 minutes at room temperature 4-(aminoethyl)benzenesulfonamide (1 mg, 5.0 μmol) was added and the solution was allowed to react at room temperature for 2 h. The 2-nitroimidazole conjugated fluorochrome Compound 76 was purified by HPLC.

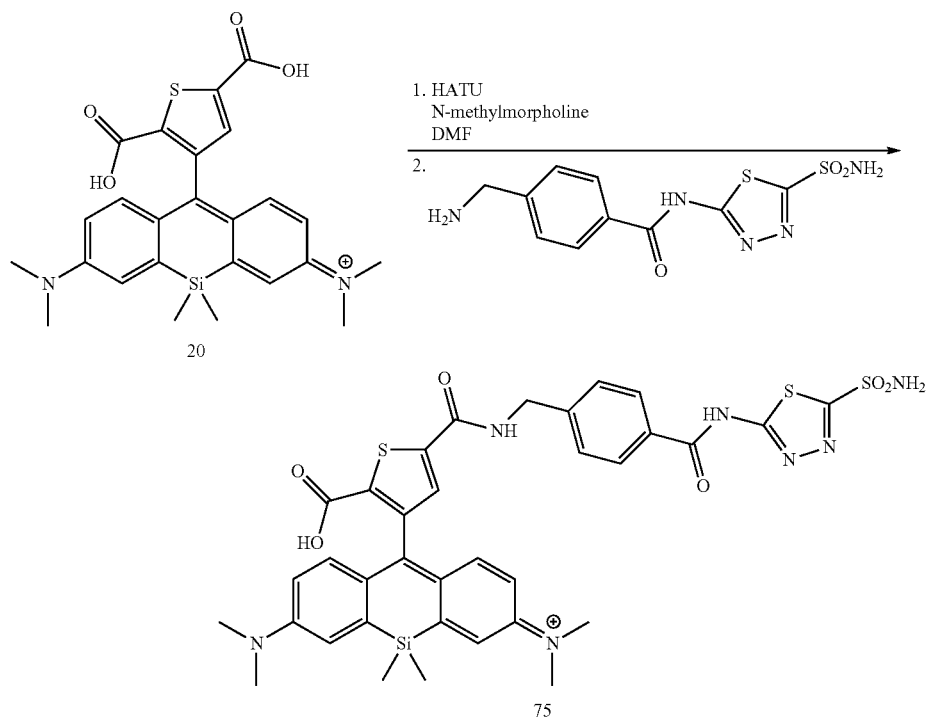

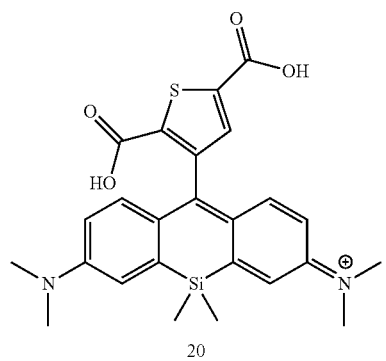

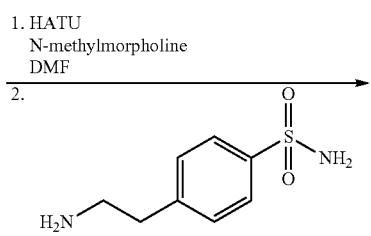

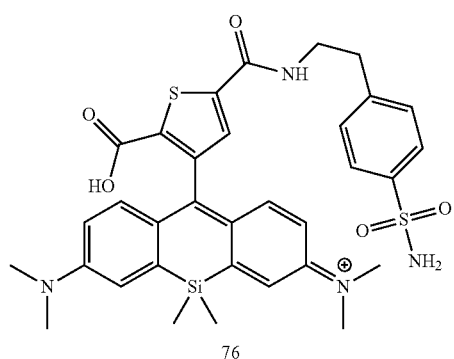

Example 23. Synthesis of an Indomethacin Conjugated (COX-2 Targeted) Silaxthenium Compound 78

Compound 20 (0.5 mg, 1.0 µmol) was dissolved in 100 µL of DMF and HATU (1-[Bis(dimethylamino)methylene]-1H-1,2,3-triazolo[4,5-b]pyridinium 3-oxide hexafluorophosphate, 0.83 mg, 2.2 µmol) and 0.33 µL (2.3 µmol) of N-methylmorpholine were added. After 30 minutes at room temperature (4-aminobutyl)indomethacin carboxamide (2 mg, 4.7 µmol) was added and the solution was allowed to react at room temperature for 2 h. The 2-nitroimidazole conjugated fluorochrome Compound 78 was purified by HPLC.

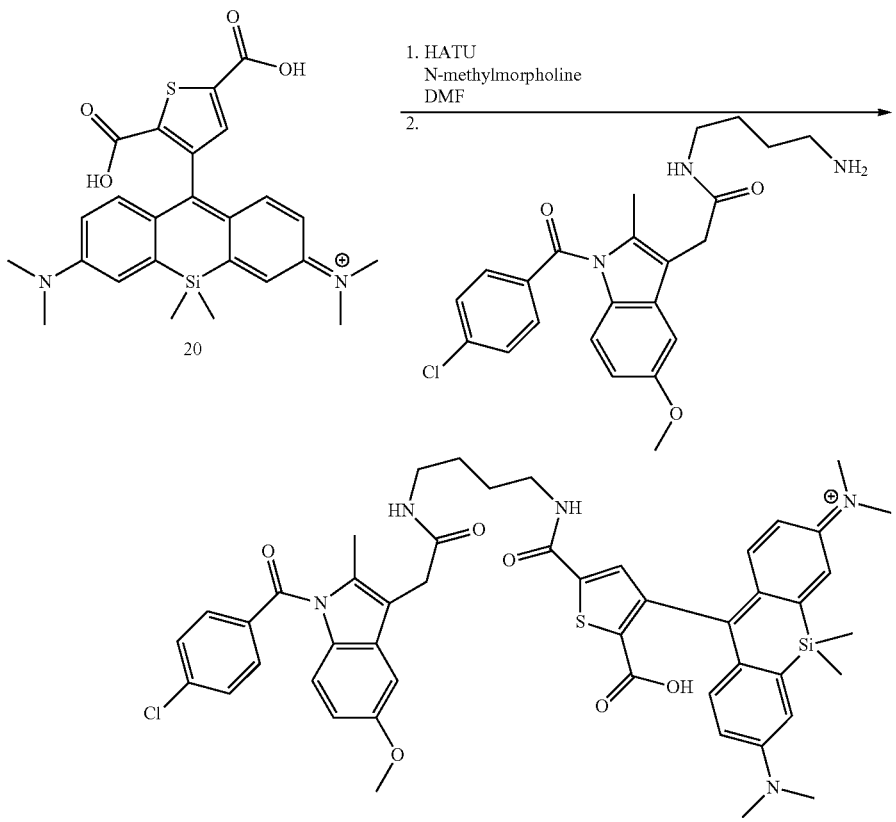

Figure 8:
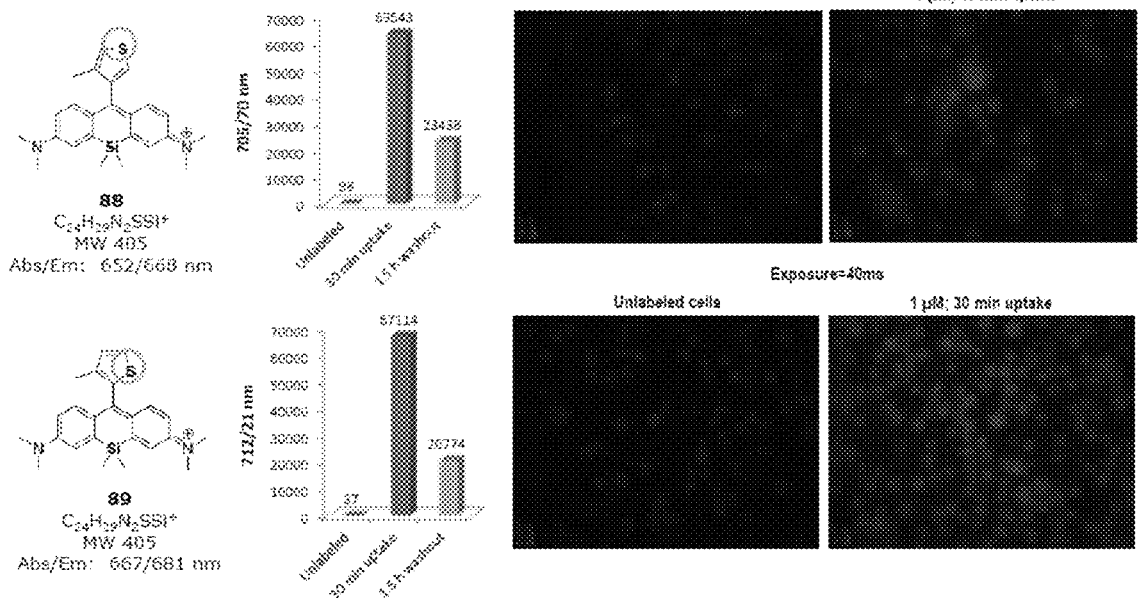
FIG. 8 depicts the cellular uptake and washout of two isomeric 9-thienylsilaxanthenium compounds with different wavelength profiles in 4T1 cells by flow cytometry and fluorescence microscopy.

Example 24. Cell Uptake by Microscopy and Flow Cytometry of Two 9-Thienylsilaxanthene Fluorochromes with Identical Empirical Formulae but Different Wavelength Characteristics Two isomeric thienyl Si-Rho dyes 88 and 89, were synthesized using the methods described previously. The two isomeric compounds, which are of identical molecular weight and molecular formula, have absorption and emission maxima of 652 nm and 668 nm (88) and 667 nm and 681 nm (89). Compounds were analyzed with two different filter sets by flow cytometry and also by fluorescence microscopy for cellular uptake and washout. Trypsin EDTA-detached 4T1 at 0.5 mil cells/mL culture medium were incubated with 1 uM 88 or 89 for 30 min at 37° C. Cells were washed 1× with PBS and analyzed by flow cytometry with a 705/70 nm emission filter for 88 and a 712/21 nm emission filter for 89 and by fluorescence microscopy. Significant uptake of both dyes was observed, with approximately one third of the dye still remaining after 1.5 h washout as quantified by flow cytometry (FIG. 8).

Figure 9A:
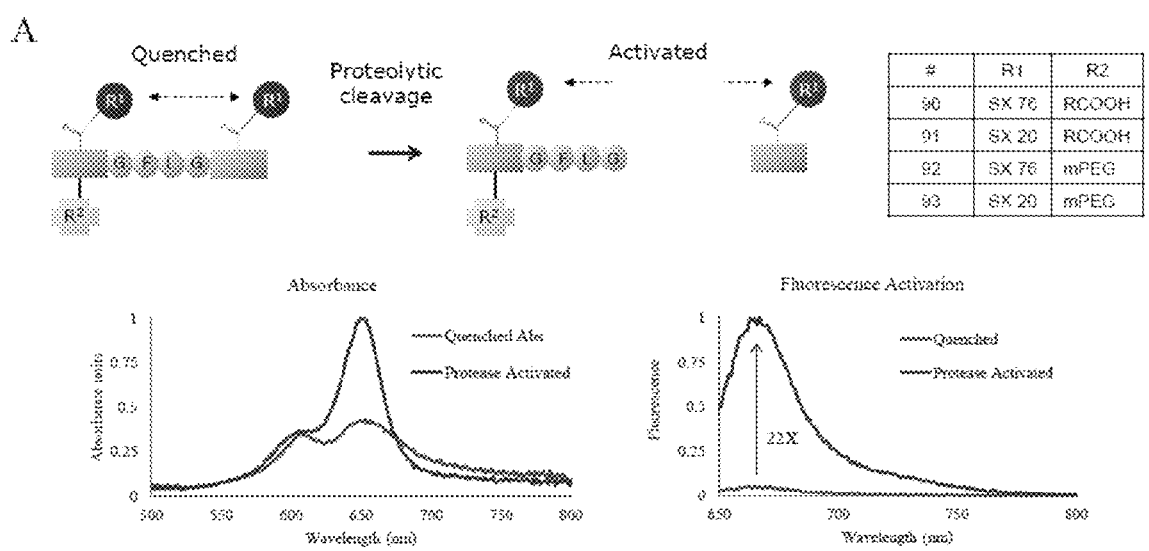
FIG. 9A shows protease activation of activatable thienyl compound 91.
Figure 9B:
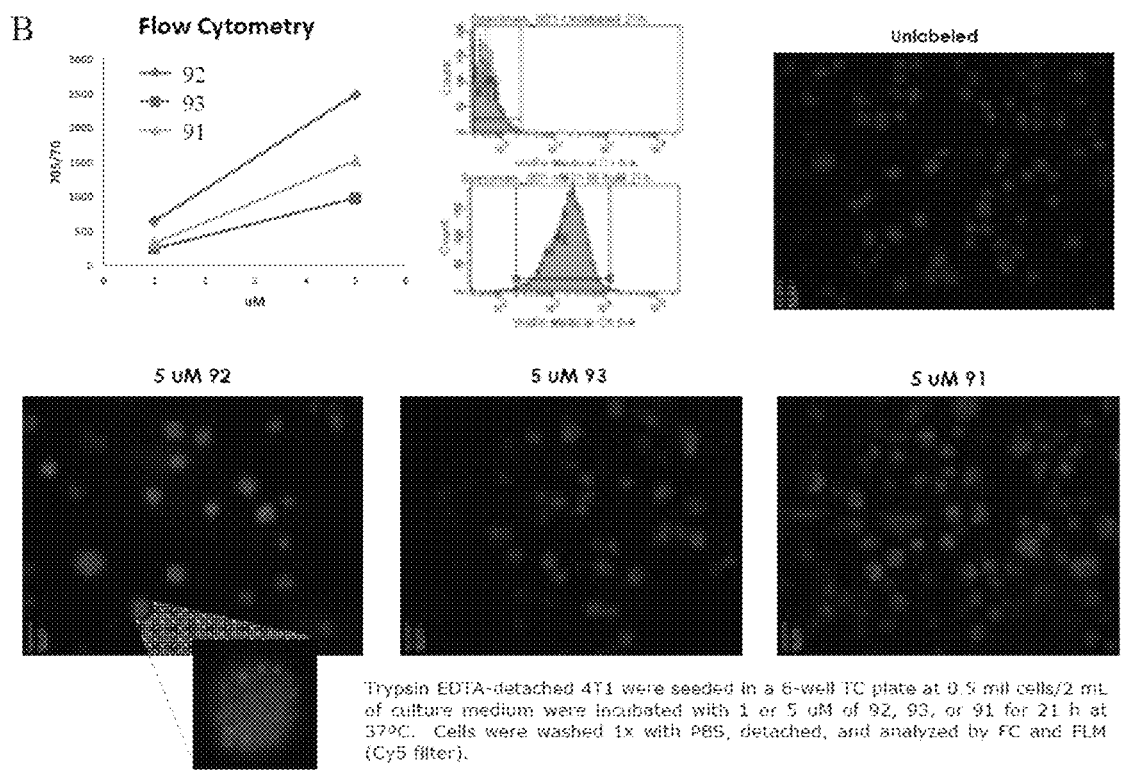
FIG. 9B shows uptake and activation of several enzyme-activatable silaxanthenium compounds 92, 93 and 91 in live cells by flow cytometry and fluorescence microscopy.
Figure 9C:
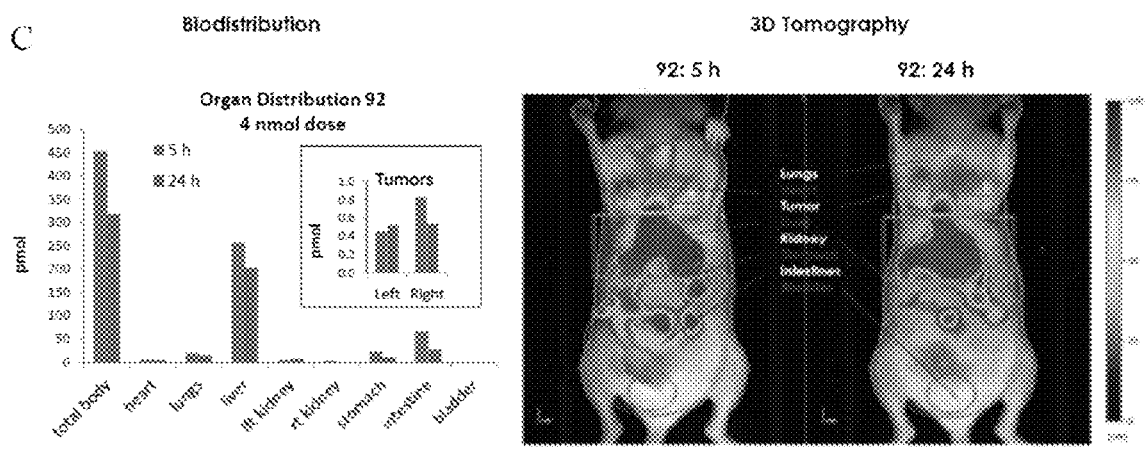
FIG. 9C shows the in vivo activation and biodistribution of compound 92 in live mice as imaged tomographically by FMT.

Example 25. In Vitro and In Vivo Characterization of Several Activatable SX Derivatives FIG. 9A shows representative protease activation of activatable thienyl compound 91 (by chymotrypsin) in 1×PBS at 37° C. for 4 h. A 22-fold increase in fluorescence intensity was observed. FIG. 9B shows uptake and activation of compounds 92, 93 and 91 in live cells by flow cytometry and fluorescence microscopy. Trypsin EDTA-detached 4T1 were seeded in a 6-well tissue culture plate at 0.5 mil cells/2 mL of culture medium were incubated with 1 or 5 uM of 92, 93, or 91 for 21 h at 37° C. Cells were washed 1× with PBS, detached, and analyzed by FC and FLM (Cy5 filter). FIG. 9C shows the in vivo activation and biodistribution of compound 92 in live mice as imaged tomographically by FMT. Trypsin EDTA-detached 4T1 cells were implanted 1.5 mil/site approximately 1 week prior to imaging. 92 was injected retro-orbitally at 4 nmol and imaged by FMT at 5 and 24 h. Activation of the quenched silaxanthenium agent was detected in vivo in tumors, liver and gut, demonstrating the ability of activatable silaxanthenium compounds to be used for quantitative in vivo imaging.

INCORPORATION BY REFERENCE

All publications, patents, and patent applications cited herein are hereby expressly incorporated by reference in their entirety and for all purposes to the same extent as if each was so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:
1. A compound represented by Formula I:

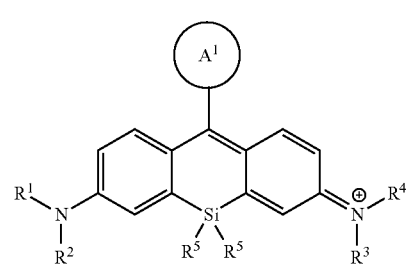

(I)

or a salt thereof wherein:
$A^1$ is phenyl substituted with 1, 2, or 3 substituents independently selected from the group consisting of hydroxyl, —$CO_2$-(optionally substituted heterocycloalkyl), —$N(R^6)C(O)(R^7)$, alkylene-(optionally substituted heterocyclyl), nitro, alkylene-O-alkylene-$CO_2H$, alkylene-O-alkylene-$CO_2^-$, —$SO_2$—$N(R^6)$-alkylene-$CO_2H$, —$SO_2$—$N(R^6)$-alkylene-$CO_2^-$, —$N(R^6)$—$SO_2$-alkylene-$CO_2H$, —$N(R^6)$—$SO_2$-alkylene-$CO_2^-$, —$SO_2$—$N(R^6)$-(optionally substituted heterocycloalkyl), —$SO_2$—$N(R^6)_2$, —$SO_2$—$N(R^6)$-alkylene-(optionally substituted heterocyclyl); or $A^1$ is a 5-6 membered heteroaryl, optionally substituted with 1, 2, or 3 substituents independently selected from the group consisting of alkyl, haloalkyl halogen, hydroxyl, alkoxy, —$CO_2H$, —$CO_2^-$, —$CO_2$-(optionally substituted heterocycloalkyl), —$C(O)N(R^6)(R^7)$, —$N(R^6)C(O)(R^7)$, alkylene-(optionally substituted heterocyclyl), nitro, alkylene-O-alkylene-$CO_2H$, alkylene-O-alkylene-$CO_2^-$, —$SO_2$—$N(R^6)$-alkylene-$CO_2H$, —$SO_2$—$N(R^6)$-alkyne-$CO_2^-$, —$N(R^6)$—$SO_2$-alkylene-$CO_2H$, —$N(R^6)$—$SO_2$-alkylene-$CO_2^-$, —$SO_2$—$N(R^6)$-(optionally substituted heterocycloalkyl), —$SO_2$—$N(R^6)_2$, —$SO_2$—$N(R^6)$-alkylene-(optionally substituted heterocyclyl), $X^1$, and alkylene-$X^1$;

$X^1$ represents independently for each occurrence a maleimide, a succinimidyl ester, a carboxamide, propargyl, azidoalkyl, isothiocyanate, —$NH_2$—OH, —SH, —$SO_3H$, carboxyl, —C(O)Cl, —(CO)O(CO)$R^8$, —CON(H)$NH_2$, an acetoxymethyl ester, a substituted or unsubstituted N-hydroxysuccinimidyl ester, a substituted or unsubstituted N-hydroxysulfosuccinimido ester, a nitro-phenol ester, a fluoro-phenol ester, azide, —NCS, —CHO, —COCH$_2$I, a phosphoramidite, or a phthalamido;

$R^1$ and $R^2$ each represent independently hydrogen, alkyl, cycloalkyl, heterocycloalkyl, or —$C(O)N(R^6)$(optionally substituted alkyl); or $R^1$ and $R^2$ are taken together with the nitrogen atom to which they are attached to form a monocyclic or bicyclic ring;

$R^3$ and $R^4$ each represent independently hydrogen, alkyl, cycloalkyl, heterocycloalkyl, or —$C(O)N(R^6)$(optionally substituted alkyl); or $R^3$ and $R^4$ are taken together with the nitrogen atom to which they are attached to form a monocyclic or bicyclic ring;

$R^5$ represents independently for each occurrence $C_{1-6}$ alkyl;

$R^6$ represents independently for each occurrence hydrogen or alkyl;

R⁷ represents independently for each occurrence hydrogen, alkyl, alkylene-CO₂H, alkylene-C(O)N(R⁶)₂, alkylene-(optionally substituted heterocyclyl), optionally substituted heterocyclyl, alkylene-(optionally substituted heteroaryl), or hydroxyl alkylene-(optionally substituted heterocyclyl); and R⁸ represents independently for each occurrence hydrogen, alkyl, or aryl.

2. The compound of claim 1, wherein A¹ is a 5-6 membered heteroaryl optionally substituted with 1, 2, or 3 substituents independently selected from the group consisting of alkyl, haloalkyl, halogen, hydroxyl, alkoxy, —CO₂H, —CO₂⁻, —CO₂-(optionally substituted heterocycloalkyl), —C(O)N(R⁶)(R⁷), —N(R⁶)C(O)(R⁷) alkylene-(optionally substituted heterocyclyl), nitro, alkylene-O-alkylene-CO₂H, alkylene-O-alkylene-CO₂⁻, —SO₂—N(R⁶)-alkylene-CO₂H, —SO₂—N(R⁶)-alkylene-CO₂⁻, —N(R⁶)—SO₂-alkylene-CO₂H, —N(R⁶)—SO₂-alkylene-CO₂⁻, —SO₂—N(R⁶)-(optionally substituted heterocycloalkyl), —SO₂—N(R⁶)₂, and —SO₂—N(R⁶)-alkylene-(optionally substituted heterocyclyl).

3. The compound of claim 1, wherein A¹ is thiophenyl, furanyl, or pyridinyl, each of which is optionally substituted with 1, 2, or 3 substituents independently selected from the group consisting of alkyl, haloalkyl, halogen, hydroxyl, alkoxy, —CO₂H, —CO₂⁻, —CO₂-(optionally substituted heterocycloalkyl), —C(O)N(R⁶)(R⁷), —N(R⁶)C(O)(R⁷), alkylene-(optionally substituted heterocyclyl), nitro, alkylene-O-alkylene-CO₂H, alkylene-O-alkylene-CO₂⁻, —SO₂—N(R⁶)-alkylene-CO₂H, —SO₂—N(R⁶)-alkylene-CO₂⁻, —N(R⁶)—SO₂-alkylene-CO₂H, —N(R⁶)—SO₂-alkylene-CO₂⁻, —SO₂—N(R⁶)-(optionally substituted heterocycloalkyl), —SO₂—N(R⁶)₂, and —SO₂—N(R⁶)-alkylene-(optionally substituted heterocyclyl).

4. The compound of claim 1, wherein A¹ is phenyl substituted with 1, 2, or 3 substituents independently selected from the group consisting of hydroxyl, —CO₂-(optionally substituted heterocycloalkyl), —N(R⁶)C(O)(R⁷), alkylene-(optionally substituted heterocyclyl) nitro, alkylene-O-alkylene-CO₂H, alkylene-O-alkylene-CO₂⁻, —SO₂—N(R⁶)-alkylene-CO₂H, —SO₂—N(R⁶)-alkylene-CO₂⁻, —N(R⁶)—SO₂-alkylene-CO₂H, —N(R⁶)₂—SO₂-alkylene-CO₂⁻, —SO₂—N(R⁶)-(optionally substituted heterocycloalkyl), —SO₂—N(R⁶)₂, and —SO₂—N(R⁶)-alkylene-(optionally substituted heterocyclyl).

5. The compound of claim 1, wherein R¹ and R² each represent independently hydrogen or alkyl; or R¹ and R² are taken together with the nitrogen atom to which they are attached to form a 4-6 membered, saturated heterocyclic ring.

6. The compound of claim 1, wherein R³ and R⁴ each represent independently hydrogen or alkyl; or R³ and R⁴ are taken together with the nitrogen atom to which they are attached to form a 4-6 membered, saturated heterocyclic ring.

7. The compound of claim 1, wherein R⁶ is methyl.

8. The compound of claim 1, wherein R⁶ is hydrogen.

9. The compound of claim 1, wherein R⁷ represents independently for each occurrence hydrogen, alkyl, alkylene-CO₂H, or alkylene-C(O)N(R⁶)₂.

10. The compound of claim 1, wherein the compound is a compound presented in Table 1 or 2 herein or a pharmaceutically acceptable salt thereof.

11. The compound of claim 1, wherein the compound has an absorption and emission wavelength in the range from about 500 nm to about 1100 nm.

12. The compound of claim 1, wherein the compound has an absorption and emission wavelength in the range from about 500 nm to about 600 nm.

13. A conjugate compound that is a compound of Formula I substituted with 1, 2, or 3 groups defined by -L-BM; wherein L is a bond or a linker, -BM is a radical of a biological molecule, and Formula I is represented by:

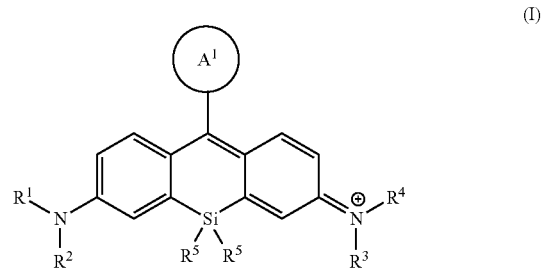

(I)

or a salt thereof, wherein:

A¹ is phenyl substituted with 1, 2, or 3 substituents independently selected from the group consisting of hydroxyl, —CO₂-(optionally substituted heterocycloalkyl), —N(R⁶)C(O)(R⁷), alkylene-(optionally substituted heterocyclyl), nitro, alkylene-O-alkylene-CO₂H, alkylene-O-alkylene-CO₂⁻, —SO₂—N(R⁶)-alkylene-CO₂H, —SO₂—N(R⁶)-alkylene-CO₂⁻, —N(R⁶)—SO₂-alkylene-CO₂H, —N(R⁶)—SO₂-alkylene-CO₂⁻, —SO₂—N(R⁶)-(optionally substituted heterocycloalkyl), —SO₂—N(R⁶)₂, —SO₂—N(R⁶)-alkylene-(optionally substituted heterocyclyl); or A¹ is a 5-6 membered heteroaryl, optionally substituted with 1, 2, or 3 substituents independently selected from the group consisting of alkyl, haloalkyl, halogen, hydroxyl, alkoxy, —CO₂H, —CO₂⁻, —CO₂-(optionally substituted heterocycloalkyl), —C(O)N(R⁶)(R⁷), —N(R⁶)C(O)(R⁷), alkylene-(optionally substituted heterocyclyl), nitro, alkylene-O-alkylene-CO₂H, alkylene-O-alkylene-CO₂⁻, —SO₂—N(R⁶)-alkylene-CO₂H, —SO₂—N(R⁶)-alkylene-CO₂⁻, —N(R⁶)—SO₂-alkylene-CO₂H, —N(R⁶)—SO₂-alkylene-CO₂⁻, —SO₂—N(R⁶)-(optionally substituted heterocycloalkyl), —SO₂—N(R⁶)₂, —SO₂—N(R⁶)-alkylene-(optionally substituted heterocyclyl), X¹, and alkylene-X¹;

X¹ represents independently for each occurrence a maleimide, a succinimidyl ester, a carboxamide, propargyl, azidoalkyl, isothiocyanate, —NH₂—OH, —SH, —SO₃H, carboxyl, —C(O)Cl, —(CO)O(CO)R⁸, —CON(H)NH₂, an acetoxymethyl ester, a substituted or unsubstituted N-hydroxysuccinimidyl ester, a substituted or unsubstituted N-hydroxysulfosuccinimido ester, a nitro-phenol ester, a fluoro-phenol ester, azide, —NCS, —CHO, —COCH₂I, a phosphoramidite, or a phthalamido;

R¹ and R² each represent independently hydrogen, alkyl, cycloalkyl, heterocycloalkyl, or —C(O)N(R⁶)(optionally substituted alkyl); or R¹ and R² are taken together with the nitrogen atom to which they are attached to form a monocyclic or bicyclic ring;

R³ and R⁴ each represent independently hydrogen, alkyl, cycloalkyl, heterocycloalkyl, or —C(O)N(R⁶)(optionally substituted alkyl); or R³ and R⁴ are taken together with the nitrogen atom to which they are attached to form a monocyclic or bicyclic ring;

R⁵ represents independently for each occurrence C₁₋₆ alkyl;

R⁶ represents independently for each occurrence hydrogen or alkyl;

R⁷ represents independently for each occurrence hydrogen, alkyl, alkylene-CO₂H, alkylene-C(O)N(R⁶)₂, alkylene-(optionally substituted heterocyclyl), optionally substituted heterocyclyl, alkylene-(optionally substituted heteroaryl), or hydroxyl alkylene-(optionally substituted heterocyclyl); and R⁸ represents independently for each occurrence hydrogen, alkyl, or aryl.

14. A conjugate compound represented by Formula II:

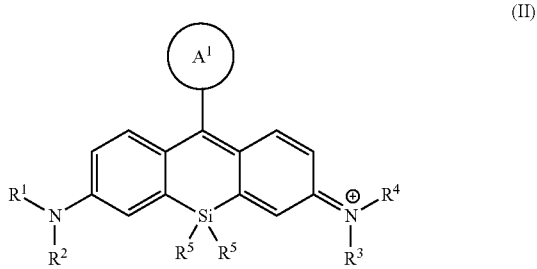

(II)

or a salt thereof; wherein:
A¹ is phenyl substituted with 1, 2, or 3 substituents independently selected from the group consisting of —C(O)-ψ, alkylene-C(O)-ψ, alkylene-C(O)N(R⁶)-ψ, —N(R⁶)C(O)-ψ, alkylene-C(O)-ψ, alkylene-N(R⁶)C(O)-ψ, hydroxyl, —CO₂-(optionally substituted heterocycloalkyl), —N(R⁶)C(O)(R⁷), alkylene-(optionally substituted heterocyclyl), nitro, alkylene-O-alkylene-CO₂H, alkylene-O-alkylene-CO₂⁻, —SO₂—N(R⁶)-alkylene-CO₂H, —SO₂—N(R⁶)-alkylene-CO₂⁻, —N(R⁶)—SO₂-alkylene-CO₂H, N(R⁶)—SO₂-alkylene-CO₂⁻, —SO₂—N(R⁶)-(optionally substituted heterocycloalkyl), —SO₂—N(R⁶)₂, and —SO₂—N(R⁶)-(alkylene-(optionally substituted heterocyclyl); or
A¹ is a 5-6 membered heteroaryl, optionally substituted with 1, 2, or 3 substituents independently selected from the group consisting of —C(O)-ψ, —C(O)N(R⁶)-ψ, alkylene-C(O)-ψ, alkylene-C(O)N(R⁶)-ψ, —N(R⁶)C(O)-ψ, alkylene-C(O)-ψ, alkylene-N(R⁶)C(O)-ψ, alkyl, haloalkyl, halogen, hydroxyl, alkoxy, —CO₂H, —CO₂⁻, —CO₂-(optionally substituted heterocycloalkyl), —C(O)N(R⁶)(R⁷), —N(R⁶)C(O)(R⁷), alkylene-(optionally substituted heterocyclyl), nitro, alkylene-O-alkylene-CO₂H, alkylene-O-alkylene-CO₂⁻, —SO₂—N(R⁶)-alkylene-CO₂H, —SO₂—N(R⁶)-alkylene-CO₂⁻, —N(R⁶)—SO₂-alkylene-CO₂H, N(R⁶)—SO₂-alkylene-CO₂⁻, —SO₂—N(R⁶)-(optionally substituted heterocycloalkyl), —SO₂—N(R⁶)₂, and —SO₂—N(R⁶)alkylene-optionally substituted heterocyclyl);
Ψ is a radical of a biological molecule;
R¹ and R² each represent independently hydrogen, alkyl, cycloalkyl, heterocycloalkyl, or —C(O)N(R⁶)(optionally substituted alkyl); or R¹ and R² are taken together with the nitrogen atom to which they are attached to form a monocyclic or bicyclic ring;
R³ and R⁴ each represent independently hydrogen, alkyl, cycloalkyl, heterocycloalkyl, or —C(O)N(R⁶)(optionally substituted alkyl); or R³ and R⁴ are taken together with the nitrogen atom to which they are attached to form a monocyclic or bicyclic ring;
R⁵ represents independently for each occurrence C₁₋₆ alkyl;
R⁶ represents independently for each occurrence hydrogen or alkyl; and
R⁷ represents independently for each occurrence hydrogen, alkyl, alkylene-CO₂H, alkylene-C(O)N(R⁶)₂, alkylene-(optionally substituted heterocyclyl) optionally substituted heterocyclyl, alkylene-(optionally substituted heteroaryl), or hydroxyl alkylene-(optionally substituted heterocyclyl).

15. The conjugate compound of claim 13 or 14, wherein the biological molecule is a protein, glycoprotein, peptide, amino acid, lipid, polysaccharide, carbohydrate, nucleoside, nucleotide, vitamin, nucleic acid, or a cell.

16. A compound represented by Formula III:

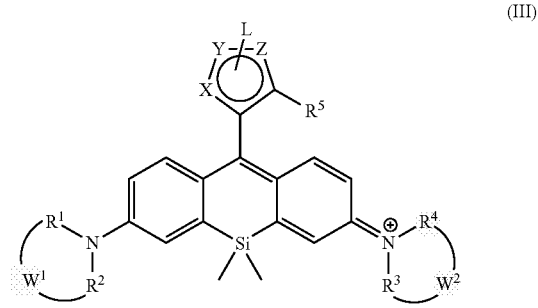

(III)

or a salt thereof, wherein:
X, Y and Z are, independently, O, S, N, Si, C or (C=C);
L is absent or is a linker moiety, optionally bearing a functional group or reactive group selected from a carboxylate, carboxyalkyl, maleimide, succinimidyl ester, carboxamide, propargyl, azidoalkyl, isothiocyanate, —NH₂—OH, —SH, —SO₃H, carboxyl, —COCl, —(CO)O(CO)R⁷—CONHNH₂, acetoxymethyl ester, substituted and unsubstituted N-hydroxysuccinimidyl ester, substituted and unsubstituted N-hydroxysulfosuccinimido ester, nitro- or fluoro or phenol ester, azide, —NCS, —CHO, —COCH₂I, phosphoramidite, phthalamido, or maleimide, wherein R⁷ is selected from the group consisting of H, alkyl and aryl;
R¹, R², R³ and R⁴ are, independently, H, methyl, ethyl, alkyl, or cyclic alkyl, aryl, substituted aryl, heteroaryl, or heterocyclic alkynyl, carboxyalkyl, aminoalkyl, haloalkyl, azidoalkyl, amide, amino acid, or peptide;
R⁵ is absent or is H, C₁₋₂₀ alkyl, carboxyl, carboxyalkyl, sulfonate, sulfonamide, halogen, hydroxy, amine, amide, nitro, cyano, O-alkyl, S-alkyl, silyl, O-silyl methyl, ethyl, isopropyl, carboxyalkyl, haloalkyl, alkylsulfhydryl, trifluoromethyl, hydrazide; and
W¹ and W² are, independently, absent or cyclic groups containing aliphatic carbon, nitrogen, oxygen, sulfur, or silicon forming a 4 to 9 membered ring with R¹ and R² or R³ and R⁴, optionally with further substituents.

17. A fluorescent biomolecule represented by Formula IV:

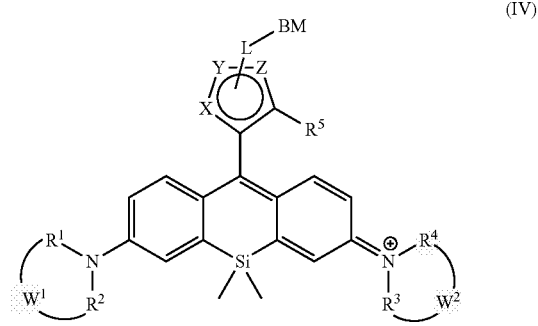

(IV)

or a salt thereof; wherein;
X, Y and Z are, independently, O, S, N, Si, C or (C=C);
L is a linking group optionally comprising a reactive group selected from a carboxylate, carboxyalkyl, maleimide, succinimidyl ester, carboxamide, propargyl, azidoalkyl, or isothiocyanate;

BM is a biomolecule, wherein the fluorescent biomolecule comprises at least one BM;

$R^1$, $R^2$, $R^3$ and $R^4$ are, independently, H, methyl, ethyl, alkyl, or cyclic alkyl, aryl, substituted aryl, heteroaryl, or heterocyclic;

$R^5$ is absent or is H, $C_{1-20}$ alkyl, carboxyl, carboxyalkyl, sulfonate, sulfonamide, halogen, hydroxy, amine, amide, nitro, cyano, O-alkyl, S-alkyl, silyl, -silyl methyl, ethyl, isopropyl, carboxyalkyl; and $W^1$ and $W^2$ are, independently, absent or cyclic groups containing aliphatic carbon, nitrogen, oxygen, sulfur, or silicon forming a 4 to 9 membered ring with $R^1$ and $R^2$ or $R^3$ and $R^4$, optionally with further substituents.

18. A pharmaceutical composition comprising a compound of claim 1 and a pharmaceutically acceptable excipient.

19. A method of in vivo imaging, the method comprising:
    (a) administering to a subject a compound of claim 1, 13, 14 or 16;
    (b) allowing the compound to distribute within the subject; and
    (c) detecting a signal emitted by the compound.

20. A method of in vivo optical imaging, the me comprising:
    (a) administering to a subject a compound of claim 1, 13, 14 or 16, wherein the compound comprises a fluorochrome;
    (b) allowing the compound to distribute within the subject;
    (c) exposing the subject to light of a wavelength absorbable by the fluorochrome; and
    (d) detecting a signal emitted by the compound.

21. An in vitro imaging method, the method comprising:
    (a) contacting a sample with a compound of claim 1, 13, 14 or 16;
    (b) allowing the compound to bind to a biological target;
    (c) optionally removing unbound compound; and
    (d) detecting signal emitted from the compound thereby to determine whether the compound has been activated by or bound to the biological target.

22. An ex vivo imaging method, the method comprising:
    (a) contacting a sample with a compound of claim 1, 13, 14 or 16;
    (b) allowing the compound to bind to a biological target;
    (c) optionally removing unbound compound; and
    (d) detecting signal emitted from the compound thereby to determine whether the compound has been activated by or bound to the biological target.

23. The method of claim 19, wherein the method is used to detect and/or monitor a disease.

24. The method of claim 23, wherein the disease is selected from the group consisting of bone disease, cancer, cardiovascular disease, atherosclerosis, restenosis, cardiac ischemia, myocardial reperfusion injury, environmental disease, dermatological disease, immunologic disease, inherited disease, infectious disease, inflammatory disease, metabolic disease, neurodegenerative disease, ophthalmic disease, and respiratory disease.

25. The compound of claim 17, wherein the BM is a protein, glycoprotein, peptide, amino acid, lipid, polysaccharide, carbohydrate, nucleoside, nucleotide, vitamin, nucleic acid, or a cell.

* * * * *

UNITED STATES PATENT AND TRADEMARK OFFICE
CERTIFICATE OF CORRECTION

PATENT NO. : 9,649,389 B2
APPLICATION NO. : 14/215979
DATED : May 16, 2017
INVENTOR(S) : Kevin Groves et al.

Page 1 of 1

It is certified that error appears in the above-identified patent and that said Letters Patent is hereby corrected as shown below:

In the Specification

At Column 4, Line 26-27, delete "$R^2$ and $R^3$ or $R^4$ and $R^5$" and replace it with -- $R^1$ and $R^2$ or $R^3$ and $R^4$ --.

At Column 17, Line 63, delete "hydrazide; and" and replace it with -- hydrazide; --.

At Column 17, Line 66-67, delete "$R^2$ and $R^3$ or $R^4$ and $R^5$" and replace it with -- $R^1$ and $R^2$ or $R^3$ and $R^4$ --.

At Column 17, Line 67, delete "substituents." and replace it with -- substituents; and --.

In the Claims

In Claim 14 at Column 107, Line 67, insert a -- , -- after -- alkylene-(optionally substituted heterocyclyl) --.

In Claim 17 at Column 109, Lines 10-11, delete "-silyl methyl" and replace it with -- O-silyl methyl --.

In Claim 20 at Column 109, Line 24, delete "me" and replace it with -- method --.

Signed and Sealed this
Seventh Day of November, 2017

Joseph Matal
*Performing the Functions and Duties of the
Under Secretary of Commerce for Intellectual Property and
Director of the United States Patent and Trademark Office*